US010597643B2

(12) United States Patent
Iyidogan et al.

(10) Patent No.: US 10,597,643 B2
(45) Date of Patent: Mar. 24, 2020

(54) POLYMERASES ENGINEERED TO REDUCE NUCLEOTIDE-INDEPENDENT DNA BINDING

(71) Applicant: OMNIOME, INC., San Diego, CA (US)

(72) Inventors: Pinar Iyidogan, San Diego, CA (US); Mark C. Wallen, San Diego, CA (US); Ying L. Liu, San Diego, CA (US); Kandaswamy Vijayan, San Diego, CA (US)

(73) Assignee: OMNIOME, INC., San Diego, CA (US)

( * ) Notice: Subject to any disclaimer, the term of this patent is extended or adjusted under 35 U.S.C. 154(b) by 66 days.

(21) Appl. No.: 15/866,353

(22) Filed: Jan. 9, 2018

(65) Prior Publication Data

US 2018/0155698 A1 Jun. 7, 2018

Related U.S. Application Data

(63) Continuation-in-part of application No. 15/581,822, filed on Apr. 28, 2017.

(60) Provisional application No. 62/534,871, filed on Jul. 20, 2017, provisional application No. 62/444,733, filed on Jan. 10, 2017, provisional application No. 62/329,489, filed on Apr. 29, 2016.

(51) Int. Cl.
*C12N 9/12* (2006.01)
*C12Q 1/6869* (2018.01)

(52) U.S. Cl.
CPC ......... *C12N 9/1252* (2013.01); *C12Q 1/6869* (2013.01)

(58) Field of Classification Search
None
See application file for complete search history.

(56) References Cited

U.S. PATENT DOCUMENTS

| | | | |
|---|---|---|---|
| 7,057,026 B2 | 6/2006 | Barnes et al. | |
| 7,264,934 B2 | 9/2007 | Fuller et al. | |
| 7,414,116 B2 | 8/2008 | Liu et al. | |
| 7,427,673 B2 | 9/2008 | Balasubramanian et al. | |

(Continued)

FOREIGN PATENT DOCUMENTS

| | | |
|---|---|---|
| WO | 9106678 | 5/1991 |
| WO | 2005019476 | 3/2005 |

(Continued)

OTHER PUBLICATIONS

UniProt Accession No. D9N168_GEOSE, published Oct. 5, 2010 (Year: 2010).*

(Continued)

*Primary Examiner* — Richard C Ekstrom

(74) *Attorney, Agent, or Firm* — Kilpatrick Townsend & Stockton LLP

(57) ABSTRACT

Provided are engineered DNA polymerases exhibiting modified functionality, and polynucleotides encoding same. Modified features include: (1) reduced catalytic activity in the presence of magnesium ions and/or (2) reduced affinity for primed template nucleic acid molecules in the absence of cognate nucleotide, and an ability to discriminate between cognate and non-cognate nucleotides under low salt conditions. Sequencing By Binding™ procedures employing the engineered polymerases have certain advantages. The engineered polymerases can have other uses as well.

42 Claims, 7 Drawing Sheets

Specification includes a Sequence Listing.

(56) References Cited

U.S. PATENT DOCUMENTS

| | | | |
|---|---|---|---|
| 7,476,503 | B2 | 1/2009 | Turner et al. |
| 7,482,120 | B2 | 1/2009 | Buzby et al. |
| 7,544,794 | B1 | 6/2009 | Benner et al. |
| 8,071,755 | B2 | 12/2011 | Efcavitch et al. |
| 8,133,672 | B2 | 3/2012 | Bjornson et al. |
| 8,236,532 | B2 | 8/2012 | Eltoukhy et al. |
| 8,632,975 | B2 | 1/2014 | Vander Horn et al. |
| 8,652,781 | B2 | 2/2014 | Korlach et al. |
| 8,703,461 | B2 | 4/2014 | Peris et al. |
| 9,279,155 | B2 | 3/2016 | Bjornson et al. |
| 9,279,154 | B2 | 6/2016 | Previte et al. |
| 9,556,480 | B2 | 1/2017 | Turner et al. |
| 2014/0186894 | A1 | 7/2014 | Liu et al. |
| 2017/0022553 | A1 | 1/2017 | Vijayan et al. |
| 2017/0314072 | A1 | 11/2017 | Vijayan et al. |
| 2018/0155698 | A1* | 6/2018 | Iyidogan .............. C12N 9/1252 |

FOREIGN PATENT DOCUMENTS

| | | |
|---|---|---|
| WO | 2007091077 | 8/2007 |
| WO | 2007123744 | 11/2007 |
| WO | 2008046612 | 4/2008 |
| WO | 2009010251 | 1/2009 |
| WO | 2009145820 | 12/2009 |
| WO | 2009145828 | 12/2009 |
| WO | 2010141390 | 12/2009 |
| WO | 2013023176 | 2/2013 |
| WO | 2014114665 | 7/2014 |
| WO | 2017190012 | 11/2017 |

OTHER PUBLICATIONS

U.S. Appl. No. 15/581,822, "Non-Final Office Action", dated May 17, 2019, 13 pages.

Knapp et al., "Fluoride-Cleavable, Fluorescently Labelled Reversible Terminators: Synthesis and Use in Primer Extension", Chemistry—A European Journal, vol. 17, Issue 10, Mar. 2011, pp. 2903-2915.

Bibillo et al., "Functional roles of carboxylate residues comprising the DNA polymerase active site triad of Ty3 reverse transcriptase", Nucleic acids research 33.1, 2005, 171-181.

Gangurde et al., "A Carboxylate Triad Is Essential for the Polymerase Activity of Escherichia coli DNA Polymerase I (Klenow Fragment) Presence of Two Functional Triads at the Catalytic Center", Journal of Biological Chemistry 275.26, 2000, 19685-19692.

Murphy et al., "A triad interaction in the fingers subdomain of DNA polymerase beta controls polymerase activity", Journal of the American Chemical Society 133.16, 2011, 6279-6287.

Sandalli et al., "Characterization of catalytic carboxylate triad in non-replicative DNA polymerase III (pol E) of Geobacillus kaustophilus HTA", Cellular and molecular biology 58.1, 2012, 44-49.

PCT/US2017/030135, "International Preliminary Report on Patentability", dated Nov. 8, 2018, 8 pages.

PCT/US2018/013007, "International Search Report and Written Opinion" (corrected), dated Jun. 20, 2018, 18 pages.

PCT/US2018/013007, "International Search Report and Written Opinion", dated May 14, 2018, 18 pages.

PCT/US2018/013007, "International Preliminary Report on Patentability", dated Jul. 25, 2019, 11 pages.

SG11201809522W, "Written Opinion", dated Sep. 9, 2019, 10 pages.

Anker et al., "Biosensing with Plasmonic Nanosensors", Nature Materials 7, No. 6, Jun. 2008, pp. 442-453.

Brockman et al., "A Multistep Chemical Modification Procedure to Create DNA Arrays on Gold Surfaces for the Study of Protein—DNA Interactions with Surface Plasmon Resonance Imaging", Journal of the American Chemical Society 121, Sep. 1999, pp. 8044-8051.

Brown et al., "Pre-Steady-State Kinetic Analysis of Truncated and Full-Length Saccharomyces cerevisiae DNA Polymerase Eta", Journal of Nucleic Acids, 2010, Article ID 871939, 11 pages.

Chen et al., "The history and advances of reversible terminators used in new generations of sequencing technology", Genomics, Proteomics & Bioinformatics 11(1), 2013, pp. 34-40.

Escobedo et al., "Integrated nanohole array surface plasmon resonance sensing device using a dual-wavelength source", Journal of Micromechanics and Microengineering 21, No. 11, Nov. 1, 2011.

Kaushik et al., "Biochemical Analysis of Catalytically Crucial Aspartate Mutants of Human Immunodeficiency Virus Type 1 Reverse Transcriptase", Biochemistry, 35, 1996, pp. 11536-11546.

Kim, "An FET-type charge sensor for highly sensitive detection of DNA sequence", Biosensors and Bioelectronics, Microsensors and Microsystems, 20, No. 1, Jul. 30, 2004, pp. 69-74.

Ma et al., "Enhancement of Polymerase Activity of the Large Fragment in DNA Polymerase I from Geobacillus stearothermophilus by Site-Directed Mutagenesis at the Active Site", Biomed Research International, Jan. 1, 2016, pp. 1-8.

Markiewicz et al., "Single-Molecule Microscopy Reveals New Insights into Nucleotide Selection by DNA Polymerase I", Nucleic Acids Research, vol. 40, No. 16, Jun. 4, 2012, pp. 7975-7984.

Nazirizadeh , "Low-cost label-free biosensors using photonic crystals embedded between crossed polarizers", Optics Express, vol. 18, No. 18, Aug. 30, 2010, pp. 19120-19128.

Patel, "Insights into DNA Polymerization Mechanisms from Structure and Function Analysis of HIV-1 Reverse Transcriptase.", Biochemistry 34, 1995, pp. 5351-5363.

PCT/US2017/030135, "International Search Report and Written Opinion", dated Jul. 21, 2017, 12 pages.

PCT/US2018/013007, "Invitation to Pay Add'l Fees and Partial Search Report", dated Mar. 19, 2018, 6 pages.

Roettger et al., "Mismatched and Matched dNTP Incorporation by DNA Polymerase β Proceed via Analogues Kinetic Pathways", Biochemistry, 47, Sep. 16, 2008, pp. 9718-9727.

Sandalli et al., "Characterization of catalytic carboxylate triad in non-replicative DNA polymerase III (pol E) of Geobacillus kaustophilus HTA", Cellular and molecular biology (Noisy-le-Grand, France) 58.1, 2012, pp. 44-49.

Schultz et al., "Single-target molecule detection with nonbleaching multicolor optical immunolabels", PNAS, vol. 96, No. 3, Feb. 1, 2000, pp. 996-1001.

Star et al., "Electronic Detection of Specific Protein Binding Using Nanotube FET Devices", Nano Letters 3, No. 4, Apr. 1, 2003, pp. 459-463.

Tsai et al., "Site-specific labeling of T7 DNA polymerase with a conformationally sensitive flurophore and its use in detecting single-nucleotide polymorphisms", Analytical Biochemistry, vol. 384, No. 1, Academic Press Inc., New York, Jan. 1, 2009, pp. 136-144.

Vaidyanathan et al., "Binding kinetics of DNA-protein interaction using surface plasmon resonance", Protocol Exchange, May 22, 2013.

Walsh, "Synthetic Nucleotides as Probes of DNA Polymerase Specificity", Journal of Nucleic Acids, vol. 2012, Article ID 530963, 17 pages.

Washington et al., "Human DNA Polymerase Utilizes Different Nucleotide Incorporation Mechanisms Dependent upon the Template Base", Molecular and Cellular Biology, vol. 24, No. 2, Jan. 2004, pp. 936-943.

Xia et al., "DNA Mismatch Synthesis Complexes Provide Insights into Base Selectivity of a B family DNA Polymerase", J Am Chem Soc. 135(1), Jan. 9, 2013, pp. 193-202.

CA3,022,431, "Office Action", dated Oct. 21, 2019, 4 pages.

* cited by examiner

SEQUENCE LISTING

<160> NUMBER OF SEQ ID NOS: 13

<210> SEQ ID NO 1
<211> LENGTH: 604
<212> TYPE: PRT
<213> ORGANISM: Bacillus stearothermophilus
<220> FEATURE:
<221> NAME/KEY: MISC_FEATURE
<222> LOCATION: (5)..(10)
<223> OTHER INFORMATION: Polyhistidine tag motif
<220> FEATURE:
<221> NAME/KEY: MISC_FEATURE
<222> LOCATION: (17)..(18)
<223> OTHER INFORMATION: Thrombin cleavage site
<220> FEATURE:
<221> NAME/KEY: MISC_FEATURE
<222> LOCATION: (23)..(23)
<223> OTHER INFORMATION: Cystine residue
<220> FEATURE:
<221> NAME/KEY: MISC_FEATURE
<222> LOCATION: (27)..(604)
<223> OTHER INFORMATION: Bst polymerase polypeptide sequence with
      replacement of naturally occurring cysteine residues

<400> SEQUENCE: 1

Met Gly Ser Ser His His His His His His Ser Ser Gly Leu Val Pro
1               5                   10                  15

Arg Gly Ser His Met Ser Cys Gly Ala Ala Met Ala Phe Thr Leu Ala
            20                  25                  30

Asp Arg Val Thr Glu Glu Met Leu Ala Asp Lys Ala Ala Leu Val Val
        35                  40                  45

Glu Val Val Glu Glu Asn Tyr His Asp Ala Pro Ile Val Gly Ile Ala
    50                  55                  60

Val Val Asn Glu His Gly Arg Phe Phe Leu Arg Pro Glu Thr Ala Leu
65                  70                  75                  80

Ala Asp Pro Gln Phe Val Ala Trp Leu Gly Asp Glu Thr Lys Lys Lys
                85                  90                  95

Ser Met Phe Asp Ser Lys Arg Ala Ala Val Ala Leu Lys Trp Lys Gly
            100                 105                 110

Ile Glu Leu Ala Gly Val Ser Phe Asp Leu Leu Leu Ala Ala Tyr Leu
        115                 120                 125

Leu Asp Pro Ala Gln Gly Val Asp Asp Val Ala Ala Ala Ala Lys Met
    130                 135                 140

Lys Gln Tyr Glu Ala Val Arg Pro Asp Glu Ala Val Tyr Gly Lys Gly
145                 150                 155                 160

Ala Lys Arg Ala Val Pro Asp Glu Pro Val Leu Ala Glu His Leu Val
                165                 170                 175

Arg Lys Ala Ala Ala Ile Trp Glu Leu Glu Arg Pro Phe Leu Asp Glu
            180                 185                 190

Leu Arg Arg Asn Glu Gln Asp Arg Leu Leu Val Glu Leu Glu Gln Pro
        195                 200                 205

Leu Ser Ser Ile Leu Ala Glu Met Glu Phe Ala Gly Val Lys Val Asp
    210                 215                 220

Thr Lys Arg Leu Glu Gln Met Gly Lys Glu Leu Ala Glu Gln Leu Gly
225                 230                 235                 240

Thr Val Glu Gln Arg Ile Tyr Glu Leu Ala Gly Gln Glu Phe Asn Ile
                245                 250                 255

Asn Ser Pro Lys Gln Leu Gly Val Ile Leu Phe Glu Lys Leu Gln Leu
            260                 265                 270

Pro Val Leu Lys Lys Thr Lys Thr Gly Tyr Ser Thr Ser Ala Asp Val

-continued

```
                275                 280                 285
Leu Glu Lys Leu Ala Pro Tyr His Glu Ile Val Glu Asn Ile Leu His
    290                 295                 300
Tyr Arg Gln Leu Gly Lys Leu Gln Ser Thr Tyr Ile Glu Gly Leu Leu
305                 310                 315                 320
Lys Val Val Arg Pro Ala Thr Lys Lys Val His Thr Ile Phe Asn Gln
                325                 330                 335
Ala Leu Thr Gln Thr Gly Arg Leu Ser Ser Thr Glu Pro Asn Leu Gln
            340                 345                 350
Asn Ile Pro Ile Arg Leu Glu Glu Gly Arg Lys Ile Arg Gln Ala Phe
        355                 360                 365
Val Pro Ser Glu Ser Asp Trp Leu Ile Phe Ala Ala Asp Tyr Ser Gln
    370                 375                 380
Ile Glu Leu Arg Val Leu Ala His Ile Ala Glu Asp Asp Asn Leu Met
385                 390                 395                 400
Glu Ala Phe Arg Arg Asp Leu Asp Ile His Thr Lys Thr Ala Met Asp
                405                 410                 415
Ile Phe Gln Val Ser Glu Asp Glu Val Thr Pro Asn Met Arg Arg Gln
            420                 425                 430
Ala Lys Ala Val Asn Tyr Gly Ile Val Tyr Gly Ile Ser Asp Tyr Gly
        435                 440                 445
Leu Ala Gln Asn Leu Asn Ile Ser Arg Lys Glu Ala Ala Glu Phe Ile
    450                 455                 460
Glu Arg Tyr Phe Glu Ser Phe Pro Gly Val Lys Arg Tyr Met Glu Asn
465                 470                 475                 480
Ile Val Gln Glu Ala Lys Gln Lys Gly Tyr Val Thr Thr Leu Leu His
                485                 490                 495
Arg Arg Arg Tyr Leu Pro Asp Ile Thr Ser Arg Asn Phe Asn Val Arg
            500                 505                 510
Ser Phe Ala Glu Arg Met Ala Met Asn Thr Pro Ile Gln Gly Ser Ala
        515                 520                 525
Ala Asp Ile Ile Lys Lys Ala Met Ile Asp Leu Asn Ala Arg Leu Lys
    530                 535                 540
Glu Glu Arg Leu Gln Ala His Leu Leu Leu Gln Val His Asp Glu Leu
545                 550                 555                 560
Ile Leu Glu Ala Pro Lys Glu Glu Met Glu Arg Leu Ala Arg Leu Val
                565                 570                 575
Pro Glu Val Met Glu Gln Ala Val Thr Leu Arg Val Pro Leu Lys Val
            580                 585                 590
Asp Tyr His Tyr Gly Ser Thr Trp Tyr Asp Ala Lys
        595                 600
```

<210> SEQ ID NO 2
<211> LENGTH: 587
<212> TYPE: PRT
<213> ORGANISM: Bacillus stearothermophilus
<220> FEATURE:
<221> NAME/KEY: MISC_FEATURE
<222> LOCATION: (1)..(587)
<223> OTHER INFORMATION: Product resulting from thrombin cleavage of the
      protein sequence identified as SEQ ID NO:1

<400> SEQUENCE: 2

```
Gly Ser His Met Ser Cys Gly Ala Ala Met Ala Phe Thr Leu Ala Asp
1               5                   10                  15
Arg Val Thr Glu Glu Met Leu Ala Asp Lys Ala Ala Leu Val Val Glu
```

```
            20                  25                  30
Val Val Glu Glu Asn Tyr His Asp Ala Pro Ile Val Gly Ile Ala Val
            35                  40                  45

Val Asn Glu His Gly Arg Phe Phe Leu Arg Pro Glu Thr Ala Leu Ala
            50                  55                  60

Asp Pro Gln Phe Val Ala Trp Leu Gly Asp Glu Thr Lys Lys Lys Ser
65                      70                  75                  80

Met Phe Asp Ser Lys Arg Ala Ala Val Ala Leu Lys Trp Lys Gly Ile
                85                  90                  95

Glu Leu Ala Gly Val Ser Phe Asp Leu Leu Ala Ala Tyr Leu Leu
                    100                 105                 110

Asp Pro Ala Gln Gly Val Asp Val Ala Ala Ala Lys Met Lys
                115                 120                 125

Gln Tyr Glu Ala Val Arg Pro Asp Glu Ala Val Tyr Gly Lys Gly Ala
            130                 135                 140

Lys Arg Ala Val Pro Asp Glu Pro Val Leu Ala Glu His Leu Val Arg
145                 150                 155                 160

Lys Ala Ala Ile Trp Glu Leu Glu Arg Pro Phe Leu Asp Glu Leu
                    165                 170                 175

Arg Arg Asn Glu Gln Asp Arg Leu Leu Val Glu Leu Glu Gln Pro Leu
            180                 185                 190

Ser Ser Ile Leu Ala Glu Met Glu Phe Ala Gly Val Lys Val Asp Thr
            195                 200                 205

Lys Arg Leu Glu Gln Met Gly Lys Glu Leu Ala Glu Gln Leu Gly Thr
            210                 215                 220

Val Glu Gln Arg Ile Tyr Glu Leu Ala Gly Gln Glu Phe Asn Ile Asn
225                 230                 235                 240

Ser Pro Lys Gln Leu Gly Val Ile Leu Phe Glu Lys Leu Gln Leu Pro
                    245                 250                 255

Val Leu Lys Lys Thr Lys Thr Gly Tyr Ser Thr Ser Ala Asp Val Leu
            260                 265                 270

Glu Lys Leu Ala Pro Tyr His Glu Ile Val Glu Asn Ile Leu His Tyr
            275                 280                 285

Arg Gln Leu Gly Lys Leu Gln Ser Thr Tyr Ile Glu Gly Leu Leu Lys
            290                 295                 300

Val Val Arg Pro Ala Thr Lys Lys Val His Thr Ile Phe Asn Gln Ala
305                 310                 315                 320

Leu Thr Gln Thr Gly Arg Leu Ser Ser Thr Glu Pro Asn Leu Gln Asn
                    325                 330                 335

Ile Pro Ile Arg Leu Glu Glu Gly Arg Lys Ile Arg Gln Ala Phe Val
                340                 345                 350

Pro Ser Glu Ser Asp Trp Leu Ile Phe Ala Ala Asp Tyr Ser Gln Ile
            355                 360                 365

Glu Leu Arg Val Leu Ala His Ile Ala Glu Asp Asn Leu Met Glu
            370                 375                 380

Ala Phe Arg Arg Asp Leu Asp Ile His Thr Lys Thr Ala Met Asp Ile
385                 390                 395                 400

Phe Gln Val Ser Glu Asp Glu Val Thr Pro Asn Met Arg Arg Gln Ala
                    405                 410                 415

Lys Ala Val Asn Tyr Gly Ile Val Tyr Gly Ile Ser Asp Tyr Gly Leu
                420                 425                 430

Ala Gln Asn Leu Asn Ile Ser Arg Lys Glu Ala Ala Glu Phe Ile Glu
            435                 440                 445
```

```
Arg Tyr Phe Glu Ser Phe Pro Gly Val Lys Arg Tyr Met Glu Asn Ile
            450                 455                 460

Val Gln Glu Ala Lys Gln Lys Gly Tyr Val Thr Leu Leu His Arg
465                 470                 475                 480

Arg Arg Tyr Leu Pro Asp Ile Thr Ser Arg Asn Phe Asn Val Arg Ser
            485                 490                 495

Phe Ala Glu Arg Met Ala Met Asn Thr Pro Ile Gln Gly Ser Ala Ala
            500                 505                 510

Asp Ile Ile Lys Lys Ala Met Ile Asp Leu Asn Ala Arg Leu Lys Glu
            515                 520                 525

Glu Arg Leu Gln Ala His Leu Leu Leu Gln Val His Asp Glu Leu Ile
            530                 535                 540

Leu Glu Ala Pro Lys Glu Glu Met Glu Arg Leu Ala Arg Leu Val Pro
545                 550                 555                 560

Glu Val Met Glu Gln Ala Val Thr Leu Arg Val Pro Leu Lys Val Asp
            565                 570                 575

Tyr His Tyr Gly Ser Thr Trp Tyr Asp Ala Lys
            580                 585
```

<210> SEQ ID NO 3
<211> LENGTH: 578
<212> TYPE: PRT
<213> ORGANISM: Bacillus stearothermophilus
<220> FEATURE:
<221> NAME/KEY: MISC_FEATURE
<222> LOCATION: (1)..(578)
<223> OTHER INFORMATION: Protein expression product of the cysteine-
      substituted Bst-f polymerase

<400> SEQUENCE: 3

```
Met Ala Phe Thr Leu Ala Asp Arg Val Thr Glu Glu Met Leu Ala Asp
1               5                   10                  15

Lys Ala Leu Val Val Glu Val Val Glu Glu Asn Tyr His Asp Ala
            20                  25                  30

Pro Ile Val Gly Ile Ala Val Val Asn Glu His Gly Arg Phe Phe Leu
            35                  40                  45

Arg Pro Glu Thr Ala Leu Ala Asp Pro Gln Phe Val Ala Trp Leu Gly
50                  55                  60

Asp Glu Thr Lys Lys Ser Met Phe Asp Ser Lys Arg Ala Ala Val
65                  70                  75                  80

Ala Leu Lys Trp Lys Gly Ile Glu Leu Ala Gly Val Ser Phe Asp Leu
            85                  90                  95

Leu Leu Ala Ala Tyr Leu Leu Asp Pro Ala Gln Gly Val Asp Asp Val
            100                 105                 110

Ala Ala Ala Ala Lys Met Lys Gln Tyr Glu Ala Val Arg Pro Asp Glu
            115                 120                 125

Ala Val Tyr Gly Lys Gly Ala Lys Arg Ala Val Pro Asp Glu Pro Val
            130                 135                 140

Leu Ala Glu His Leu Val Arg Lys Ala Ala Ile Trp Glu Leu Glu
145                 150                 155                 160

Arg Pro Phe Leu Asp Glu Leu Arg Arg Asn Glu Gln Asp Arg Leu Leu
            165                 170                 175

Val Glu Leu Glu Gln Pro Leu Ser Ser Ile Leu Ala Glu Met Glu Phe
            180                 185                 190

Ala Gly Val Lys Val Asp Thr Lys Arg Leu Glu Gln Met Gly Lys Glu
            195                 200                 205
```

```
Leu Ala Glu Gln Leu Gly Thr Val Glu Gln Arg Ile Tyr Glu Leu Ala
210                 215                 220
Gly Gln Glu Phe Asn Ile Asn Ser Pro Lys Gln Leu Gly Val Ile Leu
225                 230                 235                 240
Phe Glu Lys Leu Gln Leu Pro Val Leu Lys Lys Thr Lys Thr Gly Tyr
                245                 250                 255
Ser Thr Ser Ala Asp Val Leu Glu Lys Leu Ala Pro Tyr His Glu Ile
            260                 265                 270
Val Glu Asn Ile Leu His Tyr Arg Gln Leu Gly Lys Leu Gln Ser Thr
        275                 280                 285
Tyr Ile Glu Gly Leu Leu Lys Val Val Arg Pro Ala Thr Lys Lys Val
    290                 295                 300
His Thr Ile Phe Asn Gln Ala Leu Thr Gln Thr Gly Arg Leu Ser Ser
305                 310                 315                 320
Thr Glu Pro Asn Leu Gln Asn Ile Pro Ile Arg Leu Glu Glu Gly Arg
                325                 330                 335
Lys Ile Arg Gln Ala Phe Val Pro Ser Glu Ser Asp Trp Leu Ile Phe
            340                 345                 350
Ala Ala Asp Tyr Ser Gln Ile Glu Leu Arg Val Leu Ala His Ile Ala
        355                 360                 365
Glu Asp Asp Asn Leu Met Glu Ala Phe Arg Arg Asp Leu Asp Ile His
    370                 375                 380
Thr Lys Thr Ala Met Asp Ile Phe Gln Val Ser Glu Asp Glu Val Thr
385                 390                 395                 400
Pro Asn Met Arg Arg Gln Ala Lys Ala Val Asn Tyr Gly Ile Val Tyr
                405                 410                 415
Gly Ile Ser Asp Tyr Gly Leu Ala Gln Asn Leu Asn Ile Ser Arg Lys
            420                 425                 430
Glu Ala Ala Glu Phe Ile Glu Arg Tyr Phe Glu Ser Phe Pro Gly Val
        435                 440                 445
Lys Arg Tyr Met Glu Asn Ile Val Gln Glu Ala Lys Gln Lys Gly Tyr
    450                 455                 460
Val Thr Thr Leu Leu His Arg Arg Arg Tyr Leu Pro Asp Ile Thr Ser
465                 470                 475                 480
Arg Asn Phe Asn Val Arg Ser Phe Ala Glu Arg Met Ala Met Asn Thr
                485                 490                 495
Pro Ile Gln Gly Ser Ala Ala Asp Ile Ile Lys Lys Ala Met Ile Asp
            500                 505                 510
Leu Asn Ala Arg Leu Lys Glu Glu Arg Leu Gln Ala His Leu Leu Leu
        515                 520                 525
Gln Val His Asp Glu Leu Ile Leu Glu Ala Pro Lys Glu Glu Met Glu
    530                 535                 540
Arg Leu Ala Arg Leu Val Pro Glu Val Met Glu Gln Ala Val Thr Leu
545                 550                 555                 560
Arg Val Pro Leu Lys Val Asp Tyr His Tyr Gly Ser Thr Trp Tyr Asp
                565                 570                 575
Ala Lys

<210> SEQ ID NO 4
<211> LENGTH: 578
<212> TYPE: PRT
<213> ORGANISM: Bacillus stearothermophilus
<220> FEATURE:
<221> NAME/KEY: MISC_FEATURE
```

<222> LOCATION: (1)..(578)
<223> OTHER INFORMATION: Bacillus DNA polymerase C-terminal fragment
       lacking 5'-3' exonuclease activity

<400> SEQUENCE: 4

Met Ala Phe Thr Leu Ala Asp Arg Val Thr Glu Glu Met Leu Ala Asp
1               5                   10                  15

Lys Ala Ala Leu Val Val Glu Val Val Glu Glu Asn Tyr His Asp Ala
            20                  25                  30

Pro Ile Val Gly Ile Ala Val Val Asn Glu His Gly Arg Phe Phe Leu
        35                  40                  45

Arg Pro Glu Thr Ala Leu Ala Asp Pro Gln Phe Val Ala Trp Leu Gly
50                  55                  60

Asp Glu Thr Lys Lys Lys Ser Met Phe Asp Ser Lys Arg Ala Ala Val
65                  70                  75                  80

Ala Leu Lys Trp Lys Gly Ile Glu Leu Cys Gly Val Ser Phe Asp Leu
                85                  90                  95

Leu Leu Ala Ala Tyr Leu Leu Asp Pro Ala Gln Gly Val Asp Asp Val
            100                 105                 110

Ala Ala Ala Ala Lys Met Lys Gln Tyr Glu Ala Val Arg Pro Asp Glu
        115                 120                 125

Ala Val Tyr Gly Lys Gly Ala Lys Arg Ala Val Pro Asp Glu Pro Val
130                 135                 140

Leu Ala Glu His Leu Val Arg Lys Ala Ala Ala Ile Trp Glu Leu Glu
145                 150                 155                 160

Arg Pro Phe Leu Asp Glu Leu Arg Arg Asn Glu Gln Asp Arg Leu Leu
                165                 170                 175

Val Glu Leu Glu Gln Pro Leu Ser Ser Ile Leu Ala Glu Met Glu Phe
            180                 185                 190

Ala Gly Val Lys Val Asp Thr Lys Arg Leu Glu Gln Met Gly Lys Glu
        195                 200                 205

Leu Ala Glu Gln Leu Gly Thr Val Glu Gln Arg Ile Tyr Glu Leu Ala
210                 215                 220

Gly Gln Glu Phe Asn Ile Asn Ser Pro Lys Gln Leu Gly Val Ile Leu
225                 230                 235                 240

Phe Glu Lys Leu Gln Leu Pro Val Leu Lys Lys Thr Lys Thr Gly Tyr
                245                 250                 255

Ser Thr Ser Ala Asp Val Leu Glu Lys Leu Ala Pro Tyr His Glu Ile
            260                 265                 270

Val Glu Asn Ile Leu His Tyr Arg Gln Leu Gly Lys Leu Gln Ser Thr
        275                 280                 285

Tyr Ile Glu Gly Leu Leu Lys Val Val Arg Pro Ala Thr Lys Lys Val
290                 295                 300

His Thr Ile Phe Asn Gln Ala Leu Thr Gln Thr Gly Arg Leu Ser Ser
305                 310                 315                 320

Thr Glu Pro Asn Leu Gln Asn Ile Pro Ile Arg Leu Glu Glu Gly Arg
                325                 330                 335

Lys Ile Arg Gln Ala Phe Val Pro Ser Glu Ser Asp Trp Leu Ile Phe
            340                 345                 350

Ala Ala Asp Tyr Ser Gln Ile Glu Leu Arg Val Leu Ala His Ile Ala
        355                 360                 365

Glu Asp Asp Asn Leu Met Glu Ala Phe Arg Arg Asp Leu Asp Ile His
370                 375                 380

Thr Lys Thr Ala Met Asp Ile Phe Gln Val Ser Glu Asp Glu Val Thr

```
            385                 390                 395                 400
Pro Asn Met Arg Arg Gln Ala Lys Ala Val Asn Tyr Gly Ile Val Tyr
                405                 410                 415
Gly Ile Ser Asp Tyr Gly Leu Ala Gln Asn Leu Asn Ile Ser Arg Lys
                420                 425                 430
Glu Ala Ala Glu Phe Ile Glu Arg Tyr Phe Glu Ser Phe Pro Gly Val
                435                 440                 445
Lys Arg Tyr Met Glu Asn Ile Val Gln Glu Ala Lys Gln Lys Gly Tyr
                450                 455                 460
Val Thr Thr Leu Leu His Arg Arg Tyr Leu Pro Asp Ile Thr Ser
465                 470                 475                 480
Arg Asn Phe Asn Val Arg Ser Phe Ala Glu Arg Met Ala Met Asn Thr
                485                 490                 495
Pro Ile Gln Gly Ser Ala Ala Asp Ile Ile Lys Lys Ala Met Ile Asp
                500                 505                 510
Leu Asn Ala Arg Leu Lys Glu Glu Arg Leu Gln Ala His Leu Leu Leu
                515                 520                 525
Gln Val His Asp Glu Leu Ile Leu Glu Ala Pro Lys Glu Glu Met Glu
            530                 535                 540
Arg Leu Cys Arg Leu Val Pro Glu Val Met Glu Gln Ala Val Thr Leu
545                 550                 555                 560
Arg Val Pro Leu Lys Val Asp Tyr His Tyr Gly Ser Thr Trp Tyr Asp
                565                 570                 575
Ala Lys
```

```
<210> SEQ ID NO 5
<211> LENGTH: 9
<212> TYPE: PRT
<213> ORGANISM: Bacillus stearothermophilus
<220> FEATURE:
<221> NAME/KEY: MISC_FEATURE
<222> LOCATION: (1)..(9)
<223> OTHER INFORMATION: N-terminal sequence containing Cys residue

<400> SEQUENCE: 5

Gly Ser His Met Ser Cys Gly Ala Ala
1               5

<210> SEQ ID NO 6
<211> LENGTH: 26
<212> TYPE: PRT
<213> ORGANISM: Bacillus stearothermophilus
<220> FEATURE:
<221> NAME/KEY: MISC_FEATURE
<222> LOCATION: (1)..(26)
<223> OTHER INFORMATION: N-terminal sequence containing polyhistidine
      tag, thrombin cleavage site, and Cys residue

<400> SEQUENCE: 6

Met Gly Ser Ser His His His His His His Ser Ser Gly Leu Val Pro
1               5                   10                  15

Arg Gly Ser His Met Ser Cys Gly Ala Ala
            20                  25

<210> SEQ ID NO 7
<211> LENGTH: 10
<212> TYPE: DNA
<213> ORGANISM: Artificial Sequence
<220> FEATURE:
<223> OTHER INFORMATION: DNA sequence to be determined using synthetic
      template
```

```
<400> SEQUENCE: 7
tagcatcaga                                                          10

<210> SEQ ID NO 8
<211> LENGTH: 10
<212> TYPE: DNA
<213> ORGANISM: Artificial Sequence
<220> FEATURE:
<223> OTHER INFORMATION: DNA sequence to be determined using synthetic
      template

<400> SEQUENCE: 8
ccctgtcatg                                                          10

<210> SEQ ID NO 9
<211> LENGTH: 10
<212> TYPE: DNA
<213> ORGANISM: Artificial Sequence
<220> FEATURE:
<223> OTHER INFORMATION: DNA sequence to be determined using synthetic
      template

<400> SEQUENCE: 9
cccatttatg                                                          10

<210> SEQ ID NO 10
<211> LENGTH: 10
<212> TYPE: DNA
<213> ORGANISM: Artificial Sequence
<220> FEATURE:
<223> OTHER INFORMATION: DNA sequence to be determined using synthetic
      template

<400> SEQUENCE: 10
ccgattcgtc                                                          10

<210> SEQ ID NO 11
<211> LENGTH: 10
<212> TYPE: DNA
<213> ORGANISM: Artificial Sequence
<220> FEATURE:
<223> OTHER INFORMATION: DNA sequence to be determined using synthetic
      template

<400> SEQUENCE: 11
ccatgtttca                                                          10

<210> SEQ ID NO 12
<211> LENGTH: 585
<212> TYPE: PRT
<213> ORGANISM: Bacillus subtilis

<400> SEQUENCE: 12
```

| | | | | | | | | | | | | | | | |
|---|---|---|---|---|---|---|---|---|---|---|---|---|---|---|---|
| Met | Asp | Gln | Ser | Leu | Glu | Asp | Ile | Asn | Val | Lys | Thr | Val | Thr | Asp | Val |
| 1 | | | | 5 | | | | | 10 | | | | | 15 | |
| Thr | Ser | Asp | Ile | Leu | Val | Ser | Pro | Ser | Ala | Phe | Val | Val | Glu | Gln | Ile |
| | | | 20 | | | | | 25 | | | | | 30 | | |
| Gly | Asp | Asn | Tyr | His | Glu | Glu | Pro | Ile | Leu | Gly | Phe | Ser | Ile | Val | Asn |
| | | | 35 | | | | 40 | | | | | 45 | | | |
| Glu | Thr | Gly | Ala | Tyr | Phe | Ile | Pro | Lys | Asp | Ile | Ala | Val | Glu | Ser | Glu |
| | 50 | | | | | 55 | | | | | 60 | | | | |
| Val | Phe | Lys | Glu | Trp | Val | Glu | Asn | Asp | Glu | Gln | Lys | Lys | Trp | Val | Phe |
| 65 | | | | | 70 | | | | | 75 | | | | | 80 |

```
Asp Ser Lys Arg Ala Val Val Ala Leu Arg Trp Gln Gly Ile Glu Leu
                85                  90                  95
Lys Gly Ala Glu Phe Asp Thr Leu Leu Ala Ala Tyr Ile Ile Asn Pro
            100                 105                 110
Gly Asn Ser Tyr Asp Asp Val Ala Ser Val Ala Lys Asp Tyr Gly Leu
        115                 120                 125
His Ile Val Ser Ser Asp Glu Ser Val Tyr Gly Lys Gly Ala Lys Arg
    130                 135                 140
Ala Val Pro Ser Glu Asp Val Leu Ser Glu His Leu Gly Arg Lys Ala
145                 150                 155                 160
Leu Ala Ile Gln Ser Leu Arg Glu Lys Leu Val Gln Glu Leu Glu Asn
                165                 170                 175
Asn Asp Gln Leu Glu Leu Phe Glu Glu Leu Glu Met Pro Leu Ala Leu
            180                 185                 190
Ile Leu Gly Glu Met Glu Ser Thr Gly Val Lys Val Asp Val Asp Arg
        195                 200                 205
Leu Lys Arg Met Gly Glu Glu Leu Gly Ala Lys Leu Lys Glu Tyr Glu
    210                 215                 220
Glu Lys Ile His Glu Ile Ala Gly Glu Pro Phe Asn Ile Asn Ser Pro
225                 230                 235                 240
Lys Gln Leu Gly Val Ile Leu Phe Glu Lys Ile Gly Leu Pro Val Val
                245                 250                 255
Lys Lys Thr Lys Thr Gly Tyr Ser Thr Ser Ala Asp Val Leu Glu Lys
            260                 265                 270
Leu Ala Asp Lys His Asp Ile Val Asp Tyr Ile Leu Gln Tyr Arg Gln
        275                 280                 285
Ile Gly Lys Leu Gln Ser Thr Tyr Ile Glu Gly Leu Leu Lys Val Thr
    290                 295                 300
Arg Pro Asp Ser His Lys Val His Thr Arg Phe Asn Gln Ala Leu Thr
305                 310                 315                 320
Gln Thr Gly Arg Leu Ser Ser Thr Asp Pro Asn Leu Gln Asn Ile Pro
                325                 330                 335
Ile Arg Leu Glu Glu Gly Arg Lys Ile Arg Gln Ala Phe Val Pro Ser
            340                 345                 350
Glu Lys Asp Trp Leu Ile Phe Ala Ala Asp Tyr Ser Gln Ile Glu Leu
        355                 360                 365
Arg Val Leu Ala His Ile Ser Lys Asp Glu Asn Leu Ile Glu Ala Phe
    370                 375                 380
Thr Asn Asp Met Asp Ile His Thr Lys Thr Ala Met Asp Val Phe His
385                 390                 395                 400
Val Ala Lys Asp Glu Val Thr Ser Ala Met Arg Arg Gln Ala Lys Ala
                405                 410                 415
Val Asn Phe Gly Ile Val Tyr Gly Ile Ser Asp Tyr Gly Leu Ser Gln
            420                 425                 430
Asn Leu Gly Ile Thr Arg Lys Glu Ala Gly Ala Phe Ile Asp Arg Tyr
        435                 440                 445
Leu Glu Ser Phe Gln Gly Val Lys Ala Tyr Met Glu Asp Ser Val Gln
    450                 455                 460
Glu Ala Lys Gln Lys Gly Tyr Val Thr Thr Leu Met His Arg Arg Arg
465                 470                 475                 480
Tyr Ile Pro Glu Leu Thr Ser Arg Asn Phe Asn Ile Arg Ser Phe Ala
                485                 490                 495
```

```
Glu Arg Thr Ala Met Asn Thr Pro Ile Gln Gly Ser Ala Ala Asp Ile
            500                 505                 510

Ile Lys Lys Ala Met Ile Asp Met Ala Ala Lys Leu Lys Glu Lys Gln
        515                 520                 525

Leu Lys Ala Arg Leu Leu Leu Gln Val His Asp Glu Leu Ile Phe Glu
    530                 535                 540

Ala Pro Lys Glu Glu Ile Glu Ile Leu Glu Lys Leu Val Pro Glu Val
545                 550                 555                 560

Met Glu His Ala Leu Ala Leu Asp Val Pro Leu Lys Val Asp Phe Ala
                565                 570                 575

Ser Gly Pro Ser Trp Tyr Asp Ala Lys
            580                 585

<210> SEQ ID NO 13
<211> LENGTH: 611
<212> TYPE: PRT
<213> ORGANISM: Bacillus subtilis
<220> FEATURE:
<221> NAME/KEY: MISC_FEATURE
<222> LOCATION: (1)..(611)
<223> OTHER INFORMATION: Cys-Bsu (CBU) polypeptide sequence
<220> FEATURE:
<221> NAME/KEY: MISC_FEATURE
<222> LOCATION: (5)..(10)
<223> OTHER INFORMATION: Polyhistidine tag motif
<220> FEATURE:
<221> NAME/KEY: MISC_FEATURE
<222> LOCATION: (17)..(18)
<223> OTHER INFORMATION: Thrombin cleavage site
<220> FEATURE:
<221> NAME/KEY: MISC_FEATURE
<222> LOCATION: (27)..(611)
<223> OTHER INFORMATION: Bsu DNA polymerase polypeptide sequence

<400> SEQUENCE: 13

Met Gly Ser Ser His His His His His His Ser Ser Gly Leu Val Pro
1               5                   10                  15

Arg Gly Ser His Met Ser Cys Gly Ala Ala Gly Asp Gln Ser Leu Glu
            20                  25                  30

Asp Ile Asn Val Lys Thr Val Thr Asp Val Thr Ser Asp Ile Leu Val
        35                  40                  45

Ser Pro Ser Ala Phe Val Val Glu Gln Ile Gly Asp Asn Tyr His Glu
50                  55                  60

Glu Pro Ile Leu Gly Phe Ser Ile Val Asn Glu Thr Gly Ala Tyr Phe
65                  70                  75                  80

Ile Pro Lys Asp Ile Ala Val Glu Ser Glu Val Phe Lys Glu Trp Val
                85                  90                  95

Glu Asn Asp Glu Gln Lys Lys Trp Val Phe Asp Ser Lys Arg Ala Val
            100                 105                 110

Val Ala Leu Arg Trp Gln Gly Ile Glu Leu Lys Gly Ala Glu Phe Asp
        115                 120                 125

Thr Leu Leu Ala Ala Tyr Ile Ile Asn Pro Gly Asn Ser Tyr Asp Asp
    130                 135                 140

Val Ala Ser Val Ala Lys Asp Tyr Gly Leu His Ile Val Ser Ser Asp
145                 150                 155                 160

Glu Ser Val Tyr Gly Lys Gly Ala Lys Arg Ala Val Pro Ser Glu Asp
                165                 170                 175

Val Leu Ser Glu His Leu Gly Arg Lys Ala Leu Ala Ile Gln Ser Leu
            180                 185                 190

Arg Glu Lys Leu Val Gln Glu Leu Glu Asn Asn Asp Gln Leu Glu Leu
```

```
            195                 200                 205
Phe Glu Glu Leu Glu Met Pro Leu Ala Leu Ile Leu Gly Glu Met Glu
    210                 215                 220

Ser Thr Gly Val Lys Val Asp Val Asp Arg Leu Lys Arg Met Gly Glu
225                 230                 235                 240

Glu Leu Gly Ala Lys Leu Lys Glu Tyr Glu Lys Ile His Glu Ile
                    245                 250                 255

Ala Gly Glu Pro Phe Asn Ile Asn Ser Pro Lys Gln Leu Gly Val Ile
                260                 265                 270

Leu Phe Glu Lys Ile Gly Leu Pro Val Val Lys Lys Thr Lys Thr Gly
        275                 280                 285

Tyr Ser Thr Ser Ala Asp Val Leu Glu Lys Leu Ala Asp Lys His Asp
    290                 295                 300

Ile Val Asp Tyr Ile Leu Gln Tyr Arg Gln Ile Gly Lys Leu Gln Ser
305                 310                 315                 320

Thr Tyr Ile Glu Gly Leu Leu Lys Val Thr Arg Pro Asp Ser His Lys
                    325                 330                 335

Val His Thr Arg Phe Asn Gln Ala Leu Thr Gln Thr Gly Arg Leu Ser
                340                 345                 350

Ser Thr Asp Pro Asn Leu Gln Asn Ile Pro Ile Arg Leu Glu Glu Gly
        355                 360                 365

Arg Lys Ile Arg Gln Ala Phe Val Pro Ser Glu Lys Asp Trp Leu Ile
    370                 375                 380

Phe Ala Ala Asp Tyr Ser Gln Ile Glu Leu Arg Val Leu Ala His Ile
385                 390                 395                 400

Ser Lys Asp Glu Asn Leu Ile Glu Ala Phe Thr Asn Asp Met Asp Ile
                    405                 410                 415

His Thr Lys Thr Ala Met Asp Val Phe His Val Ala Lys Asp Glu Val
                420                 425                 430

Thr Ser Ala Met Arg Arg Gln Ala Lys Ala Val Asn Phe Gly Ile Val
        435                 440                 445

Tyr Gly Ile Ser Asp Tyr Gly Leu Ser Gln Asn Leu Gly Ile Thr Arg
    450                 455                 460

Lys Glu Ala Gly Ala Phe Ile Asp Arg Tyr Leu Glu Ser Phe Gln Gly
465                 470                 475                 480

Val Lys Ala Tyr Met Glu Asp Ser Val Gln Glu Ala Lys Gln Lys Gly
                    485                 490                 495

Tyr Val Thr Thr Leu Met His Arg Arg Arg Tyr Ile Pro Glu Leu Thr
                500                 505                 510

Ser Arg Asn Phe Asn Ile Arg Ser Phe Ala Glu Arg Thr Ala Met Asn
        515                 520                 525

Thr Pro Ile Gln Gly Ser Ala Ala Asp Ile Ile Lys Lys Ala Met Ile
    530                 535                 540

Asp Met Ala Ala Lys Leu Lys Glu Lys Gln Leu Lys Ala Arg Leu Leu
545                 550                 555                 560

Leu Gln Val His Asp Glu Leu Ile Phe Glu Ala Pro Lys Glu Glu Ile
                    565                 570                 575

Glu Ile Leu Glu Lys Leu Val Pro Glu Val Met Glu His Ala Leu Ala
                580                 585                 590

Leu Asp Val Pro Leu Lys Val Asp Phe Ala Ser Gly Pro Ser Trp Tyr
        595                 600                 605
```

```
Asp Ala Lys
    610
```

POLYMERASES ENGINEERED TO REDUCE NUCLEOTIDE-INDEPENDENT DNA BINDING

RELATED APPLICATIONS

This application claims the benefit of U.S. patent application Ser. No. 15/581,822, filed Apr. 28, 2017, which claims the benefit of U.S. Provisional Application No. 62/444,733, filed Jan. 10, 2017, and U.S. Provisional Application No. 62/329,489, filed Apr. 29, 2016; and U.S. Provisional Application No. 62/534,871, filed Jul. 20, 2017. The disclosures of these earlier applications are hereby incorporated by reference in their entireties.

TECHNICAL FIELD

The present disclosure generally relates to the field of biotechnology. More specifically, the disclosure relates to engineered DNA polymerases having unique activity profiles, including reduced affinity for primed template nucleic acids in the absence of cognate nucleotides.

BACKGROUND

Naturally occurring DNA polymerizing enzymes are responsible for accurately replicating DNA within the cells of an organism. This process involves catalysis at the 3'-end of a growing DNA strand, whereby a free deoxyribonucleotide triphosphate (dNTP) having a base moiety matched to the base moiety on the complementary template strand is incorporated. This requirement for complementarity is utilized by sequencing technologies to analyze DNA for medical, industrial, and scientific applications.

Indeed, DNA polymerases and fragments thereof are important tools for determining identity of the next correct nucleotide (i.e., the "cognate" nucleotide) of a template nucleic acid, whether for detection of single nucleotide polymorphisms (SNPs) or more extensive sequence determination. Example applications include sequencing-by-synthesis, where cognate nucleotide identification follows nucleotide incorporation; and Sequencing By Binding™ technology, where cognate nucleotide identification is based on observations or measurements of binding events taking place prior to, or without, nucleotide incorporation.

Given the utility and advantages of Sequencing By Binding™ technology, there is an ongoing need for new and useful tools and methods that can be used for enhancing discrimination between cognate and non-cognate nucleotide in the sequencing procedure. The present disclosure addresses this need.

SUMMARY OF THE DISCLOSURE

In one aspect, the disclosure relates to an engineered DNA polymerase that includes a variant of the sequence of SEQ ID NO:3, with the variant being at least 80% identical to SEQ ID NO:3 and including an amino acid substitution mutation at one or more of positions K250, Q281, D355, Q425, and D532. According to one generally preferred embodiment, the variant is at least 90% identical to SEQ ID NO:3. Preferably, the variant is at least 95% identical to SEQ ID NO:3. More preferably, the variant is at least 98% identical to SEQ ID NO:3. According to some embodiments, when the variant is at least 90% identical to SEQ ID NO:3, the sequence of SEQ ID NO:5 can be joined to the amino terminus thereof. Alternatively, when the variant is at least 90% identical to SEQ ID NO:3, the sequence of SEQ ID NO:6 can be joined to the amino terminus thereof. According to another generally preferred embodiment, the substitution mutation at position K250 involves a mutation to a polar amino acid, the substitution mutation at position Q281 involves a mutation to an acidic amino acid, the substitution mutation at position D355 involves a mutation to a different acidic amino acid, the substitution mutation at position Q425 involves a mutation to a different polar amino acid, and the substitution mutation at position D532 involves a mutation to a different acidic amino acid. More preferably, the substitution mutation at position K250 can involve a mutation to Cys, the substitution mutation at position Q281 can involve a mutation to Glu, the substitution mutation at position D355 can involve a mutation to Glu, the substitution mutation at position Q425 can involve a mutation to Cys, and the substitution mutation at position D532 can involve a mutation to Glu. According to another generally preferred embodiment, the variant involves replacement of up to 10 amino acids of SEQ ID NO:3. Preferably, the variant includes replacement of up to 5 amino acids of SEQ ID NO:3. According to another generally preferred embodiment, the mutant DNA polymerase is present in a ternary complex that further includes a primed template nucleic acid and a cognate nucleotide or analog thereof. Preferably, the cognate nucleotide or analog thereof includes an exogenous fluorescent label. According to another generally preferred embodiment, the at least one amino acid substitution mutation is a substitution mutation at position Q281 that replaces Gln (Q) with Glu (E). According to another generally preferred embodiment, the at least one amino acid substitution mutation is a substitution mutation at position K250 that replaces Lys (K) with Cys (C), and a substitution mutation at position Q425 that replaces Gln (Q) with Cys (C). According to another generally preferred embodiment, the at least one amino acid substitution mutation is a substitution mutation at position Q281 that replaces Gln (Q) with Glu (E), a substitution mutation at position K250 that replaces Lys (K) with Cys (C), and a substitution mutation at position Q425 that replaces Gln (Q) with Cys (C). According to another generally preferred embodiment, the at least one amino acid substitution mutation is a substitution mutation at position D355 that replaces Asp (D) with Glu (E), and a substitution mutation at position Q281 that replaces Gln (Q) with Glu (E). According to another generally preferred embodiment, the at least one amino acid substitution mutation is a substitution mutation at position D355 that replaces Asp (D) with Glu (E), a substitution mutation at position K250 that replaces Lys (K) with Cys (C), and a substitution mutation at position Q425 that replaces Gln (Q) with Cys (C). According to another generally preferred embodiment, the at least one amino acid substitution mutation is a substitution mutation at position D355 that replaces Asp (D) with Glu (E), a substitution mutation at position Q281 that replaces Gln (Q) with Glu (E), a substitution mutation at position K250 that replaces Lys (K) with Cys (C), and a substitution mutation at position Q425 that replaces Gln (Q) with Cys (C). According to another generally preferred embodiment, the engineered DNA polymerase further includes an exogenous label covalently joined thereto. Preferably, the exogenous label includes a fluorescent label. According to another generally preferred embodiment, the engineered DNA polymerase includes $Mg^{2+}$-dependent phosphodiester bond forming activity. According to another generally preferred embodiment, the differential affinity of the engineered DNA polymerase for the primed template nucleic acid in the presence and absence of cognate nucleotide is greater than the differential affinity of the DNA polymerase of SEQ ID NO:4 for the primed template nucleic acid in the presence and absence of cognate nucleotide.

In another aspect, the disclosure relates to an isolated mutant DNA polymerase that includes a variant of the sequence of SEQ ID NO:2, where the variant is at least 80% identical to SEQ ID NO:2 and where the variant includes Glu (E) at position 290. According to one generally preferred embodiment, the mutant DNA polymerase further includes an N-terminal polypeptide sequence appended to the sequence of SEQ ID NO:2. Preferably, the variant sequence is a variant of SEQ ID NO:1. More preferably, the mutant DNA polymerase further includes an exogenous reporter moiety covalently joined thereto. For example, the exogenous reporter moiety can be a fluorescent reporter moiety. Preferably, the fluorescent reporter moiety does not substantially change excitation or emission properties following contact with any nucleotide. According to another generally preferred embodiment, the mutant DNA polymerase can be bound to a primed template nucleic acid molecule in combination with a nucleotide that is the next correct nucleotide for the primed template nucleic acid molecule. According to another generally preferred embodiment, the mutant DNA polymerase can bind to a blocked primed template nucleic acid molecule in combination with a nucleotide that is the next correct nucleotide for the blocked primed template nucleic acid molecule. When this is the case, the blocked primed template nucleic acid molecule can include a reversible terminator moiety on the 3' terminal nucleotide of the primer strand.

In another aspect, the disclosure relates to an isolated mutant DNA polymerase that includes a variant of the sequence of SEQ ID NO:2, where the variant is at least 80% identical to SEQ ID NO:2 and where the variant includes Cys (C) at position 259, and Cys (C) at position 434. According to one generally preferred embodiment, the mutant DNA polymerase can further include an N-terminal polypeptide sequence appended to the variant of SEQ ID NO:2. Preferably, the variant sequence is a variant of SEQ ID NO:1. According to another generally preferred embodiment, the mutant DNA polymerase further includes an exogenous reporter moiety covalently joined thereto. For example, the exogenous reporter moiety can be a fluorescent reporter moiety. When this is the case, the fluorescent reporter moiety does not substantially change excitation or emission properties following contact with any nucleotide. According to another generally preferred embodiment, the mutant DNA polymerase is bound to a primed template nucleic acid molecule in combination with a nucleotide that is the next correct nucleotide for the primed template nucleic acid molecule. According to another generally preferred embodiment, the mutant DNA polymerase binds to a blocked primed template nucleic acid molecule in combination with a nucleotide that is the next correct nucleotide for the blocked primed template nucleic acid molecule. Preferably, the blocked primed template nucleic acid molecule includes a reversible terminator moiety on the 3' terminal nucleotide of the primer strand.

In another aspect, the disclosure relates to an isolated mutant DNA polymerase that includes a variant of the sequence of SEQ ID NO:2, where the variant is at least 80% identical to SEQ ID NO:2 and where the variant includes Glu (E) at position 290, Cys (C) at position 259, and Cys (C) at position 434. According to one generally preferred embodiment, the mutant DNA polymerase further includes an N-terminal polypeptide sequence appended to the variant of the sequence of SEQ ID NO:2. Preferably, the variant sequence is a variant of SEQ ID NO:1. According to another generally preferred embodiment, the mutant DNA polymerase further includes an exogenous reporter moiety covalently joined thereto. Preferably, the exogenous reporter moiety is a fluorescent reporter moiety. More preferably, the fluorescent reporter moiety does not substantially change excitation or emission properties following contact with any nucleotide. According to another generally preferred embodiment, the mutant DNA polymerase is bound to a primed template nucleic acid molecule in combination with a nucleotide that is the next correct nucleotide for the primed template nucleic acid molecule. According to another generally preferred embodiment, the mutant DNA polymerase binds to a blocked primed template nucleic acid molecule in combination with a nucleotide that is the next correct nucleotide for the blocked primed template nucleic acid molecule. Preferably, the blocked primed template nucleic acid molecule includes a reversible terminator moiety on the 3' terminal nucleotide of the primer strand.

In another aspect, the disclosure relates to an isolated mutant DNA polymerase that includes a variant of the sequence of SEQ ID NO:2, where the variant is at least 80% identical to SEQ ID NO:2 and where the variant includes Glu (E) at position 364, and further includes Glu (E) at position 290. According to one generally preferred embodiment, the mutant DNA polymerase further includes an N-terminal polypeptide sequence appended to the variant of the sequence of SEQ ID NO:2. Preferably, the variant sequence is a variant of SEQ ID NO:1. More preferably, the mutant DNA polymerase further includes an exogenous reporter moiety covalently joined thereto. For example, the exogenous reporter moiety can be a fluorescent reporter moiety. More preferably, the fluorescent reporter moiety does not substantially change excitation or emission properties following contact with any nucleotide. According to another generally preferred embodiment, the mutant DNA polymerase is bound to a primed template nucleic acid molecule in combination with a nucleotide that is the next correct nucleotide for the primed template nucleic acid molecule. According to another generally preferred embodiment, the mutant DNA polymerase binds to a blocked primed template nucleic acid molecule in combination with a nucleotide that is the next correct nucleotide for the blocked primed template nucleic acid molecule. Preferably, the blocked primed template nucleic acid molecule includes a reversible terminator moiety on the 3' terminal nucleotide of the primer strand.

In another aspect, the disclosure relates to an isolated mutant DNA polymerase that includes a variant of the sequence of SEQ ID NO:2, where the variant is at least 80% identical to SEQ ID NO:2 and where the variant includes Glu (E) at position 364, and further includes Cys (C) at position 259 and Cys (C) at position 434. According to one generally preferred embodiment, the mutant DNA polymerase further includes an N-terminal polypeptide sequence appended to the variant of the sequence of SEQ ID NO:2. Preferably, the variant sequence is a variant of SEQ ID NO:1. More preferably, the mutant DNA polymerase further includes an exogenous reporter moiety covalently joined thereto. For example, the exogenous reporter moiety can be a fluorescent reporter moiety. Preferably, the fluorescent reporter moiety does not substantially change excitation or emission properties following contact with any nucleotide. According to another generally preferred embodiment, the mutant DNA polymerase is bound to a primed template nucleic acid molecule in combination with a nucleotide that is the next correct nucleotide for the primed template nucleic acid molecule. According to another generally preferred embodiment, the mutant DNA polymerase binds to a blocked primed template nucleic acid molecule in combination with a nucleotide that is the next correct nucleotide for the blocked primed template nucleic acid molecule. Preferably, the blocked primed template nucleic acid molecule includes a reversible terminator moiety on the 3' terminal nucleotide of the primer strand.

In another aspect, the disclosure relates to an isolated mutant DNA polymerase that includes a variant of the sequence of SEQ ID NO:2, where the variant is at least 80% identical to SEQ ID NO:2 and where the variant includes Glu (E) at position 364, and further includes Glu (E) at position 290, Cys (C) at position 259, and Cys (C) at position 434. According to one generally preferred embodiment, the mutant DNA polymerase further includes an N-terminal polypeptide sequence appended to the variant of the sequence of SEQ ID NO:2. Preferably, the variant sequence is a variant of SEQ ID NO:1. More preferably, the mutant DNA polymerase further includes an exogenous reporter moiety covalently joined thereto. For example, the exogenous reporter moiety can be a fluorescent reporter moiety. More preferably, the fluorescent reporter moiety does not substantially change excitation or emission properties following contact with any nucleotide. According to another generally preferred embodiment, the mutant DNA polymerase is bound to a primed template nucleic acid molecule in combination with a nucleotide that is the next correct nucleotide for the primed template nucleic acid molecule. According to another generally preferred embodiment, the mutant DNA polymerase binds to a blocked primed template nucleic acid molecule in combination with a nucleotide that is the next correct nucleotide for the blocked primed template nucleic acid molecule. Preferably, the blocked primed template nucleic acid molecule includes a reversible terminator moiety on the 3' terminal nucleotide of the primer strand.

In another aspect, the disclosure relates to a reaction mixture. The reaction mixture includes a DNA polymerase that can be any of: (i) an engineered DNA polymerase that includes a variant of the sequence of SEQ ID NO:3, the variant being at least 80% identical to SEQ ID NO:3 and including an amino acid substitution mutation at one or more of positions K250, Q281, D355, Q425, and D532; (ii) an engineered DNA polymerase that includes a variant of the sequence of SEQ ID NO:2, the variant being at least 80% identical to SEQ ID NO:2 and wherein the variant includes Glu (E) at position 290; (iii) an engineered DNA polymerase that includes a variant of the sequence of SEQ ID NO:2, the variant being at least 80% identical to SEQ ID NO:2 and wherein the variant includes Cys (C) at position 259, and Cys (C) at position 434; and (iv) an engineered DNA polymerase that includes a variant of the sequence of SEQ ID NO:2, the variant being at least 80% identical to SEQ ID NO:2 and wherein the variant includes Glu (E) at position 290, Cys (C) at position 259, and Cys (C) at position 434. Further included in the reaction mixture are a primed template nucleic acid molecule, optionally including a reversible terminator nucleotide at a 3'-end thereof; and at least one nucleotide. According to one generally preferred embodiment, the primed template nucleic acid molecule does not include the optional reversible terminator nucleotide, and the reaction mixture further includes a cation that stabilizes a ternary complex. The ternary complex includes (a) the primed template nucleic acid molecule, (b) the DNA polymerase, and (c) one of the at least one nucleotide that is the next correct nucleotide for the primed template nucleic acid molecule. Preferably, the cation that stabilizes ternary complexes is any of a divalent metal cation, and a trivalent metal cation. According to another generally preferred embodiment, the DNA polymerase includes an exogenous detectable label. Preferably, the exogenous detectable label is a fluorescent label that does not substantially change its excitation or emission properties after binding any nucleotide. According to another generally preferred embodiment, one or more of the at least one nucleotide includes an exogenous label.

In another aspect, the disclosure relates to a kit for identifying the cognate nucleotide for a primed template nucleic acid molecule. The kit includes a DNA polymerase that can be any of: (i) an engineered DNA polymerase that includes a variant of the sequence of SEQ ID NO:3, the variant being at least 80% identical to SEQ ID NO:3 and including an amino acid substitution mutation at one or more of positions K250, Q281, D355, Q425, and D532; (ii) an engineered DNA polymerase that includes a variant of the sequence of SEQ ID NO:2, the variant being at least 80% identical to SEQ ID NO:2 and wherein the variant includes Glu (E) at position 290; (iii) an engineered DNA polymerase that includes a variant of the sequence of SEQ ID NO:2, the variant being at least 80% identical to SEQ ID NO:2 and wherein the variant includes Cys (C) at position 259, and Cys (C) at position 434; and (iv) an engineered DNA polymerase that includes a variant of the sequence of SEQ ID NO:2, the variant being at least 80% identical to SEQ ID NO:2 and wherein the variant includes Glu (E) at position 290, Cys (C) at position 259, and Cys (C) at position 434. The kit further includes a plurality of nucleotides or analogs thereof, and a plurality of reversible terminator nucleotides. According to one generally preferred embodiment, the primed template nucleic acid includes a blocked primer. According to another generally preferred embodiment, the primed template nucleic acid includes an extendable primer. According to another generally preferred embodiment, the DNA polymerase includes a reporter moiety attached thereto. According to another generally preferred embodiment, the plurality of nucleotides or analogs thereof includes a plurality of dNTPs or analogs thereof. Preferably, the plurality of reversible terminator nucleotides includes a plurality of non-fluorescent reversible terminator nucleotides. More preferably, the plurality of non-fluorescent reversible terminator nucleotides is a plurality of unlabeled reversible terminator nucleotides. According to another generally preferred embodiment, the kit further includes a second polymerase that incorporates the plurality of reversible terminator nucleotides into the primed template nucleic acid molecule. According to another generally preferred embodiment, one or more of the plurality of nucleotides or analogs thereof includes an exogenous label.

BRIEF DESCRIPTION OF THE DRAWINGS

FIG. 1A shows results from procedures carried out in the presence of 50 mM KCl and 320 mM potassium glutamate. FIG. 1B shows results from procedures carried out in the presence of 100 mM KCl and 320 mM potassium glutamate. FIG. 1C shows results from procedures carried out in the presence of 150 mM KCl and 320 mM potassium glutamate.

FIG. 2A shows results from procedures carried out in the presence of 50 mM KCl and 320 mM potassium glutamate. FIG. 2B shows results from procedures carried out in the presence of 100 mM KCl and 320 mM potassium glutamate. FIG. 2C shows results from procedures carried out in the presence of 150 mM KCl and 320 mM potassium glutamate.

FIG. 3A shows results from procedures carried out using an examination buffer that included 100 mM KCl. FIG. 3B shows results from procedures carried out using an examination buffer that included 200 mM KCl. FIG. 3C shows results from procedures carried out using an examination buffer that included 400 mM KCl.

DEFINITIONS

Figure 1A:
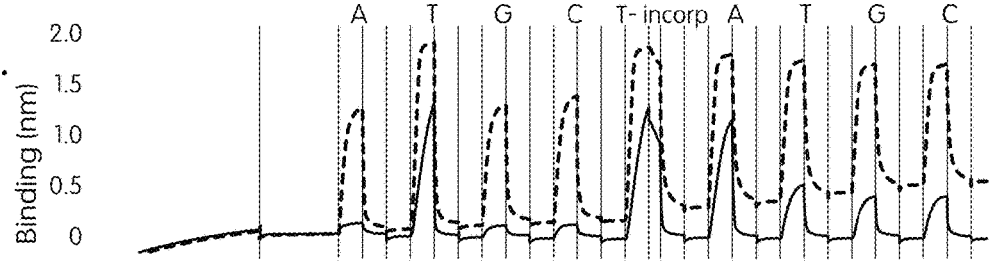
FIGS. 1A-1C are interferometry traces for single-nucleotide examinations, and incorporation steps; comparing results obtained using the CBT and TQE polymerases under different salt conditions.

Unless defined otherwise, all technical and scientific terms used herein have the same meaning as is commonly understood by one of ordinary skill in the art. For clarity, the following specific terms have the specified meanings. Other terms are defined in other sections herein.

The singular forms "a" "an" and "the" include plural referents unless the context clearly dictates otherwise. Approximating language, as used in the description and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the compositions, apparatus, or methods of the present disclosure. At the very least, each numerical parameter should at least be construed in light of the number of reported significant digits and by applying ordinary rounding techniques.

As used herein, "Sequencing By Binding™" refers to a sequencing technique wherein specific binding of a polymerase to a primed template nucleic acid is used for identifying the next correct nucleotide to be incorporated into the primer strand of the primed template nucleic acid. The specific binding interaction precedes chemical incorporation of the nucleotide into the primer strand, and so identification of the next correct nucleotide can take place either without or before incorporation of the next correct nucleotide.

As used herein, "nucleic acid" or "oligonucleotide" or "polynucleotide" or grammatical equivalents used herein means at least two nucleotides covalently linked together. Thus, a "nucleic acid" is a polynucleotide, such as DNA, RNA, or any combination thereof, that can be acted upon by a polymerizing enzyme during nucleic acid synthesis. The term "nucleic acid" includes single-, double-, or multiple-stranded DNA, RNA and analogs (derivatives) thereof. Double-stranded nucleic acids advantageously can minimize secondary structures that may hinder nucleic acid synthesis. A double stranded nucleic acid may possess a nick or a single-stranded gap.

As used herein, the "next correct nucleotide" (sometimes referred to as the "cognate" nucleotide) is the nucleotide having a base complementary to the base of the next template nucleotide. The next correct nucleotide will hybridize at the 3'-end of a primer to complement the next template nucleotide. The next correct nucleotide can be, but need not necessarily be, capable of being incorporated at the 3' end of the primer. For example, the next correct nucleotide can be a member of a ternary complex that will complete an incorporation reaction or, alternatively, the next correct nucleotide can be a member of a stabilized ternary complex that does not catalyze an incorporation reaction. The next correct nucleotide can be a nucleotide analog. A nucleotide having a base that is not complementary to the next template base is referred to as an "incorrect" (or "non-cognate") nucleotide. The next correct nucleotide, when participating in a ternary complex, is non-covalently bound to the primed template nucleic acid of the ternary complex.

As used herein, the "next template nucleotide" (or the "next template base") refers to the next nucleotide (or base) in a template nucleic acid that pairs with a position that is located immediately downstream of the 3'-end of a hybridized primer. In other words, the next template nucleotide is located immediately 5' of the base in the template that is hybridized to the 3' end of the primer.

As used herein, a "template nucleic acid" is a nucleic acid to be acted upon (e.g., amplified, detected or sequenced) using a method or composition disclosed herein.

As used herein, a "primed template nucleic acid" (or alternatively, "primed template nucleic acid molecule") is a template nucleic acid primed with (i.e., hybridized to) a primer, wherein the primer is an oligonucleotide having a 3'-end with a sequence complementary to a portion of the template nucleic acid. The primer can optionally have a free 5'-end (e.g., the primer being noncovalently associated with the template) or the primer can be continuous with the template (e.g., via a hairpin structure). The primed template nucleic acid includes the complementary primer and the template nucleic acid to which it is bound. Unless explicitly stated, the primer of the primed template nucleic acid can have either a 3'-end that is extendible by a polymerase, or a 3'-end that is blocked from extension.

As used herein, a "blocked primed template nucleic acid" (or alternatively, "blocked primed template nucleic acid molecule") is a primed template nucleic acid modified to preclude or prevent phosphodiester bond formation at the 3'-end of the primer. Blocking may be accomplished, for example, by chemical modification with a blocking group at either the 3' or 2' position of the five-carbon sugar at the 3' terminus of the primer. Alternatively, or in addition, chemical modifications that preclude or prevent phosphodiester bond formation may also be made to the nitrogenous base of a nucleotide. Reversible terminator nucleotide analogs including each of these types of blocking groups will be familiar to those having an ordinary level of skill in the art. Incorporation of these analogs at the 3' terminus of a primer of a primed template nucleic acid molecule results in a blocked primed template nucleic acid molecule. The blocked primed template nucleic acid includes the complementary primer, blocked from extension at its 3'-end, and the template nucleic acid to which it is bound.

As used herein, a "nucleotide" is a molecule that includes a nitrogenous base, a five-carbon sugar (ribose or deoxyribose), and at least one phosphate group. The term embraces, but is not limited to, ribonucleotides, deoxyribonucleotides, nucleotides modified to include exogenous labels or reversible terminators, and nucleotide analogs.

As used herein, a "native" nucleotide refers to a naturally occurring nucleotide that does not include an exogenous label (e.g., a fluorescent dye, or other label) or chemical modification such as may characterize a nucleotide analog. Examples of native nucleotides useful for carrying out the Sequencing By Binding™ procedures described herein include: dATP (2'-deoxyadenosine-5'-triphosphate); dGTP (2'-deoxyguanosine-5'-triphosphate); dCTP (2'-deoxycytidine-5'-triphosphate); dTTP (2'-deoxythymidine-5'-triphosphate); and dUTP (2'-deoxyuridine-5'-triphosphate).

As used herein, a "nucleotide analog" has one or more modifications, such as chemical moieties, which replace, remove and/or modify any of the components (e.g., nitrogenous base, five-carbon sugar, or phosphate group(s)) of a native nucleotide. Nucleotide analogs may be either incorporable or non-incorporable by a polymerase in a nucleic acid polymerization reaction. Optionally, the 3'-OH group of a nucleotide analog is modified with a moiety. The moiety may be a reversible or irreversible terminator of polymerase extension. The base of a nucleotide may be any of adenine, cytosine, guanine, thymine, or uracil, or analogs thereof. Optionally, a nucleotide has an inosine, xanthine, hypoxanthine, isocytosine, isoguanine, nitropyrrole (including 3-nitropyrrole) or nitroindole (including 5-nitroindole) base. Nucleotides may include, but are not limited to, ATP, UTP, CTP, GTP, ADP, UDP, CDP, GDP, AMP, UMP, CMP, GMP, dATP, dTTP, dUTP, dCTP, dGTP, dADP, dTDP, dCDP, dGDP, dAMP, dTMP, dCMP, and dGMP. Nucleotides may also contain terminating inhibitors of DNA polymerase, dideoxynucleotides or 2',3' dideoxynucleotides, which are abbreviated as ddNTPs (ddGTP, ddATP, ddTTP, ddUTP and ddCTP).

As used herein, a "blocking moiety," when used with reference to a nucleotide analog, is a part of the nucleotide that inhibits or prevents the nucleotide from forming a covalent linkage to a second nucleotide (e.g., via the 3'-OH of a primer nucleotide) during the incorporation step of a nucleic acid polymerization reaction. The blocking moiety of a "reversible terminator" nucleotide can be modified or removed from the nucleotide analog to allow for nucleotide incorporation. Such a blocking moiety is referred to herein as a "reversible terminator moiety." Exemplary reversible terminator moieties are set forth in U.S. Pat. Nos. 7,427,673; 7,414,116; and 7,057,026 and PCT publications WO 91/06678 and WO 07/123744, each of which is incorporated by reference.

As used herein, a "test nucleotide" is a nucleotide being investigated for its ability to participate in formation of a ternary complex that further includes a primed template nucleic acid and a polymerase.

As used herein, "polymerase" is a generic term for a nucleic acid synthesizing enzyme, including but not limited to, DNA polymerase, RNA polymerase, reverse transcriptase, primase and transferase. Typically, the polymerase includes one or more active sites at which nucleotide binding and/or catalysis of nucleotide polymerization may occur. The polymerase may catalyze the polymerization of nucleotides to the 3'-end of a primer bound to its complementary nucleic acid strand. For example, a polymerase can catalyze the addition of a next correct nucleotide to the 3' oxygen of the primer via a phosphodiester bond, thereby chemically incorporating the nucleotide into the primer. Optionally, the polymerase used in the provided methods is a processive polymerase. Optionally, the polymerase used in the provided methods is a distributive polymerase. Optionally, a polymerase need not be capable of nucleotide incorporation under one or more conditions used in a method set forth herein. For example, a mutant polymerase may be capable of forming a ternary complex but incapable of catalyzing nucleotide incorporation.

As used herein, a "variant" of a polypeptide reference sequence is a form or version of the polypeptide sequence that differs in some respect. Variants can differ in amino acid sequence and can include, for example, amino acid substitutions, additions (e.g., insertions, and extensions of termini), and deletions. A variant of a polypeptide reference sequence can include amino acid substitutions and/or internal additions and/or deletions and/or additional amino acids at one or both termini of the reference sequence.

As used herein, a "polyhistidine-tag motif" is an amino acid motif in proteins that consists of six or more contiguous histidine residues, and that facilitates binding of the proteins to an affinity support (e.g., bead or resin) containing bound divalent nickel ions.

As used herein, a "salt providing monovalent cation" is an ionic compound that dissociates in aqueous solution to produce cations having a single positive charge. For example, the cations can be metal cations where the oxidation state is +1.

As used herein, "a glutamate salt" is an ionic compound that dissociates in aqueous solution to produce glutamate anions.

As used herein, "biphasic" refers to a two-stage process wherein a primed template nucleic acid is contacted with a polymerase and a test nucleotide. The first phase of the process involves contacting the primed template nucleic acid with a polymerase in the presence of a sub-saturating level of nucleotide(s), or even in the absence of nucleotides. The term "sub-saturating," when used in reference to ligand that binds to a receptor (e.g., a nucleotide that binds to a polymerase), refers to a concentration of the ligand that is below that required to result in at least 90% of the receptors being bound to the ligand at equilibrium. For example, a sub-saturating amount of nucleotide can yield at least 90%, 95%, 99% or more polymerases being bound to the nucleotide. The second phase of the process involves contacting the primed template nucleic acid from the first phase with a polymerase in the presence of a higher concentration of nucleotide(s) than used in the first phase, where the higher concentration is sufficient to yield maximal ternary complex formation when a nucleotide in the reaction is the next correct nucleotide.

As used herein, "providing" a template, a primer, a primed template nucleic acid, or a blocked primed template nucleic acid refers to the delivery of one or many nucleic acid polymers, for example to a reaction mixture or reaction chamber. Optionally, providing a material can include preparation of the material in addition to its delivery.

As used herein, "monitoring" (or sometimes "measuring") refers to a process of detecting a measurable interaction or binding between two molecular species. For example, monitoring may involve detecting measurable interactions between a polymerase and primed template nucleic acid, typically at various points throughout a procedure. Monitoring can be intermittent (e.g., periodic) or continuous (e.g., without interruption), and can involve acquisition of quantitative results. Monitoring can be carried out by detecting multiple signals over a period of time during a binding event or, alternatively, by detecting signal(s) at a single time point during or after a binding event.

As used herein, "contacting" refers to the mixing together of reagents (e.g., mixing an immobilized template nucleic acid and either a buffered solution that includes a polymerase, or the combination of a polymerase and a test nucleotide) so that a physical binding reaction or a chemical reaction may take place.

As used herein, "incorporating" or "chemically incorporating," when used in reference to a primed template and nucleotide, refers to the process of joining a cognate nucleotide to a primer by formation of a phosphodiester bond.

As used herein, "extension" refers to the process after an oligonucleotide primer and a template nucleic acid have annealed to one another, wherein a polymerase enzyme catalyzes addition of one or more nucleotides at the 3'-end of the primer. A nucleotide that is added to a nucleic acid by extension is said to be "incorporated" into the nucleic acid. Accordingly, the term "incorporating" can be used to refer to the process of joining a nucleotide to the 3'-end of a primer by formation of a phosphodiester bond.

As used herein, a "binary complex" is an intermolecular association between a polymerase and a primed template nucleic acid (e.g., blocked primed template nucleic acid), where the complex does not include a nucleotide molecule such as the next correct nucleotide.

As used herein, a "ternary complex" is an intermolecular association between a polymerase, a primed template nucleic acid (e.g., blocked primed template nucleic acid), and the next correct nucleotide molecule positioned immediately downstream of the primer and complementary to the template strand of the primed template nucleic acid or the blocked primed template nucleic acid. The primed template nucleic acid can include, for example, a primer with a free 3'-OH or a blocked primer (e.g., a primer with a chemical modification on the base or the sugar moiety of the 3' terminal nucleotide, where the modification precludes enzymatic phosphodiester bond formation). The term "stabilized ternary complex" means a ternary complex having promoted or prolonged existence or a ternary complex for which disruption has been inhibited. Generally, stabilization of the ternary complex prevents covalent incorporation of the nucleotide component of the ternary complex into the primed nucleic acid component of the ternary complex.

As used herein, a "catalytic metal ion" refers to a metal ion that facilitates phosphodiester bond formation between the 3'-OH of a nucleic acid (e.g., a primer) and the phosphate of an incoming nucleotide by a polymerase. A "divalent catalytic metal cation" is a catalytic metal ion having a valence of two. Catalytic metal ions can be present at sufficiently low concentrations to stabilize formation of a complex between a polymerase, a nucleotide, and a primed template nucleic acid, referred to as non-catalytic concentrations of a metal ion. Catalytic concentrations of a metal ion refer to the amount of a metal ion sufficient for polymerases to catalyze the reaction between the 3'-OH group of a nucleic acid (e.g., a primer) and the phosphate group of an incoming nucleotide.

As used herein, a "non-catalytic metal ion" refers to a metal ion that, when in the presence of a polymerase enzyme, does not facilitate phosphodiester bond formation needed for chemical incorporation of a nucleotide into a primer. Typically, the non-catalytic metal ion is a cation. A non-catalytic metal ion may inhibit phosphodiester bond formation by a polymerase, and so may stabilize a ternary complex by preventing nucleotide incorporation. Non-catalytic metal ions may interact with polymerases, for example, via competitive binding compared to catalytic metal ions. A "divalent non-catalytic metal ion" is a non-catalytic metal ion having a valence of two. Examples of divalent non-catalytic metal ions include, but are not limited to, $Ca^{2+}$, $Zn^{2+}$, $Ni^{2+}$, and $Sr^{2+}$. The trivalent $Eu^{3+}$ and $Tb^{3+}$ ions are non-catalytic metal ions having a valence of three.

As used herein an "exogenous label" refers to a detectable chemical moiety that has been added to another entity, such as a nucleotide, polymerase (e.g., a DNA polymerase) or other sequencing reagent set forth herein. While a native dNTP may have a characteristic limited fluorescence profile, the native dNTP does not include any added colorimetric or fluorescent moiety. Conversely, a dATP (2'-deoxyadenosine-5'-triphosphate) molecule modified to include a chemical linker and fluorescent moiety attached to the gamma phosphate would be said to include an exogenous label because the attached chemical components are not ordinarily a part of the nucleotide. Of course, chemical modifications to add detectable labels to nucleotide bases also would be considered exogenous labels. Likewise, a DNA polymerase modified to include a conformationally sensitive fluorescent dye that changes its properties upon nucleotide binding also would be said to include an exogenous label because the label is not ordinarily a part of the polymerase.

As used herein, "unlabeled" refers to a molecular species free of added or exogenous label(s) or tag(s). Of course, unlabeled nucleotides will not include either of an exogenous fluorescent label, or an exogenous Raman scattering tag. A native nucleotide is another example of an unlabeled molecular species. An unlabeled molecular species can exclude one or more of the labels set forth herein or otherwise known in the art relevant to nucleic acid sequencing or analytical biochemistry.

As used herein, the term "solid support" refers to a rigid substrate that is insoluble in aqueous liquid. The substrate can be non-porous or porous. The substrate can optionally be capable of taking up a liquid (e.g., due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers.

As used herein, a "flow cell" is a reaction chamber that includes one or more channels that direct fluid in a predetermined manner to conduct a desired reaction. The flow cell can be coupled to a detector such that a reaction occurring in the reaction chamber can be observed. For example, a flow cell can contain primed template nucleic acid molecules, for example, tethered to a solid support, to which nucleotides and ancillary reagents are iteratively applied and washed away. The flow cell can include a transparent material that permits the sample to be imaged after a desired reaction occurs. For example, a flow cell can include a glass or plastic slide containing small fluidic channels through which polymerases, dNTPs and buffers can be pumped. The glass or plastic inside the channels can be decorated with one or more primed template nucleic acid molecules to be sequenced. An external imaging system can be positioned to detect the molecules on the surface of the glass or plastic. Reagent exchange in a flow cell is accomplished by pumping, drawing, or otherwise "flowing" different liquid reagents through the flow cell. Exemplary flow cells, methods for their manufacture and methods for their use are described in US Pat. App. Publ. Nos. 2010/0111768 A1 or 2012-0270305 A1; or WO 05/065814, each of which is incorporated by reference herein.

As used herein, a "reaction vessel" is a container that isolates one reaction (e.g., a binding reaction; an incorporation reaction; etc.) from another, or that provides a space in which a reaction can take place. Non-limiting examples of reaction vessels useful in connection with the disclosed technique include: flow cells, wells of a multiwell plate; microscope slides; tubes (e.g., capillary tubes); etc. Features to be monitored during binding and/or incorporation reactions can be contained within the reaction vessel.

As used herein, a "kit" is a packaged unit containing one or more components that can be used for performing detection and/or sequencing reactions using an engineered DNA polymerase, as disclosed herein. Typical kits may include packaged combinations, in one or more containers or vials, of reagents to be used in the procedure.

DETAILED DESCRIPTION

Introduction and Overview

The Sequencing By Binding™ method disclosed by Vijayan et al., in published U.S. patent application publication number 2017/0022553A1 benefits from reduced polymerase binding to primed template nucleic acid in the absence of cognate nucleotide (e.g., whether in the absence of any nucleotide, or in the presence of only non-cognate nucleotide). Different approaches have proven useful for reducing the magnitude of this binary complex formation, while at the same time stabilizing ternary complexes that include primed template nucleic acid, polymerase, and the cognate nucleotide. For example, some approaches rely on manipulation of salt concentrations or the manner of delivering polymerase to the primed template to enhance this discrimination.

Polymerases that exhibit reduced nucleotide-independent interaction with DNA templates would be useful tools in Sequencing By Binding™ procedures. This is particularly true when labeled polymerase interaction with a primed template nucleic acid is monitored as a surrogate for cognate nucleotide identification. Binary complex formation confounds identification of cognate nucleotide when signal due to cognate nucleotide identification is not substantially greater than signal due to polymerase binding in the presence of non-cognate nucleotide (i.e., conditions of weak discrimination). Below there are described engineered DNA polymerases that are useful for enhancing detection of cognate nucleotides by reducing signals associated with polymerase binding in the absence of cognate nucleotide. The engineered polymerases can have other uses as will be recognized by those skilled in the art in view of the teaching set forth herein.

DESCRIPTION OF VARIOUS EMBODIMENTS

Described below are the preparation of DNA polymerase I (pol I) large fragment mutants from a thermostable family strain of *Bacillus stearothermophilus* (Bst-f), and from *Bacillus subtilis* (Bsu-f), where the mutants form ternary complexes with cognate nucleotides while exhibiting reduced DNA-binding affinity in dynamic equilibrium binding assays. Both of the Bst-f and Bsu-f enzymes are family A polymerases having homology to other well-characterized, high fidelity polymerases, including *E. coli* DNA pol I (KF), and *T. aquaticus* DNA pol I (Taq). These polymerases share certain conserved protein sequence motifs, but are distinguished by certain non-conserved regions.

The parent enzyme ("CBT") used for preparing certain reduced DNA affinity polymerases was an engineered version of the Bst polymerase. The polypeptide sequence of the CBT enzyme had been modified with respect to cysteine content, and by addition of N-terminal sequences that facilitated protein purification and processing. More specifically, the polypeptide sequence identified as SEQ ID NO:1 included a modified N-terminus having: (1) an engineered polyhistidine-tag motif at positions 5-10; (2) a thrombin cleavage site between positions Arg17 and Gly18; and (3) a cysteine residue at position 23. The naturally occurring Bst polymerase sequence extended from position 27 to the C-terminus (subject to replacement of naturally occurring cysteine residues). It is to be understood that engineered polymerases in accordance with the disclosure optionally include or omit the N-terminal modifications that do not substantially affect DNA affinity of the polymerase. For example, useful polymerases can be constructed on a parent scaffold of SEQ ID NO:2 (i.e., the polypeptide sequence of SEQ ID NO:1 following thrombin cleavage) or SEQ ID NO:3 (i.e., the protein expression product of the cysteine-substituted Bst-f polymerase). Examples of variant polypeptide sequences relative to each of these scaffolds are presented in Table 1. Nucleic acid modifications used to encode the reduced DNA affinity polymerases were prepared using site-directed mutagenesis and prokaryotic expression cloning vectors that will be familiar to those having an ordinary level of skill in the art.

The *Bacillus* DNA polymerase large fragment (i.e., the C-terminal fragment commonly used in crystal structure analysis; and lacking 5'-3' exonuclease activity) of SEQ ID NO:4 served as the scaffold for construction of the engineered polymerases derived from the CBT constructs, as disclosed herein. The engineered CBT polymerase of SEQ ID NO:3 differs from the sequence of the wild type *Bacillus* polymerase large fragment of SEQ ID NO:4 by substitution of two Cys residues (i.e., at positions 90 and 547) by Ala residues. The sequence of the Cys-substituted polymerase of SEQ ID NO:2 differs from the engineered polymerase of SEQ ID NO:3 by further including an amino-terminal sequence of amino acids given by SEQ ID NO:5. Likewise, the sequence of the N-terminal modified and Cys-substituted polymerase of SEQ ID NO:1 differs from the engineered polymerase of SEQ ID NO:3 by further including an amino-terminal sequence of amino acids given by SEQ ID NO:6. Since the N-terminal modifications employed in preparation of the engineered DNA polymerases described herein (i.e., SEQ ID NO:5 and SEQ ID NO:6) are not known to affect enzymatic activities, useful engineered DNA polymerases can be described in the context of the base scaffold of SEQ ID NO:3.

The parent enzyme ("CBU") used for preparing another specificity-enhanced polymerase was an engineered version of the Bsu polymerase. The polypeptide sequence of the CBU enzyme had been modified with respect to cysteine content, and N-terminal sequences that facilitated protein purification and processing. More specifically, the polypeptide sequence identified as SEQ ID NO:13 included a modified N-terminus having: (1) an engineered polyhistidine tag motif at positions 5-10; (2) a thrombin cleavage site between positions Arg17 and Gly18; and (3) a cysteine residue at position 23. The naturally occurring Bsu polymerase sequence extended from position 27 to the C-terminus. It is to be understood that engineered polymerases in accordance with the disclosure optionally include or omit the N-terminal modifications that do not substantially affect DNA affinity of the polymerase. For example, useful polymerases can be constructed on a parent scaffold of SEQ ID NO:12 (i.e., essentially the polypeptide sequence of SEQ ID NO:13 following thrombin cleavage). Variant polypeptide sequences corresponding to useful specificity-enhanced polymerases (e.g., "UQE" mutant polymerases) relative to each of these scaffolds are presented in Table 1. Nucleic acid modifications used to encode the UQE polymerase were prepared using site-directed mutagenesis and prokaryotic expression cloning vectors that will be familiar to those having an ordinary level of skill in the art.

Sequence Comparison, Identity, and Homology

The term "identical," in the context of two or more nucleic acid or polypeptide sequences, refers to two or more sequences or subsequences that are the same, when compared and aligned for maximum correspondence, as measured using one of the sequence comparison algorithms described below (or other algorithms available to persons of skill) or by visual inspection. The term "percent identity," in the context of two or more nucleic acid or polypeptide sequences, refers to two or more sequences or subsequences that have a specified percentage of amino acid residues or nucleotides that are the same, when compared and aligned for maximum correspondence, as measured using one of the sequence comparison algorithms described below (or other algorithms available to persons of skill) or by visual inspection. By convention, amino acid additions, substitutions, and deletions within an aligned reference sequence are all differences that reduce the percent identity in an equivalent manner. Additional amino acids present at the N- or C-terminus of a polynucleotide compared to the reference have no effect on percent identity scoring for aligned regions. For example, alignment of a 105 amino acid long polypeptide to a reference sequence 100 amino acids long would have a 100% identity score if the reference sequence fully was contained within the longer polynucleotide with no amino acid differences. A single amino acid difference (addition, deletion or substitution) between the two sequences within the 100-amino acid span of the aligned reference sequence would mean the two sequences were 99% identical.

The phrase "substantially identical," in the context of two nucleic acids or polypeptides (e.g., DNAs encoding a polymerase, or the amino acid sequence of a polymerase) refers to two or more sequences or subsequences that have at least about 60%, about 80%, about 90-95%, about 98%, about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity over 50, 100, 150 or more residues is routinely used to establish homology. Higher levels of sequence similarity, e.g., 30%, 40%, 50%, 60%, 70%, 80%, 90%, 95%, or 99% or more, can also be used to establish homology. Methods for determining sequence similarity percentages (e.g., BLASTP and BLASTN using default parameters) are described herein and are generally available.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Current Protocols in Molecular Biology, Ausubel et al., eds., Current Protocols, a joint venture between Greene Publishing Associates, Inc. and John Wiley & Sons, Inc., supplemented through 2004).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Substitution or replacement of one amino acid for another (i.e., so-called "substitution mutations") can be used for modifying functional properties of engineered DNA polymerases. In certain embodiments, a substitution mutation comprises a mutation to a residue having a nonpolar side chain. Amino acids having nonpolar side chains are well known in the art and include, for example: glycine (Gly or G), alanine (Ala or A), valine (Val or V), leucine (Leu or L), isoleucine (Ile or I), methionine (Met or M), phenylalanine (Phe or F), tryptophan (Trp or W), and proline (Pro or P). In certain embodiments, a substitution mutation comprises a mutation to a residue having a polar side chain. Amino acids having polar side chains are well known in the art and include, for example: serine (Ser or S), threonine (Thr or T), cysteine (Cys or C), tyrosine (Tyr or Y), asparagine (Asn or N), and glutamine (Gln or Q). In certain embodiments, a substitution mutation comprises a mutation to a residue having an acidic side chain. Amino acids having acidic side chains are well known in the art and include, for example: aspartate (Asp or D) and glutamate (Glu or E). In certain embodiments, a substitution mutation comprises a mutation to a residue having a basic side chain. Amino acids having basic side chains are well known in the art and include, for example: lysine (Lys or K), arginine (Arg or R), and histidine (His or H).

A summary of primary amino acid sequence features of polymerases used in the procedures disclosed below are presented in Table 1.

TABLE 1

Summary of Key Amino Acid Substitutions

| Mutant Name | Feature | Position |
| --- | --- | --- |
| CBT | Cys-substituted Bst enzyme with N-terminal modifications<br>Cys-substituted Bst enzyme Engineered Bst (Cys removed) | SEQ ID NO: 1<br>SEQ ID NO: 2<br>SEQ ID NO: 3 |
| TDE | Crippled polymerase does not catalyze $Mg^{2+}$-dependent incorporation | D to E at 381 of SEQ ID NO: 1; or<br>D to E at 364 of SEQ ID NO: 2; or<br>D to E at 355 of SEQ ID NO: 3 |
| BDE | Crippled polymerase does not catalyze $Mg^{2+}$-dependent incorporation | D to E at 558 of SEQ ID NO: 1 or<br>D to E at 541 of SEQ ID NO: 2 or<br>D to E at 532 of SEQ ID NO: 3 |
| TQE | Polymerase that discriminates between binary and ternary complexes under lower salt conditions, and exhibits reduced DNA binding absent cognate nucleotide | Q to E at 307 of SEQ ID NO: 1 or<br>Q to E at 290 of SEQ ID NO: 2 or<br>Q to E at 281 of SEQ ID NO: 3 |
| DSA | Polymerase that discriminates between binary and ternary complexes under lower salt conditions, and exhibits reduced DNA binding absent cognate nucleotide | K to C at 276 of SEQ ID NO: 1; and<br>Q to C at 451 of SEQ ID NO: 1<br>K to C at 259 of SEQ ID NO: 2; and<br>Q to C at 434 of SEQ ID NO: 2<br>K to C at 250 of SEQ ID NO: 3; and<br>Q to C at 425 of SEQ ID NO: 3 |
| TEE | Combination of TQE and DSA modifications; exhibits somewhat improved discrimination relative to DSA | Q to E at 307 of SEQ ID NO: 1; and<br>K to C at 276 of SEQ ID NO: 1; and<br>Q to C at 451 of SEQ ID NO: 1<br>Q to E at 290 of SEQ ID NO: 2; and<br>K to C at 259 of SEQ ID NO: 2; and<br>Q to C at 434 of SEQ ID NO: 2<br>Q to E at 281 of SEQ ID NO: 3; and<br>K to C at 250 of SEQ ID NO: 3; and<br>Q to C at 425 of SEQ ID NO: 3 |

TABLE 1-continued

Summary of Key Amino Acid Substitutions

| Mutant Name | Feature | Position |
|---|---|---|
| DEA | Combination of TDE and TQE modifications; crippled DNA polymerase does not catalyze Mg²⁺-dependent incorporation; exhibits reduced DNA binding absent cognate nucleotide | D to E at 381 of SEQ ID NO: 1<br>Q to E at 307 of SEQ ID NO: 1<br>D to E at 364 of SEQ ID NO: 2<br>Q to E at 290 of SEQ ID NO: 2<br>D to E at 355 of SEQ ID NO: 3<br>Q to E at 281 of SEQ ID NO: 3 |
| TSA | Combination of TDE and DSA modifications; crippled DNA polymerase does not catalyze Mg²⁺-dependent incorporation; discriminates under low salt conditions | D to E at 381 of SEQ ID NO: 1<br>K to C at 276 of SEQ ID NO: 1; and<br>Q to C at 451 of SEQ ID NO: 1<br>D to E at 364 of SEQ ID NO: 2<br>K to C at 259 of SEQ ID NO: 2; and<br>Q to C at 434 of SEQ ID NO: 2<br>D to E at 355 of SEQ ID NO: 3<br>K to C at 250 of SEQ ID NO: 3; and<br>Q to C at 425 of SEQ ID NO: 3 |
| TRI | Combination of TDE, TQE, and DSA modifications; crippled DNA polymerase does not catalyze Mg²⁺-dependent incorporation; exhibits reduced DNA binding absent cognate nucleotide; discriminates under low salt conditions | D to E at 381 of SEQ ID NO: 1<br>Q to E at 307 of SEQ ID NO: 1<br>K to C at 276 of SEQ ID NO: 1; and<br>Q to C at 451 of SEQ ID NO: 1<br>D to E at 364 of SEQ ID NO: 2<br>Q to E at 290 of SEQ ID NO: 2<br>K to C at 259 of SEQ ID NO: 2; and<br>Q to C at 434 of SEQ ID NO: 2<br>D to E at 355 of SEQ ID NO: 3<br>Q to E at 281 of SEQ ID NO: 3<br>K to C at 250 of SEQ ID NO: 3; and<br>Q to C at 425 of SEQ ID NO: 3 |
| CBU | Cys-substituted Bsu enzyme with N-terminal modifications | N/A |
| UQE | Q to E | 288 of SEQ ID NO: 12; or<br>314 of SEQ ID NO: 13 |

Engineered Polymerases Incorporating Combinations of Mutated Positions

Combinations of mutated positions within the disclosed scaffolds of SEQ ID NOS:1-3 are embraced by the present disclosure, and can, for example, be used in connection with Sequencing By Binding™ protocols. More specifically, the engineered polynucleotide sequence of SEQ ID NO:3 optionally can further include one or more N-terminal amino acids, and the resulting polypeptide can further include at least one changed amino acid at a corresponding position in the sequence of SEQ ID NO:3. For example, polypeptides having the amino acid sequences of SEQ ID NO:2 and SEQ ID NO:1 (each of which fully contains the sequence of SEQ ID NO:3) can be used in Sequencing By Binding™ protocols, and optionally can include amino acid substitutions or replacements at the corresponding position of SEQ ID NO:3. For clarity, the last position of SEQ ID NO:3 (a Lys residue at position 578) corresponds to the last position of each of SEQ ID NO:1 (position 604) and SEQ ID NO:2 (position 587). Thus, the sequences of SEQ ID Nos:1-3 all align with each other.

Several exemplary positions within the disclosed engineered polypeptide scaffolds of SEQ ID Nos:1-3 are disclosed herein. Other positions optionally can be changed, and still fall within the scope of the disclosure. Preferably, at least one and up to 10 amino acids within the sequence of SEQ ID NO:3 (including the sequence found within the sequences of SEQ ID NOs:1-2) are substituted or replaced by different amino acids. Illustrative positions within the polypeptide sequence of SEQ ID NO:3 that can be substituted to provide desired activity include position numbers: 250, 281, 355, 425, and 532. In particularly preferred embodiments, all different combinations of these positions optionally can be mutated or replaced (e.g., in combinations of 2, 3, 4, or even all 5 substitutions). Illustrative embodiments of these combinations are disclosed herein. Combinations of up to 10 substituted positions are preferred and embraced by the disclosure. However, it will be understood that a variant of a sequence set forth herein can include more than 10 substitutions, and are within the scope of the present disclosure.

All combinations of the amino acid replacements disclosed herein (e.g., enumerated in Table 1) fall within the scope of the disclosure, and apply to the polypeptide scaffolds of each of SEQ ID Nos:1-3 (i.e., where a replacement in the sequence of SEQ ID NO:3 translates to the scaffolds of SEQ ID NO:1-2, by the correspondence set forth in Table 1). In the context of the scaffold of SEQ ID NO:3, unique combinations of two amino acid replacements are found among the following permutations: D to E at 355 in combination with any of: D to E at 532, Q to E at 281, K to C at 250, or Q to C at 425; D to E at 532 in combination with any of: Q to E at 281, K to C at 250, or Q to C at 425; Q to C at 281 in combination with any of: K to C at 250, or Q to C at 425; or K to C at 250 in combination with Q to C at 425. Unique combinations of three amino acid replacements are found among the following permutations: the combination of D to E at 355, and D to E at 532 in further combination with any of: Q to E at 281, K to C at 250, or Q to C at 425; the combination of D to E at 532, and Q to E at 281 in further combination with any of: D to E at 355, K to C at 250, or Q to C at 425; the combination of Q to E at 281, and K to C at 250 in further combination with any of: D to E at 355, D to E at 532, or Q to C at 425; the combination of K to C at 250, Q to C at 425 in further combination with any of: D to E at 355, D to E at 532, or Q to E at 281; the combination of D to E at 355 and Q to E at 281 in further combination with any of: D to E at 532, K to C at 250, or Q to C at 425;

the combination of D to E at 355 and K to C at 250 in further combination with any of: D to E at 532, Q to E at 281, or Q to C at 425; the combination of D to E at 355 and Q to C at 425 in further combination with any of: D to E at 532, Q to E at 281, or K to C at 250; the combination of D to E at 532 and K to C at 250 in further combination with any of: D to E at 355, Q to E at 281, or Q to C at 425; the combination of D to E at 532 and Q to C at 425 in further combination with any of: D to E at 355, Q to E at 281, or K to C at 250; or the combination of Q to E at 281 and Q to C at 425 in further combination with any of: D to E at 355, D to E at 532, or K to C at 250. Unique combinations of four amino acid replacements are found among the following permutations: the combination of D to E at 355, D to E at 532, Q to E at 281 in further combination with any of: K to C at 250, or Q to C at 425; the combination of D to E at 532, Q to E at 281, K to C at 250 in further combination with any of: D to E at 355, or Q to C at 425; the combination of Q to E at 281, K to C at 250, and Q to C at 425 in further combination with any of: D to E at 355, or D to E at 532; the combination of D to E at 355, Q to E at 281, and K to C at 250 in further combination with any of: D to E at 532, or Q to C at 425; the combination of D to E at 355, Q to E at 281, and Q to C at 425 in further combination with any of: D to E at 532, or K to C at 250; the combination of D to E at 355, D to E at 532, and K to C at 250 in further combination with any of: Q to E at 281, or Q to C at 425; or the combination of D to E at 355, D to E at 532, and Q to C at 425 in further combination with any of: Q to E at 281, or K to C at 250. The combination of all five amino acid replacements is represented by D to E at 355, D to E at 532, Q to E at 281, K to C at 250, and Q to C at 425. Each unique combination of amino acid replacements in the scaffold of SEQ ID NO:3, or the scaffold of SEQ ID NO:1 or SEQ ID NO:2 which contain the sequence of SEQ ID NO:3 are embraced by the present disclosure.

Polymerases exhibiting advantageous features include: (1) those classified as "crippled" DNA polymerases; and/or (2) polymerases exhibiting reduced affinity for primed template nucleic acids in the absence of cognate nucleotide, and an ability to discriminate between cognate and non-cognate nucleotides under low salt conditions. Each of these features can sort independently (e.g., combination mutants can possess more than one of these features). Interestingly, the independent mutations characteristic of the TQE and DSA polymerases affected substantially the same activities (i.e., low salt discriminatory capability, and reduced DNA binding) of the polymerase. Engineered DNA polymerases lacking the capacity to promote $Mg^{2+}$-dependent incorporation of cognate nucleotides into primed template nucleic acids (i.e., so-called "crippled" DNA polymerases) also are disclosed in commonly assigned U.S. patent application Ser. No. 15/581,822, published as US 2017/030135 A1, the disclosure of which is incorporated by reference herein in its entirety. The present disclosure particularly embraces engineered DNA polymerases comprising amino acid replacement or substitution mutations of these crippled DNA polymerases in combination with each other, and in combination with other replacement or substitution mutations disclosed herein. Likewise, combinations of different substitution mutations leading to reduced affinity of polymerase for primed template nucleic acid in the absence of cognate nucleotide can be combined with each other, or with other replacement or substitution mutations, such as those described herein.

Useful Recombinant DNA and Protein Expression Techniques

Conventional recombinant DNA cloning techniques can be used to prepare constructs for transformation or transfection ("transformation" hereafter) and expression of nucleic acids encoding engineered polymerases in accordance with the disclosure. Nucleic acid constructs encoding polymerase fragments were used in combination with synthetic oligonucleotides, standard PCR techniques, and vector ligation to introduce the site-directed mutations needed to produce the polynucleotide sequences disclosed herein. The different constructs were ligated into a plasmid expression vector, and the plasmid construct introduced into an *E. coli* host using standard transformation techniques. Preferred expression vectors include a T7 promoter sequence upstream of the polymerase-encoding insert, where the T7 promoter is inducible by IPTG or by co-expression of a T7 RNA polymerase. Expressed proteins included a polyhistidine-tag motif that facilitated binding of the recombinant protein to a nickel-based resin column as part of the purification process.

Embraced by the present description are nucleic acid molecules encoding altered polymerase enzymes. In accordance with various embodiments, a defined nucleic acid includes not only the identical nucleic acid but also any minor base variations including, in particular, substitutions in cases which result in a synonymous codon (a different codon specifying the same amino acid residue) due to the degenerate code in conservative amino acid substitutions. The term "nucleic acid sequence" can also include the complementary sequence to any single stranded sequence given regarding base variations. Nucleic acid molecules encoding the engineered DNA polymerases described herein may also be included in a suitable expression vector to express the polymerase proteins encoded therefrom in a suitable host. Such an expression vector includes a vector having a nucleic acid according to the embodiments presented herein operably linked to regulatory sequences, such as promoter regions, that are capable of effecting expression of said DNA fragments. The term "operably linked" refers to a juxtaposition wherein the components described are in a relationship permitting them to function in their intended manner. Such vectors may be transformed into a suitable host cell to provide for the expression of a recombinant protein. Regulatory elements required for expression include promoter sequences to bind RNA polymerase and to direct an appropriate level of transcription initiation and also translation initiation sequences for ribosome binding. For example, a bacterial expression vector may include a promoter such as the lac promoter and for translation initiation the Shine-Dalgarno sequence and AUG start codon. Similarly, a eukaryotic expression vector may include a heterologous or homologous promoter for RNA polymerase II, a downstream polyadenylation signal, the start codon AUG, and a termination codon for detachment of the ribosome. Such vectors may be obtained commercially or be assembled from the sequences well known in the art.

Covered nucleic acid molecules may encode a mature protein or a protein having a prosequence, including that encoding a leader sequence on the preprotein which is then cleaved by the host cell to form a mature protein. The vectors may be, for example, plasmid, virus or phage vectors provided with an origin of replication, and optionally a promoter for the expression of said nucleotide and optionally a regulator of the promoter. The vectors may contain one or more selectable markers, such as, for example, an antibiotic resistance gene.

Recombinant polymerase proteins can be, and indeed were, further purified and concentrated using conventional laboratory techniques that will be familiar to those having an ordinary level of skill in the art. Purified polymerase samples were stored at −80° C. until being used.

Accordingly, the present disclosure provides a nucleic acid construct encoding one or more of the protein sequences set forth herein. In particular embodiments, the nucleic acid construct is a plasmid or vector. The nucleic acid construct can include elements that allow replication of the construct, biological selection for the construct and/or expression of the one or more proteins encoded by the construct. Suitable vector backbones include, for example, those routinely used in the art such as plasmids, artificial chromosomes, BACs, or PACs. Numerous vectors and expression systems are commercially available from such corporations as Novagen (Madison, Wis.), Clonetech (Pal Alto, Calif.), Stratagene (La Jolla, Calif.), and ThermoFisher (Waltham, Mass.). Vectors typically contain one or more regulatory regions. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns.

The present disclosure also provides recombinant organisms that include a nucleic acid construct that encodes one or more of the protein sequences set forth herein. A recombinant organism of the present disclosure can be configured to express one or more polymerase having a sequence set forth herein. Furthermore, the present disclosure provides a recombinant organism that comprises a polymerase having a sequence set forth herein.

In another embodiment, a cultured cell is provided that is transformed or transfected ("transformed" hereafter) with a vector comprising a nucleic acid construct described herein. In this regard, a cell is successfully transformed with a vector when the transcription machinery of the intact cell has access to the nucleic acid template for the production of mRNA. Protocols to facilitate transformation of vectors into cells are well known in the art. Also provided herein are the progeny of a cultured cell that was stably transformed with the vector as described above. Such progeny will contain copies of the vector without having undergone the transformation protocol and are capable of transcribing the nucleic acids contained in vector under the control of an expression control sequence. Techniques utilizing cultured cells transformed with expression vectors to produce quantities of polypeptides are well known in the art.

Useful Polymerase Labeling and Processing Techniques

Depending on the application, engineered polymerases according to the disclosure may be either labeled with a detectable label, or unlabeled. Unlabeled polymerases may be used in label-free systems, or alternatively can be used in conjunction with detectably labeled nucleotides and/or template nucleic acids. Detectably labeled polymerases can be used in combination with unlabeled nucleotides, or unlabeled primer or template nucleic acids for cognate nucleotide identification. Of course, the engineered polymerases may simply be used for synthesizing DNA strands in template-dependent DNA synthesis reactions.

Engineered polymerases can be covalently modified, post-purification, to contain a fluorescent moiety. For example, a fluorescent moiety can be joined to the free sulfhydryl of a Cys residue located toward the N-terminal ends of a protein. To demonstrate the technique, a Cy-5 fluorescent label chemically activated as a maleimide ester was joined to the free thiol functional group of the N-terminal region Cys residue using standard protein labeling techniques. While use of labeled engineered polymerases was demonstrated using a fluorescent label, many other types of labels also may be used. Moreover, other attachment chemistries can be used as well.

Alternative labels may be used for labeling engineered polymerases in accordance with the disclosure. Labels attached to the polymerases can be detectable by changes in any of: refractive index, charge detection, Raman scattering detection, ellipsometry detection, pH detection, size detection, mass detection, surface plasmon resonance, guided mode resonance, nanopore optical interferometry, whispering gallery mode resonance, nanoparticle scattering, photonic crystal, quartz crystal microbalance, bio-layer interferometry, vibrational detection, pressure detection and other label free detection schemes that detect the added mass or refractive index due to polymerase binding in a closed-complex with a template nucleic acid, and the like. Further examples of useful labels are set forth in sections below.

Polymerases in accordance with the disclosure can be subjected to further post-purification processing to enhance functional properties or modify structure. This can involve chemical modification and/or enzymatic processing. Optionally, a portion of the engineered polymerase is cleaved from the remainder of the polypeptide, and removed.

During performance of a Sequencing By Binding™ procedure, the engineered polymerase used to identify cognate nucleotide optionally can be used for incorporating the same or a different type of nucleotide. For example, in some embodiments it is preferable to remove labeled polymerase and nucleotide following an examination step, and then to replace that first polymerase and nucleotide with the same or different nucleotide and a different polymerase. Optionally, the replaced nucleotide can be a reversible terminator nucleotide (e.g., an unlabeled reversible terminator nucleotide).

Allele-Specific Capture Using Engineered Polymerases: General Aspects

Engineered DNA polymerases in accordance with the disclosure can be used to perform allele-specific capture of target nucleic acids, for example as described in commonly owned U.S. patent application identified by Ser. No. 15/701, 358 and its priority provisional application having Ser. No. 62/448,730, the entire disclosures of which are incorporated by reference herein. More particularly, engineered DNA polymerases can be used for selecting or capturing nucleic acids having target alleles of interest. For example, a stabilized ternary complex can be formed between a polymerase, target allele and cognate nucleotide for the allele. Polymerase specificity allows a target allele to be separated from other nucleic acids, including for example, other alleles that differ from the target allele by a single nucleotide.

In one embodiment, a method for separating a target allele from a mixture of nucleic acids includes the step of (a) providing a mixture of nucleic acids in fluidic contact with a stabilized ternary complex that is attached to a solid support. The stabilized ternary complex includes an engineered polymerase, a primed nucleic acid template, and a next correct nucleotide. The template includes a target allele, where the next correct nucleotide is a cognate nucleotide for the target allele. The stabilized ternary complex can be attached to the solid support via a linkage between the polymerase and the solid support, or via a linkage between the next correct nucleotide and the solid support. There also is the step of (b) separating the solid support from the mixture of nucleic acids, thereby separating the target allele from the mixture of nucleic acids.

In another embodiment, a method for separating a plurality of target alleles from a mixture of nucleic acids includes the step of (a) providing a mixture of nucleic acids in fluidic contact with a plurality of stabilized ternary complexes that are solid support-attached. The stabilized ternary complexes each include an engineered polymerase, a primed nucleic acid template, and a next correct nucleotide. The template includes a target allele, and the next correct nucleotide is a cognate nucleotide for the target allele. Each of the stabilized ternary complexes can be attached to the solid support via a linkage between the polymerase and the solid support, or via a linkage between the next correct nucleotide and the solid support. There also is the step of (b) separating the solid support from the mixture of nucleic acids, thereby separating the target alleles from the mixture of nucleic acids.

In another embodiment, a method for separating a first allele of a locus from a second allele at the locus includes the step of (a) providing a mixture including the second allele in fluidic contact with a stabilized ternary complex that is attached to a solid support. The stabilized ternary complex includes an engineered polymerase, a primer hybridized to a nucleic acid template, and a next correct nucleotide. The template includes the first allele. The next correct nucleotide is a cognate nucleotide for the first allele, or the 3'-end of the primer includes a cognate nucleotide for the first allele. The stabilized ternary complex can be attached to the solid support via a linkage between the polymerase and the solid support, or via a linkage between the next correct nucleotide and the solid support. There also is the step of (b) separating the solid support from the mixture of nucleic acids, thereby separating the first allele from the second allele.

In another embodiment, a method for separating first alleles at a plurality of loci from second alleles at the plurality of loci, respectively, includes the step of (a) providing a mixture of the second alleles at the plurality of loci, respectively, in fluidic contact with a plurality of stabilized ternary complexes that are solid support-attached. The stabilized ternary complexes each include an engineered DNA polymerase, a primed nucleic acid template, and a next correct nucleotide. The template includes a first allele, where the next correct nucleotide is a cognate nucleotide for the first allele, or the 3'-end of the primer includes a cognate nucleotide for the first allele. Each of the stabilized ternary complexes is attached to the solid support via a linkage between the polymerase and the solid support, or via a linkage between the next correct nucleotide and the solid support. There also is the step of (b) separating the solid support from the mixture of nucleic acids, thereby separating the first alleles from the second alleles at the plurality of loci.

Genotyping Using Engineered Polymerases: General Aspects

Engineered DNA polymerases in accordance with the disclosure can be used to perform genotyping by polymerase binding, for example as described in commonly owned U.S. patent application identified by Ser. No. 15/701,373 and its priority provisional application having Ser. No. 62/448,630, the entire disclosures of which are incorporated by reference herein. For example, a ternary complex can be formed between an engineered DNA polymerase, a primed template encoding a target single nucleotide polymorphism (SNP) allele and a cognate nucleotide for the SNP allele. Detection of the ternary complex will result in selective detection of the SNP allele, compared to a non-target SNP allele at the same locus, because the cognate nucleotide is selective for the target SNP when forming a ternary complex with the polymerase.

In one embodiment, a method for identifying target alleles in a mixture of nucleic acids includes the step of (a) providing an array of features, where different locus-specific primers are attached at different features of the array. There also is the step of (b) contacting the array with a plurality of nucleic acid templates, engineered DNA polymerases and nucleotides to form a plurality of stabilized ternary complexes at a plurality of the features. The stabilized ternary complexes each include an engineered DNA polymerase, a template nucleic acid including a target allele of a locus, a locus-specific primer of the array hybridized to the locus, and a next correct nucleotide that is a cognate to the target allele. There also is the step of (c) detecting stabilized ternary complexes at the features, thereby identifying the target alleles.

In another embodiment, a method for identifying target alleles in a mixture of nucleic acids includes the step of (a) providing an array of features, where different allele-specific primers are attached at different features of the array. There also is the step of (b) contacting the array with a plurality of nucleic acid templates, engineered DNA polymerases and nucleotides to form a plurality of stabilized ternary complexes at a plurality of the features. The stabilized ternary complexes each include an engineered DNA polymerase, a template nucleic acid including a target allele of a locus, an allele-specific primer of the array hybridized to the locus, and a next correct nucleotide having a cognate in the locus. The 3'-end of the allele-specific primer includes a cognate nucleotide for the target allele. There also is the step of (c) detecting stabilized ternary complexes at the features, thereby identifying the target alleles.

In another embodiment, a method for identifying target alleles in a mixture of nucleic acids includes the step of (a) providing an array of features, where different locus-specific primers are attached at a first subset of the features of the array, and where different allele-specific primers are attached at a second subset of the features of the array. There also is the step of (b) contacting the array with a plurality of nucleic acid templates, engineered DNA polymerases and nucleotides to form a plurality of stabilized ternary complexes at a plurality of the features. The stabilized ternary complexes at the first subset of features each include an engineered DNA polymerase, a template nucleic acid including a target allele of a locus, a locus-specific primer of the array hybridized to the locus, and a next correct nucleotide that is a cognate to the target allele. The stabilized ternary complexes at the second subset of features each includes an engineered DNA polymerase, a template nucleic acid including a target allele of a locus, an allele-specific primer of the array hybridized to the locus, and a next correct nucleotide having a cognate in the locus. The 3'-end of the allele-specific primer includes a cognate nucleotide for the target allele. There also is the step of (c) detecting stabilized ternary complexes at the features, thereby identifying the target alleles.

In another embodiment, a method for identifying target alleles in a mixture of nucleic acids includes the step of (a) providing an array of features, where different template nucleic acids are attached at different features of the array. There also is the step of (b) contacting the array with a plurality of primers, engineered DNA polymerases and nucleotides to form a plurality of stabilized ternary complexes at a plurality of the features. The stabilized ternary complexes at the features each include an engineered DNA polymerase, a template nucleic acid attached to a feature of the array and including a target allele of a locus, a primer hybridized to the locus, and a next correct nucleotide having a cognate in the locus, where either: (i) the primer is an allele-specific primer including a 3' nucleotide that is a cognate nucleotide for the target allele, or (ii) the primer is a locus-specific primer and the next correct nucleotide hybridizes to the target allele. There further is the step of (c) detecting stabilized ternary complexes at the features, thereby identifying the target alleles.

In another embodiment, a method for identifying target alleles in a mixture of nucleic acids includes the step of (a) providing an array of features, where engineered DNA polymerases are attached at features of the array. There also is the step of (b) contacting the array with a plurality of primers, template nucleic acids and nucleotides to form a plurality of stabilized ternary complexes at a plurality of the features. The stabilized ternary complexes at the features each include an engineered DNA polymerase that is attached at a feature of the array, a template nucleic acid including a target allele of a locus, a primer hybridized to the locus, and a next correct nucleotide having a cognate in the locus, where either: (i) the primer is an allele-specific primer including a 3' nucleotide that is a cognate nucleotide for the target allele, or (ii) the primer is a locus-specific primer and the next correct nucleotide hybridizes to the target allele. There also is the step of (c) detecting stabilized ternary complexes at the features, thereby identifying the target alleles.

Sequencing by Binding™ Methods Using Engineered Polymerases: General Aspects

Described herein are polymerase-based nucleic acid Sequencing By Binding™ reactions, wherein the polymerase undergoes transitions between open and closed conformations during discrete steps of the reaction. In one step, the polymerase binds to a primed template nucleic acid to form a binary complex, also referred to herein as the pre-insertion conformation. In a subsequent step, an incoming nucleotide is bound and the polymerase fingers close, forming a pre-chemistry conformation comprising the polymerase, primed template nucleic acid and nucleotide; wherein the bound nucleotide has not been incorporated. This step may be followed by a $Mg^{2+}$- or $Mn^{2+}$-catalyzed chemical incorporation of the next correct nucleotide, wherein nucleophilic displacement of a pyrophosphate (PPi) by the 3'-hydroxyl of the primer results in phosphodiester bond formation. This is generally referred to as nucleotide "incorporation." The polymerase returns to an open state upon the release of PPi following nucleotide incorporation, and translocation initiates the next round of reaction. Certain details of the Sequencing By Binding™ procedure can be found in commonly owned U.S. patent applications identified by Ser. No. 14/805,381 (now published as US Pat. App. Pub. No. US 2017/0022553 A1) and 62/375,379, the entire disclosures of these documents being incorporated by reference herein for all purposes.

While a ternary complex including a primed template nucleic acid molecule having a primer with a free 3'-hydroxyl can form in the absence of a divalent catalytic metal ion (e.g., $Mg^{2+}$), chemical addition of nucleotide can proceed in the presence of the divalent metal ions. Low or deficient levels of catalytic metal ions, such as $Mg^{2+}$ tend to lead to non-covalent (physical) sequestration of the next correct nucleotide in a tight ternary complex. This ternary complex may be referred to as a stabilized or trapped ternary complex. Other methods disclosed herein also can be used to produce a stabilized ternary complex. In any reaction step described above, the polymerase configuration and/or interaction with a nucleic acid may be monitored during an examination step to identify the next correct base in the nucleic acid sequence. Before or after incorporation, reaction conditions can be changed to disengage the polymerase from the primed template nucleic acid, and changed again to remove from the local environment any reagents that inhibit polymerase binding.

Generally speaking, the Sequencing By Binding™ procedure includes an "examination" step that identifies the next template base, and optionally a subsequent "incorporation" step that adds one or more complementary nucleotides to the 3'-end of the primer component of the primed template nucleic acid. Identity of the next correct nucleotide to be added is determined either without, or before chemical linkage of that nucleotide to the 3'-end of the primer through a covalent bond. The examination step can involve providing a primed template nucleic acid to be used in the procedure, and contacting the primed template nucleic acid with a polymerase enzyme (e.g., a DNA polymerase) composition and one or more test nucleotides being investigated as the possible next correct nucleotide. Further, there is a step that involves monitoring or measuring the interaction between the polymerase and the primed template nucleic acid in the presence of the test nucleotides.

Optionally, monitoring of the interaction can take place when the primer of the primed template nucleic acid molecule includes a blocking group that precludes enzymatic incorporation of an incoming nucleotide into the primer. The interaction additionally or alternatively can take place in the presence of stabilizers (e.g., non-catalytic metal ions that inhibit incorporation), whereby the polymerase-nucleic acid interaction is stabilized in the presence of the next correct nucleotide (i.e., stabilizers that stabilize the ternary complex). Again, the examination step identifies or determines the identity of the next correct nucleotide without requiring incorporation of that nucleotide. Stated differently, identity of the next correct nucleotide can be established without chemical incorporation of the nucleotide into the primer, whether or not the 3'-end of the primer is blocked.

Whereas methods involving a single template nucleic acid molecule may be described for convenience, these methods are exemplary. The sequencing methods provided herein readily encompass a plurality of template nucleic acids, wherein the plurality of nucleic acids may be clonally amplified copies of a single nucleic acid, or disparate nucleic acids, including combinations, such as populations of disparate nucleic acids that are clonally amplified.

The Examination Step

Generally, an examination step in a Sequencing By Binding™ procedure in accordance with the disclosed technique typically includes the following sub-steps: (1) providing a primed template nucleic acid molecule (i.e., a template nucleic acid molecule hybridized with a primer that optionally may be blocked from extension at its 3'-end); (2) contacting the primed template nucleic acid molecule with a reaction mixture that includes at least one polymerase that can be distinguished from others used in the procedure (e.g., by virtue of including a detectable label, or by timing of delivery to a primed template nucleic acid molecule) and one nucleotide; (3) detecting the interaction of the polymerase with the primed template nucleic acid molecule in the presence of the nucleotide and without chemical incorporation of any nucleotide into the primed template nucleic acid; and (4) determining from the detected interaction the identity of the next base in the template nucleic acid (i.e., the complement of the next correct nucleotide).

In one embodiment, an examination step includes: (1) serially contacting a primed template nucleic acid (where the primer strand optionally is blocked from extension at its 3'-end) with a plurality of distinguishably labeled polymerase-nucleotide combinations under conditions that discriminate between formation of ternary complexes and binary complexes; (2) detecting any ternary complexes that formed as a result of the serial contacting steps by detecting one or more of the distinguishably labeled polymerases from the combinations used in the different contacting steps; and (3) identifying the next correct nucleotide for the primed template nucleic acid as the nucleotide component of the distinguishably labeled polymerase-nucleotide combination that formed the ternary complex. While a ternary complex may be stabilized by non-catalytic cations that inhibit nucleotide incorporation or polymerization, primers blocked at their 3'-ends provide alternative stabilization approaches. In some embodiments, a trivalent lanthanide cation or other stabilizing agent (e.g., a divalent metal ion that inhibits incorporation, of a trivalent metal ion that inhibits incorporation) may be used to inhibit dissociation of the complex (e.g., to "lock" the ternary complex in place). Optionally, a detectably labeled polymerase is delivered to an immobilized primed template nucleic acid molecule in a flow cell in combination with a single nucleotide to assess whether or not the nucleotide is the next correct nucleotide to be incorporated. Optionally, an incorporation step follows the examination step that identifies the next correct nucleotide.

In a different embodiment that takes advantage of single-scan imaging to process a population of primed template nucleic acid molecules, an examination step includes: (1) providing the population; (2) serially performing a plurality of contacting steps (e.g., four contacting steps), one after the other, that involve contacting the population with different reagent solutions, where each reagent solution contains a distinguishable polymerase (e.g., being distinguishable from the others by virtue of a detectable label) and a different nucleotide in the presence of a ternary complex-stabilizing agent; (3) imaging the population after performance of at least two, and preferably after performance of all four contacting steps to detect labels associated with the different distinguishable polymerase compositions, thereby determining which members of the population participate in ternary complexes independently containing the different polymerases; and (4) determining identities of cognate nucleotides for different members of the population from the imaging results. More particularly, the determining step optionally may involve identifying cognate nucleotides by assessing which polymerase(s) participated in a ternary complex for a particular member of the population. When multiple imaging steps conveniently can be performed, imaging and detection can take place after each contacting step has concluded. Notably, the serial contacting steps can be carried out in a serial fashion so that the different polymerase and nucleotide combinations do not mix prior to formation of their respective ternary complexes. Thus, the polymerase and nucleotide (as a combination, unassociated with primed template nucleic acid) from one step should not mingle or mix with the polymerase and nucleotide (as a combination, unassociated with primed template nucleic acid) from a subsequent step. More particularly, free (i.e., non-complexed) polymerase from a prior contacting step preferably do not mingle with (i.e., are not simultaneously present with) a nucleotide type that is first introduced in a subsequent contacting step. Conversely, it is acceptable to mix a free (i.e., non-complexed) nucleotide type from a prior contacting step with a polymerase used in a subsequent contacting step.

The primer of the primed template nucleic acid optionally can be either an extendible primer, or a primer blocked from extension at its 3'-end (e.g., by the presence of a reversible terminator moiety). The primed template nucleic acid, the polymerase and the test nucleotide are capable of forming a ternary complex when the base of the test nucleotide is complementary to the next base of the primed template nucleic acid molecule. The primed template nucleic acid and the polymerase are capable of forming a binary complex when the base of the test nucleotide is not complementary to the next base of the primed template nucleic acid molecule. Optionally, the contacting occurs under conditions that favor formation of the ternary complex over formation of the binary complex. Optionally, the conditions that favor or stabilize the ternary complex are provided by either: (1) the presence of a reversible terminator moiety on the 3' nucleotide of the primer of the primed template nucleic acid molecule; or (2) the presence of a non-catalytic ion (e.g., a divalent or trivalent non-catalytic metal ion) that inhibits nucleotide incorporation or polymerization. Optionally, the conditions that disfavor or destabilize binary complexes are provided by the presence of one or more monovalent cations and/or glutamate anions in the reaction mixture during the examination step. Alternatively or in addition to using these conditions, a polymerase engineered to have reduced catalytic activity or reduced propensity for binary complex formation can be used. The determining or identifying step can include identifying the base of the nucleotide that is complementary to the next base of the primed template nucleic acid. This can be accomplished by detecting the polymerase of the ternary complex (e.g., via a label attached to the polymerase), and deducing identity of the cognate nucleotide from that identification.

The examination step conventionally is controlled so that nucleotide incorporation is attenuated. This being the case, a separate incorporation step (discussed elsewhere herein in greater detail) may be performed. The separate incorporation step may be accomplished without the need for monitoring, as the base has already been identified during the examination step. However if desired, subsequent incorporation can be detected, for example by incorporating nucleotides having exogenous labels. Detection at both binding and incorporation steps can provide for error checking and increased sequencing accuracy. A reversibly terminated nucleotide (whether labeled or not) may be used in the incorporation step to prevent the addition of more than one nucleotide during a single cycle.

The Sequencing By Binding™ method allows for controlled determination of a template nucleic acid base (e.g., by identifying a next correct nucleotide) without the need for labeled nucleotides, as the interaction between the polymerase and template nucleic acid can be monitored without a label on the nucleotide. Template nucleic acid molecules may be sequenced under examination conditions which do not require attachment of template nucleic acid or polymerase to a solid support. However, in certain preferred embodiments, primed template nucleic acids to be sequenced are attached to a solid support, such as an interior surface of a flow cell. The compositions, methods and systems described herein provide numerous advantages over previous systems, such as controlled reaction conditions, unambiguous determination of sequence, long read lengths, low overall cost of reagents, and low instrument cost. Accordingly, in some embodiments, a polymerase having a sequence set forth herein can form a stabilized ternary complex on a solid support via binding to a primed template nucleic acid that is attached to the solid support.

Alternatively or in addition to attaching primed template nucleic acids to a solid support, one or more polymerase molecules can be attached to the solid support. Attachment of polymerase to a solid support can provide an advantage in localizing the polymerase for a subsequent detection step. This can be useful for example, when screening polymerase variants for ability to form a stabilized ternary complex with a primed template nucleic acid and nucleotide that are delivered via solution phase. Alternatively, attachment of the polymerase can be useful for localizing the polymerase at a feature where a particular nucleic acid resides.

Optionally, the provided methods further include a wash step. The wash step can occur before or after any other step in the method. Optionally, the wash step is performed after each of the serially contacting steps, wherein the primed template nucleic acid molecule is contacted with one of the distinguishably labeled polymerase-nucleotide combinations. Optionally, the wash step is performed prior to the monitoring step and/or prior to the determining or identifying step. Optionally, the wash step occurs under conditions that stabilize the ternary complex. Optionally, the conditions result from the presence of a reversible terminator moiety on the 3' nucleotide of the primer of the primed template nucleic acid molecule. Optionally, the conditions include a stabilizing agent. Optionally, the stabilizing agent is a non-catalytic metal ion (e.g., a divalent non-catalytic metal ion) that inhibits nucleotide incorporation or polymerization. Non-catalytic metal ions include, but are not limited to, calcium, strontium, scandium, titanium, vanadium, chromium, iron, cobalt, nickel, copper, zinc, gallium, germanium, arsenic, selenium, rhodium, europium, and terbium ions. Optionally, the wash buffer includes nucleotides from previous contacting steps, but does not include the distinguishably labeled polymerase composition of a prior polymerase-nucleotide combination. Including the nucleotides from previous contacting steps can provide the advantage of stabilizing previously formed ternary complexes from unwanted disassociation. This in turn prevents unwanted loss of signal due to washing away previously formed ternary complexes or emergence of erroneous signals due to reconstitution between one or more component(s) of previously formed ternary complexes and one or more component(s) of an incoming reagent. Optionally, the ternary complex has a half-life and the wash step is performed for a duration shorter than the half-life of the ternary complex formed when a nucleotide molecule provides a base that is complementary to the next base of the primed template nucleic acid molecule.

The examination step may be controlled, in part, by providing reaction conditions to prevent chemical incorporation of a nucleotide, while allowing determination of the identity of the next correct base on the primed template nucleic acid molecule. Such reaction conditions may be referred to as examination reaction conditions. Optionally, a ternary complex is formed under examination conditions.

Optionally, the examination conditions accentuate the difference in affinity for polymerase to primed template nucleic acids in the presence of different nucleotides, for example by destabilizing binary complexes. Optionally, the examination conditions cause differential affinity of the polymerase for the primed template nucleic acid in the presence of different nucleotides. By way of example, the examination conditions that cause differential affinity of the polymerase for the primed template nucleic acid in the presence of different nucleotides include, but are not limited to, high salt and glutamate ions. For example, the salt may dissolve in aqueous solution to yield a monovalent cation, such as a monovalent metal cation (e.g., sodium ion or potassium ion). Optionally, the salt that provides the monovalent cations (e.g., monovalent metal cations) further provides glutamate anions. Optionally, the source of glutamate ions can be potassium glutamate. In some instances, the concentrations of potassium glutamate that can be used to alter polymerase affinity of the primed template nucleic acid extend from 10 mM to 1.6 M of potassium glutamate, or any amount in between 10 mM and 1.6 M. As indicated above, high salt refers to a concentration of salt from 50 to 1,500 mM salt.

Optionally, examination involves detecting polymerase interaction with a template nucleic acid where the interaction of one or more polymerase compositions (e.g., where each different polymerase composition contains a different polymerase, or a different combination of two or more polymerases) can be distinguished. Detection may include optical, electrical, thermal, acoustic, chemical and mechanical means. Optionally, examination is performed after a wash step, wherein the wash step removes any non-bound reagents (e.g., unbound polymerases and/or nucleotides) from the region of observation. This may occur at the end of a series of steps involving contacting of a primed template nucleic acid molecule with a plurality of distinguishable polymerase-nucleotide combinations. Optionally, examination is performed during a wash step, such that the dissociation kinetics of the polymerase-nucleic acid or polymerase-nucleic acid-nucleotide complexes may be monitored and used to determine the identity of the next base. Optionally, examination is performed during the course of addition of the examination reaction mixture (or first reaction mixture), such that the association kinetics of the polymerase to the nucleic acid may be monitored and used to determine the identity of the next base on the nucleic acid. Optionally, examination involves distinguishing ternary complexes from binary complexes of polymerase and nucleic acid. Optionally, examination is performed under equilibrium conditions where the affinities measured are equilibrium affinities. Multiple examination steps comprising different or similar examination reagents, may be performed sequentially to ascertain the identity of the next template base. Multiple examination steps may be utilized in cases where multiple template nucleic acids are being sequenced simultaneously in one sequencing reaction, wherein different nucleic acids react differently to the different examination reagents. Optionally, multiple examination steps may improve the accuracy of next base determination. Optionally, a single examination step is used to identify the next correct nucleotide, out of a plurality of possible nucleotides (e.g., four possible nucleotides), for different primed template nucleic acid molecules among a population.

Generally, the examination step involves binding a polymerase to the polymerization initiation site of a primed template nucleic acid in a reaction mixture comprising one or more nucleotides, and monitoring the interaction. In certain preferred embodiments, this is accomplished using only a single polymerase in combination with one or more nucleotides. This may involve use of only a single nucleotide. Optionally, a nucleotide is sequestered within the polymerase-primed template nucleic acid complex to form a ternary complex under conditions in which incorporation of the enclosed nucleotide by the polymerase is attenuated or inhibited. Optionally, the ternary complex is alternatively or additionally stabilized by the presence of a blocking moiety (e.g., a reversible terminator moiety) on the 3' terminal nucleotide of the primer. Optionally a stabilizer is added to stabilize the ternary complex in the presence of the next correct nucleotide. This ternary complex is in a stabilized or polymerase-trapped pre-chemistry conformation.

Contacting Steps

In the provided methods, contacting of the primed template nucleic acid molecule with a reaction mixture that includes a polymerase composition and one nucleotide optionally occurs under conditions that stabilize formation of the ternary complex, and that destabilize formation of binary complexes. These conditions can be provided by alternative approaches that are a matter of choice by the end-user.

Optionally, the conditions comprise contacting the primed template nucleic acid molecule with a buffer that regulates osmotic pressure. Optionally, the reaction mixture used in the examination step includes the buffer that regulates osmotic pressure. Optionally, the buffer is a high salt buffer that includes a monovalent ion, such as a monovalent metal ion (e.g., potassium ion or sodium ion) at a concentration of from 50 to 1,500 mM. Salt concentrations in the range of from 100 to 1,500 mM, and from 200 to 1,500 mM also are highly preferred. Optionally, the buffer further includes a source of glutamate ions (e.g., potassium glutamate). Optionally, the conditions that stabilize formation of the ternary complex involve contacting the primed template nucleic acid molecule with a stabilizing agent. Optionally, the reaction mixture used during the examination step includes a stabilizing agent. Optionally, the stabilizing agent is a non-catalytic metal ion (e.g., a divalent or trivalent non-catalytic metal ion). Non-catalytic metal ions useful in this context include, but are not limited to, calcium, strontium, scandium, titanium, vanadium, chromium, iron, cobalt, nickel, copper, zinc, gallium, germanium, arsenic, selenium, rhodium, europium, and terbium.

Optionally, the contacting step is facilitated by the use of a flow cell or chamber, multiwell plate, etc. Flowing liquid reagents through the flow cell, which contains an interior solid support surface (e.g., a planar surface), conveniently permits reagent exchange or replacement. Immobilized to the interior surface of the flow cell is one or more primed template nucleic acids to be sequenced or interrogated using the procedures described herein. Typical flow cells will include microfluidic valving that permits delivery of liquid reagents (e.g., components of the "reaction mixtures" discussed herein) to an entry port. Liquid reagents can be removed from the flow cell by exiting through an exit port.

As discussed above, in certain embodiments it is desirable to avoid mixing one distinguishably labeled polymerase-nucleotide combination reagent with a subsequent polymerase-nucleotide combination reagent during the plurality of serial contacting steps. This can be accomplished by including an intervening wash step between each of the serial contacting steps. This may be done by alternatively flowing a binding mixture that includes a polymerase-nucleotide combination reagent and a wash solution through a flow cell. By another approach, robotic fluid handling may be used to perform reagent exchanges when using a multi-well formatted platform.

Detecting Steps

Detecting (e.g., via monitoring or measuring) the interaction of a polymerase with a primed template nucleic acid molecule in the presence of a nucleotide molecule may be accomplished in many different ways. For example, monitoring can include measuring association kinetics for the interaction between the primed template nucleic acid, the polymerase, and any one of the four nucleotide molecules. Monitoring the interaction of the polymerase with the primed template nucleic acid molecule in the presence of a nucleotide molecule can include measuring equilibrium binding constants between the polymerase and primed template nucleic acid molecule (i.e., equilibrium binding constants of polymerase to the template nucleic acid in the presence of any one or the four nucleotides). Thus, for example, the monitoring includes measuring the equilibrium binding constant of the polymerase to the primed template nucleic acid in the presence of any one of the four nucleotides. Monitoring the interaction of the polymerase with the primed template nucleic acid molecule in the presence of a nucleotide molecule includes, for example, measuring dissociation kinetics of the polymerase from the primed template nucleic acid in the presence of any one of the four nucleotides. Optionally, monitoring the interaction of the polymerase with the primed template nucleic acid molecule in the presence of a nucleotide molecule includes measuring dissociation kinetics of the dissociation of the closed-complex (i.e., dissociation of the primed template nucleic acid, the polymerase, and any one of the four nucleotide molecules). Optionally, the measured association kinetics are different depending on the identity of the nucleotide molecule. Optionally, the polymerase has a different affinity for each of the four types of nucleotide molecules. Optionally, the polymerase has a different dissociation constant for each of the four types of nucleotide molecules in each type of ternary complex. Association, equilibrium and dissociation kinetics are known and can be readily determined by one in the art. See, for example, Markiewicz et al., *Nucleic Acids Research* 40(16):7975-84 (2012); Xia et al., *J. Am. Chem. Soc.* 135(1):193-202 (2013); Brown et al., *J. Nucleic Acids*, Article ID 871939, 11 pages (2010); Washington, et al., *Mol. Cell. Biol.* 24(2):936-43 (2004); Walsh and Beuning, *J. Nucleic Acids*, Article ID 530963, 17 pages (2012); and Roettger, et al., *Biochemistry* 47(37):9718-9727 (2008), which are incorporated by reference herein in their entireties.

The detecting step can include monitoring the steady state interaction of the polymerase with the primed template nucleic acid molecule in the presence of the first nucleotide molecule, without chemical incorporation of the first nucleotide molecule into the primer of the primed template nucleic acid molecule. Optionally, the detecting includes monitoring dissociation of the polymerase with the primed template nucleic acid molecule in the presence of the first nucleotide molecule, without chemical incorporation of the first nucleotide molecule into the primer of the primed template nucleic acid molecule. Optionally, the detecting includes monitoring association of the polymerase with the primed template nucleic acid molecule in the presence of the first nucleotide molecule, without chemical incorporation of the first nucleotide molecule into the primer of the primed template nucleic acid molecule. Again, the test nucleotides in these procedures may be native nucleotides (i.e., unlabeled), labeled nucleotides (e.g., including fluorescent or Raman scattering labels), or nucleotide analogs (e.g., nucleotides modified to include reversible terminator moieties with or without detectable label moieties). It will be understood that a detection technique can accumulate signal over a relatively brief duration as is typically understood to be a single timepoint acquisition or, alternatively, signal can be continuously monitored over time as is typical of a time-based acquisition. It is also possible to acquire a series of timepoints to obtain a time-based acquisition.

In the sequencing methods provided herein, either a chemical block on the 3' nucleotide of the primer of the primed template nucleic acid molecule (e.g., a reversible terminator moiety on the base or sugar of the nucleotide), the absence of a catalytic metal ion in the reaction mixture, or the absence of a catalytic metal ion in the active site of the polymerase prevents the chemical incorporation of the nucleotide into the primer of the primed template nucleic acid. Optionally, the chelation of a catalytic metal ion in the reaction mixtures of the contacting step prevents the chemical incorporation of the nucleotide into the primer of the primed template nucleic acid. Optionally, a non-catalytic metal ion acts as a stabilizer for the ternary complex in the presence of the next correct nucleotide. Optionally, the substitution of a catalytic metal ion in the reaction mixtures of the contacting step with a non-catalytic metal ion prevents the chemical incorporation of the nucleotide molecule to the primed template nucleic acid. Optionally, the catalytic metal ion is magnesium. The metal ion mechanisms of polymerases postulate that a low concentration of metal ions may be needed to stabilize the polymerase-nucleotide-DNA binding interaction. See, for instance, Section 27.2.2, Berg J M, Tymoczko J L, Stryer L, *Biochemistry 5th Edition*, WH Freeman Press, 2002.

Optionally, a low concentration of a catalytic ion in the reaction mixture used during the examination step prevents the chemical incorporation of the nucleotide molecule to the primed template nucleic acid. Optionally, a low concentration is from about 1 µM to about 100 µM. Optionally, a low concentration is from about 0.5 µM to about 5 µM. Optionally, the reaction mixture used during the examination step includes cobalt ions and the incorporating step involves contacting with an incorporation reaction mixture that includes a higher concentration of cobalt ions as compared to the concentration of cobalt ions in the first reaction mixture.

In an exemplary sequencing reaction, the examination step involves formation and/or stabilization of a ternary complex including a polymerase, primed template nucleic acid, and nucleotide. Characteristics of the formation and/or release of the ternary complex can be detected to identify the enclosed nucleotide and therefore the next base in the template nucleic acid. Ternary complex characteristics can be dependent on the sequencing reaction components (e.g., polymerase, primer, template nucleic acid, nucleotide) and/or reaction mixture components and/or conditions.

The examination step involves detecting the interaction of a polymerase with a template nucleic acid in the presence of a nucleotide. The formation of a ternary complex may be detected or monitored. Optionally, the absence of formation of ternary complex is detected or monitored. Optionally, the dissociation of a ternary complex is monitored. Optionally, the incorporation step involves detecting or monitoring incorporation of a nucleotide. Optionally, the incorporation step involves detecting or monitoring the absence of nucleotide incorporation.

Any process of the examination and/or incorporation step may be detected or monitored. Optionally, a polymerase has a detectable tag (e.g., a fluorescent label or a Raman scattering tag). Optionally, the detectable tag or label on the polymerase is removable. Generally speaking, when using single-scan imaging, among the series of distinguishable polymerase and nucleotide combinations employed in the procedure, as few as two polymerases among the plurality of different polymerase-nucleotide combinations will harbor detectable labels. As indicated elsewhere herein, this can provide information about four different nucleotides based on monitoring ternary complex formation. A single polymerase label can be used when multiple scans (e.g., four independent scans) are performed.

Optionally, a nucleotide of a particular type (e.g., dATP, dCTP, dGTP, dTTP, or analogs thereof) is made available to a polymerase in the presence of a primed template nucleic acid molecule. The reaction is detected or monitored, wherein, if the nucleotide is a next correct nucleotide, the polymerase may be stabilized to form a ternary complex. If the nucleotide is an incorrect nucleotide, a ternary complex may still be formed; however, without the additional assistance of stabilizing agents or reaction conditions (e.g., absence of catalytic ions, polymerase inhibitors, salt), the ternary complex may dissociate. The rate of dissociation is dependent on the affinity of the particular combination of polymerase, template nucleic acid, and nucleotide, as well as reaction conditions. Optionally, the affinity is measured as an off-rate. Optionally, the affinity is different between different nucleotides for the ternary complex. For example, if the next base in the template nucleic acid downstream of the 3'-end of the primer is G, the polymerase-nucleic acid affinity, measured as an off-rate, is expected to be different based on whether dATP, dCTP, dGTP or dTTP (or analogs thereof) are added. In this case, dCTP would have the slowest off-rate, with the other nucleotides providing different off-rates for the interaction. Optionally, the off-rate may be different depending on the reaction conditions, for example, the presence of stabilizing agents (e.g., absence of magnesium or inhibitory compounds) or reaction conditions (e.g., nucleotide modifications or modified polymerases).

Once the identity of the next correct nucleotide is determined, 1, 2, 3, 4 or more nucleotide types may be introduced simultaneously to the reaction mixture under conditions that specifically target the formation of a ternary complex. Excess nucleotides optionally may be removed from the reaction mixture and the reaction conditions modulated to incorporate the next correct nucleotide of the ternary complex. This sequencing reaction ensures that only one nucleotide is incorporated per sequencing cycle. Preferably, reversible terminator nucleotides are employed in the incorporation step, and optionally, the reversible terminator nucleotides are not labeled with fluorescent or other labels.

Identifying Steps

The identity of the next correct base or nucleotide can be determined by detecting the presence, formation, and/or dissociation of the ternary complex. The identity of the next correct nucleotide may be determined without covalently incorporating the nucleotide into to the primer at its 3'-end. Optionally, the identity of the next base is determined by detecting the affinity of the polymerase and the primed template nucleic acid in the presence of added nucleotides. Optionally, the affinity of the polymerase and the primed template nucleic acid in the presence of the next correct nucleotide may be used to determine the next correct base on the template nucleic acid. Optionally, the affinity of the polymerase to the primed template nucleic acid in the presence of an incorrect nucleotide may be used to determine the next correct base on the template nucleic acid.

In certain embodiments, a ternary complex that includes a primed template nucleic acid (or a blocked primed template nucleic acid) is formed in the presence of a polymerase and a plurality of nucleotides. Cognate nucleotide participating in the ternary complex optionally is identified by observing destabilization of the complex that occurs when the cognate nucleotide is absent from the reaction mixture. This is conveniently carried out, for example, by exchanging one reaction mixture for another. Here, loss of the complex is an indicator of cognate nucleotide identity. Loss of binding signal (e.g., a fluorescent binding signal associated with a particular locus on a solid support) can occur when the primed template nucleic acid is exposed to a reaction mixture that does not include the cognate nucleotide. Optionally, maintenance of a ternary complex in the presence of a single nucleotide in a reaction mixture also can indicate identity of the cognate nucleotide. When reversible terminator nucleotides are employed, removal of excess nucleotides is unnecessary because only a single reversible terminator nucleotide can be incorporated before the reversible terminator moiety is removed.

Incorporation Steps

Optionally, incorporation proceeds after the cognate nucleotide has been identified in an examination procedure using a first polymerase in accordance with the disclosure. Incorporation optionally may employ a polymerase different from the one used in the examination step, together with a nucleotide analog. For example, the nucleotide analog can be an unlabeled reversible terminator nucleotide corresponding to the identified cognate nucleotide (i.e., the reversible terminator nucleotide and the cognate nucleotide are both complementary to the same base of the template strand). Also significantly, cognate nucleotides for a plurality of different primed template nucleic acids having different sequences advantageously can be identified using only a single imaging step. This is sometimes referred to as "single-scan imaging." Thus, the provided approach is both simple to implement and rapid to analyze.

The methods described herein optionally include an incorporation step. The incorporation step involves covalently incorporating one or more nucleotides at the 3'-end of a primer hybridized to a template nucleic acid. In a preferred embodiment, only a single nucleotide is incorporated at the 3'-end of the primer. Optionally, multiple nucleotides of the same kind are incorporated at the 3'-end of the primer. Optionally, multiple nucleotides of different kinds are incorporated at the 3'-end of the primer. Incorporated nucleotides alternatively can be unlabeled nucleotides, reversible terminator nucleotides, or detectably labeled nucleotide analogs. The polymerase can dissociate from the polymerization initiation site after nucleotide incorporation or can be retained at the polymerization initiation site after incorporation.

The incorporation reaction may be facilitated by an incorporation reaction mixture. Optionally, the incorporation reaction mixture has a different composition of nucleotides than the examination reaction. For example, the examination reaction can include one type of nucleotide and the incorporation reaction can include another type of nucleotide. Optionally, the incorporation reaction includes a polymerase that is different from the polymerases of the examination step. By way of another example, the examination reaction comprises one type of nucleotide and the incorporation reaction comprises four types of nucleotides, or vice versa. In yet another example, the examination reaction uses four different reagents, each containing one of four types of nucleotides, such that the four types of nucleotides are sequentially present, and the incorporation reaction can include the four types of nucleotides in a simultaneous mixture. As a further example, a first examination reaction can introduce a first type of nucleotide, a second examination reaction can introduce a second type of nucleotide along with the first type of nucleotide, a third examination reaction can introduce a third type of nucleotide along with the first and second types of nucleotides, a fourth examination reaction can introduce a fourth type of nucleotide along with the first, second and third types of nucleotides, and the incorporation reaction can include the first, second, third and fourth types of nucleotides in a simultaneous mixture. Optionally, an examination reaction mixture is altered or replaced by an incorporation reaction mixture. Optionally, an incorporation reaction mixture includes a catalytic metal ion (e.g., a divalent catalytic metal ion), a monovalent metal cation (e.g., potassium ions or sodium ions), glutamate ions, or a combination thereof.

There is flexibility in the nature of the nucleotide used in the incorporation step. For example, the at least one nucleotide can include a 3'-oxygen, which can be, for example, a member of a free 3'-hydroxyl group. Optionally, the 3' position of the at least one nucleotide molecule is modified to include a 3' terminator moiety. The 3' terminator moiety may be a reversible terminator or may be an irreversible terminator. Optionally, the reversible terminator nucleotide includes a 3'-$ONH_2$ moiety attached at the 3' position of the sugar moiety. Optionally, the reversible terminator of the at least one nucleotide molecule is replaced or removed before or after the examination step. Further examples of useful reversible terminator moieties are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference Nucleotides (e.g., incorporable nucleotides that are neither reversible terminator nucleotides, nor irreversible terminator nucleotides) present in the reaction mixture but not sequestered in a ternary complex may cause multiple nucleotide insertions during an incorporation reaction. A wash step can be employed prior to the chemical incorporation step to promote or ensure only the nucleotide sequestered within a trapped ternary complex being available for incorporation during the incorporation step. Optionally, free nucleotides may be removed by enzymes such as phosphatases. The trapped polymerase complex may be a ternary complex, a stabilized ternary complex or ternary complex involving the polymerase, primed template nucleic acid and next correct nucleotide.

Optionally, the nucleotide enclosed within the ternary complex of the examination step is incorporated into the 3'-end of the template nucleic acid primer during the incorporation step. For example, a stabilized ternary complex of the examination step includes an incorporated next correct nucleotide.

Optionally, the incorporation step involves replacing a nucleotide from the examination step and incorporating another nucleotide into the 3'-end of the template nucleic acid primer. The incorporation step can involve releasing a nucleotide from within a ternary complex (e.g., the nucleotide is a modified nucleotide or nucleotide analog) and incorporating a nucleotide of a different kind into the 3'-end of the primer of the primed template nucleic acid molecule. Optionally, the released nucleotide is removed and replaced with an incorporation reaction mixture containing a next correct nucleotide. For example, the incorporated nucleotide can be a reversible terminator nucleotide, such as an unlabeled reversible terminator nucleotide that does not include a detectable fluorophore.

Suitable reaction conditions for incorporation may involve replacing the examination reaction mixture with an incorporation reaction mixture. Optionally, nucleotide(s) present in the examination reaction mixture are replaced with one or more nucleotides in the incorporation reaction mixture. Optionally, the polymerase(s) present during the examination step is replaced during the incorporation step. By this approach it is possible to employ different types of polymerase in the examination and incorporation steps. Optionally, the polymerase present during the examination step is modified during the incorporation step. Optionally, the one or more nucleotides present during the examination step are modified during the incorporation step. The reaction mixture and/or reaction conditions present during the examination step may be altered by any means during the incorporation step. These means include, but are not limited to, removing reagents, chelating reagents, diluting reagents, adding reagents, altering reaction conditions such as conductivity or pH, and any combination thereof.

Optionally, the provided reaction mixture(s), including the incorporation reaction mixture(s), include at least one nucleotide molecule that is a non-incorporable nucleotide or a nucleotide incapable of incorporation into the nucleic acid strand. In other words, the provided reaction mixture(s) can include one or more nucleotide molecules incapable of incorporation into the primer of the primed template nucleic acid molecule. Such nucleotides incapable of incorporation include, for example, monophosphate and diphosphate nucleotides. In another example, the nucleotide may contain modification(s) to the triphosphate group that make the nucleotide non-incorporable. Examples of non-incorporable nucleotides may be found in U.S. Pat. No. 7,482,120, which is incorporated by reference herein in its entirety. Optionally, the primer may not contain a free hydroxyl group at its 3'-end, thereby rendering the primer incapable of incorporating any nucleotide, and, thus, making any nucleotide non-incorporable.

A polymerase inhibitor optionally may be included with the reaction mixtures containing test nucleotides in the examination step to trap the polymerase on the nucleic acid upon binding the next correct nucleotide. Optionally, the polymerase inhibitor is a pyrophosphate analog. Optionally, the polymerase inhibitor is an allosteric inhibitor. Optionally, the polymerase inhibitor is a DNA or an RNA aptamer. Optionally, the polymerase inhibitor competes with a catalytic ion-binding site in the polymerase. Optionally, the polymerase inhibitor is a reverse transcriptase inhibitor. The polymerase inhibitor may be an HIV-1 reverse transcriptase inhibitor or an HIV-2 reverse transcriptase inhibitor. The HIV-1 reverse transcriptase inhibitor may be a (4/6-halogen/MeO/EtO-substituted benzo[d]thiazol-2-yl)thiazolidin-4-one.

The provided method may further include preparing the primed template nucleic acid molecule for a next examination step after the incorporation step. Optionally, the preparing includes subjecting the primed template nucleic acid or the nucleic acid/polymerase complex to one or more wash steps; a temperature change; a mechanical vibration; a pH change; a chemical treatment to remove reversible terminator moieties; or an optical stimulation. Optionally, the wash step comprises contacting the primed template nucleic acid or the primed template nucleic acid/polymerase complex with one of more buffers, detergents, protein denaturants, proteases, oxidizing agents, reducing agents, or other agents capable of releasing internal crosslinks within a polymerase or crosslinks between a polymerase and nucleic acid.

In some embodiments, the disclosed techniques do not share restrictions on detectable labels that characterize certain other techniques used in the DNA sequencing field. For example, in some embodiments, there is no requirement for a label (e.g., a FRET partner) to be present on the polymerase, the primed template nucleic acid, or the nucleotide sequestered within a ternary complex. Alternatively, FRET partner can be present on a polymerase having a sequence set forth herein. The FRET partner can be positioned to interact with a FRET partner on a primer, template or nucleotide. The FRET partner that is attached to the polymerase can be a donor or acceptor in a FRET interaction.

In certain embodiments the polymerase is unlabeled, or does not generate any signal used for identifying cognate or non-cognate nucleotide. In other embodiments, the polymerase includes a covalently attached detectable label, such as a fluorescent label, a Raman scattering tag, etc. The polymerase preferably does not transfer energy to any labeled nucleotide to render it detectable by the detection apparatus used for carrying out the technique. The label or dye of the detectable nucleotide(s) or polymerase(s) employed in the procedure preferably is not an intercalating dye (e.g., as disclosed in U.S. Pat. No. 8,399,196), that changes its signal-generating properties (e.g., fluorescent output) upon binding DNA. As well, the label or dye present on the labeled nucleotide need not be a conformationally sensitive dye that changes spectral properties when it is the cognate nucleotide present in a ternary complex.

In the provided sequencing methods, the next correct nucleotide can be identified before an incorporation step, thereby allowing the incorporation step to avoid the use of labeled reagents and/or monitoring. Optionally, nucleotides used for identifying the next correct nucleotide are free of attached detectable tags or labels. Indeed, in some preferred embodiments, none of the nucleotides in the procedure contains a detectable label. Optionally, a nucleotide includes a detectable label, but the label is not detected in the method of identifying the next correct nucleotide. Optionally, when fluorescently labeled nucleotides are used for determining identity of the next correct nucleotide, the fluorescent label shows substantially no change in its fluorescent properties (excitation and emission) as the result of interaction with any nucleotide (e.g., through base pairing in a ternary complex), or as the result of a conformational change to the polymerase itself. Thus, for example, polymerase signaling does not require energy transfer to or from the detectable label because of nucleotide interaction with the polymerase. Optionally, the detectable label of a distinguishably labeled polymerase is a fluorescent label, but the fluorescent label is not an intercalating dye that changes properties upon binding a primed template nucleic acid molecule.

In certain preferred embodiments, the polymerase is labeled with a fluorescent detectable label, where the detectable label shows substantially no change in its fluorescent properties (excitation and emission) as the result of interaction with any nucleotide, or as the result of a conformational change to the polymerase itself. Thus, for example, labeled polymerase signaling does not require energy transfer to or from the detectable label because of nucleotide interaction with the polymerase. Optionally, the detectable label of a distinguishably labeled polymerase is a fluorescent label, but the fluorescent label is not an intercalating dye that changes properties upon binding a primed template nucleic acid molecule. Optionally, a polymerase having a sequence set forth herein can be attached to a nucleic acid intercalating dye. Exemplary intercalating dyes and methods for their use are set forth, for example, in U.S. Pat. No. 8,399,196, which is incorporated herein by reference.

The examination step of the sequencing reaction may be repeated 1, 2, 3, 4 or more times prior to the incorporation step. The examination and incorporation steps may be repeated for a predefined number of cycles, until the desired sequence of the template nucleic acid is obtained or until certain reaction criteria are reached such as a minimum signal intensity or signal to noise ratio.

Sequencing Methods Employing Destabilization of Ternary Complexes Containing Engineered Polymerases: General Aspects Engineered DNA polymerases in accordance with this disclosure can be used in sequencing procedures employing ternary complex destabilization, for example as described in commonly owned U.S. patent application identified by Ser. No. 15/581,828, published as US 2017/0314064 A1, the entire disclosure of which is incorporated by reference herein. The technique involves initial formation of a ternary complex using a plurality of nucleotides, and then subsequently investigating stability of the complex under a series of changed reagent conditions. These changed conditions involve progressive removal of nucleotides from a controlled series of binding reaction mixtures. For example, a ternary complex that includes a particular dNTP will require that dNTP in a first reagent solution to maintain integrity of the complex. Exchanging the first reagent solution with a second reagent solution that does not include the critical dNTP will cause destabilization of the complex, which can be detected as an indicator of nucleotide identity.

In one embodiment, there is a method of identifying a nucleotide that includes a base complementary to the next base of a template strand immediately downstream of a primer in a primed template nucleic acid molecule. The method can begin with the step of (a) providing a blocked primed template nucleic acid molecule including a reversible terminator moiety that precludes the 3'-terminus of the blocked primed template nucleic acid molecule from participating in phosphodiester bond formation. There also is the step of (b) contacting the blocked primed template nucleic acid molecule with a first reaction mixture that includes an engineered DNA polymerase, and a plurality of different nucleotide molecules. As a result, there forms a stabilized ternary complex that includes one of the plurality of different nucleotide molecules. There also is the step of (c) contacting the stabilized ternary complex with a second reaction mixture that includes at least one of the different nucleotide molecules and that does not include a first nucleotide molecule of the plurality of different nucleotide molecules. There also is the step of (d) monitoring interaction of the polymerase and the blocked primed template nucleic acid molecule in contact with the second reaction mixture to detect any of the stabilized ternary complex remaining after step (c). Still further, there is the step of (e) identifying the nucleotide that includes the base complementary to the next base of the template strand using results from step (d).

In another embodiment, there is a method of identifying a nucleotide that includes a base complementary to the next base of a template strand immediately downstream of a primer in a primed template nucleic acid molecule. The method can begin with the step of (a) providing the primed template nucleic acid molecule. There also is the step of (b) contacting the primed template nucleic acid molecule with a first reaction mixture that includes an engineered DNA polymerase and a plurality of different nucleotide molecules. As a result, there forms a stabilized ternary complex that includes one of the plurality of different nucleotide molecules. There also is the step of (c) contacting the primed template nucleic acid molecule, after step (b), with a second reaction mixture that includes at least one of the different nucleotide molecules and that does not include a first nucleotide molecule of the plurality of different nucleotide molecules. There also is the step of (d) monitoring interaction of the engineered DNA polymerase and the primed template nucleic acid molecule in the second reaction mixture, without incorporating any nucleotide into the primer, to detect any of the stabilized ternary complex remaining after step (c). Still further, there is the step of (e) identifying the nucleotide that includes the base complementary to the next base of the template strand using results from step (d).

In another embodiment, there is a method of identifying a nucleotide that includes a base complementary to the next base of a template strand immediately downstream of a primer in a primed template nucleic acid molecule. The method can begin with the step of (a) providing the primed template nucleic acid molecule. There also is the step of (b) contacting the primed template nucleic acid molecule with a first reaction mixture that includes an engineered DNA polymerase, but does not include any nucleotide, whereby a binary complex forms. There also is the step of (c) contacting the binary complex with a second reaction mixture that includes a plurality of different nucleotide molecules, whereby a stabilized ternary complex forms if one of the plurality of different nucleotide molecules includes the base complementary to the next base of the template strand. There also is the step of (d) detecting, without incorporating any nucleotide into the primer, any of the stabilized ternary complex that may have formed. There also is the step of (e) contacting the primed template nucleic acid molecule, after step (d), with a third reaction mixture that includes at least one of the different nucleotide molecules and that does not include a first nucleotide molecule of the plurality of different nucleotide molecules. There also is the step of (f) detecting, without incorporating any nucleotide into the primer, any of the stabilized ternary complex remaining after step (e). Still further, there is the step of (g) identifying the nucleotide that includes the base complementary to the next base of the template strand using results from both of detecting steps (d) and (f).

Reaction Mixtures

Nucleic acid sequencing reaction mixtures, or simply "reaction mixtures," can include one or more reagents that are commonly present in polymerase-based nucleic acid synthesis reactions. Reaction mixture reagents include, but are not limited to, enzymes (e.g., polymerase(s)), dNTPs (or analogs thereof), template nucleic acids, primer nucleic acids (including 3' blocked primers), salts, buffers, small molecules, co-factors, metals, and ions. The ions may be catalytic ions, divalent catalytic ions, non-catalytic ions, non-covalent metal ions, or a combination thereof. The reaction mixture can include salts, such as NaCl, KCl, potassium acetate, ammonium acetate, potassium glutamate, $NH_4Cl$, or $(NH_4HSO_4)$, that ionize in aqueous solution to yield monovalent cations. The reaction mixture can include a source of ions, such as $Mg^{2+}$ or $Mn^{2+}$, $Co^{2+}$, $Cd^{2+}$ or $Ba^{2+}$ ions. The reaction mixture can include tin, $Ca^{2+}$, $Zn^{2+}$, $Cu^{2+}$, $Co^{2+}$, $Fe^{2+}$ (e.g., $Fe(II)SO_4$), or $Ni^{2+}$, or other divalent or trivalent non-catalytic metal cation that stabilizes ternary complexes by inhibiting formation of phosphodiester bonds between the primed template nucleic acid molecule and the cognate nucleotide.

The buffer can include Tris, Tricine, HEPES, MOPS, ACES, MES, phosphate-based buffers, and acetate-based buffers. The reaction mixture can include chelating agents such as EDTA, EGTA, and the like. Optionally, the reaction mixture includes cross-linking reagents. Provided herein are first reaction mixtures, optionally, used during the examination step, as well as incorporation reaction mixtures used during nucleotide incorporation that can include one or more of the aforementioned agents. First reaction mixtures when used during examination can be referred to herein as examination reaction mixtures. Optionally, the first reaction mixture comprises a high concentration of salt; a high pH; 1, 2, 3, 4, or more types of nucleotides; potassium glutamate; a chelating agent; a polymerase inhibitor; a catalytic metal ion; a non-catalytic metal ion; or any combination thereof. The first reaction mixture can include 10 mM to 1.6 M of potassium glutamate (including any amount between 10 mM and 1.6 M). Optionally, the incorporation reaction mixture comprises a catalytic metal ion; 1, 2, 3, 4, or more types of nucleotides; potassium chloride; a non-catalytic metal ion; or any combination thereof.

The provided methods can be conducted under reaction conditions that modulate the formation and stabilization of a ternary complex during an examination step. The reaction conditions of the examination step typically favor the formation and/or stabilization of a ternary complex encapsulating a nucleotide and hinder the formation and/or stabilization of a binary complex. The binary interaction between the polymerase and template nucleic acid may be manipulated by modulating sequencing reaction parameters such as ionic strength, pH, temperature, or any combination thereof, or by the addition of a binary complex destabilizing agent to the reaction. Optionally, high salt (e.g., 50 to 1,500 mM) and/or pH changes are utilized to destabilize a binary complex. Optionally, a binary complex may form between a polymerase and a template nucleic acid during the examination or incorporation step of the sequencing reaction, regardless of the presence of a nucleotide. Optionally, the reaction conditions favor the stabilization of a ternary complex and destabilization of a binary complex. By way of example, the pH of the examination reaction mixture can be adjusted from 4.0 to 10.0 to favor the stabilization of a ternary complex and destabilization of a binary complex. Optionally, the pH of the examination reaction mixture is from 4.0 to 6.0. Optionally, the pH of the examination reaction mixture is 6.0 to 10.0.

The provided sequencing methods disclosed herein can function to promote polymerase interaction with the nucleotides and template nucleic acid in a manner that reveals the identity of the next base while controlling the chemical addition of a nucleotide. Optionally, the methods are performed in the absence of detectably labeled nucleotides, or in the presence of labeled nucleotides wherein the labels are not detected or not distinguished from each other. Optionally, only the polymerase harbors a detectable label (e.g., a fluorescent detectable label), and only the label of the polymerase is detected in the procedure. Again, when the polymerase includes a detectable label, the detectable label preferably produces a signal that does not change upon interaction with a cognate or non-cognate nucleotide. For example, the detectable label does not participate in energy transfer to or from a labeled nucleotide, or to or from another label that indicates conformational states of the polymerase. However, it will be understood that in some embodiments a polymerase having a sequence set forth herein can include a label that participates in energy transfer to or from a labeled nucleotide, or to or from another label that indicates conformational states of the polymerase.

Provided herein are methods for the formation and/or stabilization of a ternary complex comprising a polymerase bound to a primed template nucleic acid and a nucleotide enclosed within the polymerase-template nucleic acid complex, under examination reaction conditions. Examination reaction conditions may inhibit or attenuate nucleotide incorporation. Optionally, incorporation of the enclosed nucleotide is inhibited and the complex is stabilized or trapped in a pre-chemistry conformation or a ternary complex. Optionally, the enclosed nucleotide is incorporated and a subsequent nucleotide incorporation is inhibited. In this instance, the complex may be stabilized or trapped in a pre-translocation conformation. For the sequencing reactions provided herein, the ternary complex is stabilized during the examination step, allowing for controlled nucleotide incorporation. Optionally, a stabilized ternary complex is a complex wherein incorporation of an enclosed nucleotide is attenuated, either transiently (e.g., to examine the complex and then incorporate the nucleotide) or permanently (e.g., for examination only) during an examination step.

Optionally, the enclosed nucleotide has severely reduced or disabled binding to the template nucleic acid in the ternary complex. Optionally, the enclosed nucleotide is base-paired to the template nucleic acid at a next base. Optionally, the identity of the polymerase, nucleotide, primer, template nucleic acid, or any combination thereof, affects the interaction between the enclosed nucleotide and the template nucleic acid in the ternary complex.

Optionally, the enclosed nucleotide is bound to the polymerase of the closed-complex. Optionally, the enclosed nucleotide is weakly associated with the polymerase of the ternary complex. Optionally, the identity of the polymerase, nucleotide, primer, template nucleic acid, or any combination thereof, affects the interaction between the enclosed nucleotide and the polymerase in the ternary complex. For a given polymerase, each nucleotide may have a different affinity for the polymerase than another nucleotide. Optionally, a plurality of nucleotides, for example, all of the nucleotide types that have been used in reagents of the previous steps of the cycle, is present in a wash buffer. Optionally, the plurality of polymerases includes two polymerases that harbor distinguishable detectable labels, and the polymerases are components of a combination used with a single nucleotide. Optionally, this affinity is dependent, in part, on the template nucleic acid and/or the primer.

Optionally, the examination reaction condition comprises a plurality of primed template nucleic acids, polymerases, nucleotides, or any combination thereof. Optionally, the plurality of nucleotides comprises at least 1, 2, 3, 4, or more types of different nucleotides, for example dATP, dTTP (or dUTP), dGTP, and dCTP. Alternatively or additionally, the plurality of nucleotides comprises at most 1, 2, 3, or 4 types of different nucleotides, for example dATP, dTTP (or dUTP), dGTP, and dCTP. Optionally, the plurality of nucleotides comprises one or more types of nucleotides that, individually or collectively, complement at least 1, 2, 3 or 4 types of nucleotides in a template, for example dATP, dTTP (or dUTP), dGTP, or dCTP. Alternatively or additionally, the plurality of nucleotides comprises one or more types of nucleotides that, individually or collectively, complement at most 1, 2, 3 or 4 types of nucleotides in a template, for example dATP, dTTP (or dUTP), dGTP, or dCTP. Optionally, the plurality of template nucleic acids is a clonal population of template nucleic acids.

Optionally, the examination reaction mixture comprises one or more reagents or biomolecules generally present in a nucleic acid polymerization reaction. Reaction components used in addition to those set forth herein, may include, but are not limited to, salts, buffers, small molecules, detergents, crowding agents, metals, and ions. Optionally, properties of the reaction mixture may be manipulated, for example, electrically, magnetically, and/or with vibration.

Useful Nucleotides and Nucleotide Analogs

Optionally, a ternary complex of an examination step comprises either a native nucleotide, or a nucleotide analog or modified nucleotide to facilitate stabilization of the ternary complex. Optionally, a nucleotide analog comprises a nitrogenous base, five-carbon sugar, and phosphate group; wherein any moiety of the nucleotide may be modified, removed and/or replaced. Nucleotide analogs may be non-incorporable nucleotides. Non-incorporable nucleotides may be modified to become incorporable at any point during the sequencing method.

Nucleotide analogs include, but are not limited to, alpha-phosphate modified nucleotides, alpha-beta nucleotide analogs, beta-phosphate modified nucleotides, beta-gamma nucleotide analogs, gamma-phosphate modified nucleotides, caged nucleotides, or ddNTPs. Examples of nucleotide analogs are described in U.S. Pat. No. 8,071,755, which is incorporated by reference herein in its entirety.

Nucleotide analogs can include terminators that reversibly prevent nucleotide incorporation at the 3'-end of the primer. One type of reversible terminator is a 3'-O-blocked reversible terminator. Here the terminator moiety is linked to the oxygen atom of the 3'-OH end of the 5-carbon sugar of a nucleotide. For example, U.S. Pat. Nos. 7,544,794 and 8,034,923 (the disclosures of these patents are incorporated by reference) describe reversible terminator dNTPs having the 3'-OH group replaced by a 3'-$ONH_2$ group. Another type of reversible terminator is a 3'-unblocked reversible terminator, wherein the terminator moiety is linked to the nitrogenous base of a nucleotide. For example, U.S. Pat. No. 8,808,989 (the disclosure of which is incorporated by reference) discloses particular examples of base-modified reversible terminator nucleotides that may be used in connection with the methods described herein. Other reversible terminators that similarly can be used in connection with the methods described herein include those described in U.S. Pat. Nos. 7,956,171, 8,071,755, and 9,399,798 (the disclosures of these U.S. patents are incorporated by reference). For reviews of nucleotide analogs having terminators see e.g., Mu, R., et al., "The History and Advances of Reversible Terminators Used in New Generations of Sequencing Technology," Genomics, Proteomics & Bioinformatics 11(1):34-40 (2013). Optionally, one or more native nucleotides employed during the examination step is replaced by a second type of nucleotide that is incorporated during the incorporation step. For example, nucleotides present in the reaction mixture used during an examination step may be replaced by nucleotide analogs that include reversible terminator moieties (e.g., positioned on the base or sugar of the nucleotide molecule).

Optionally, nucleotide analogs have terminator moieties that irreversibly prevent nucleotide incorporation at the 3'-end of the primer. Irreversible nucleotide analogs include 2',3'-dideoxynucleotides, ddNTPs (ddGTP, ddATP, ddTTP, ddCTP). Dideoxynucleotides lack the 3'-OH group of dNTPs that is essential for polymerase-mediated synthesis.

Optionally, non-incorporable nucleotides comprise a blocking moiety that inhibits or prevents the nucleotide from forming a covalent linkage to a second nucleotide (3'-OH of a primer) during the incorporation step of a nucleic acid polymerization reaction. In certain embodiments, the blocking moiety can be removed from the nucleotide, allowing for nucleotide incorporation.

Optionally, a nucleotide analog present in a ternary complex renders the ternary complex stable. Optionally, the nucleotide analog is non-incorporable. Optionally, the nucleotide analog is released and a native nucleotide is incorporated. Optionally, the ternary complex is released, the nucleotide analog is modified, and the modified nucleotide analog is incorporated. Optionally, the ternary complex is released under reaction conditions that modify and/or destabilize the nucleotide analog in the ternary complex.

Optionally, a nucleotide analog present in a ternary complex is incorporated and the ternary complex is stabilized. The ternary complex may be stabilized by the nucleotide analog, or for example, by any stabilizing methods disclosed herein. Optionally, the nucleotide analog does not allow for the incorporation of a subsequent nucleotide. The ternary complex can be released, for example, by any methods described herein, and the nucleotide analog is modified. The modified nucleotide analog may allow for subsequent incorporation of a nucleotide to its 3'-end.

Optionally, a nucleotide analog is present in the reaction mixture during the examination step. For example, 1, 2, 3, 4 or more nucleotide analog types are present in the reaction mixture during the examination step. Similarly, one or more nucleotide analog types that are present in the reaction mixture during the examination step can be complementary to at least 1, 2, 3 or 4 nucleotide types in a template nucleic acid. Optionally, a nucleotide analog is replaced, diluted, or sequestered during an incorporation step. Optionally, a nucleotide analog is replaced with a native nucleotide. The native nucleotide may include a next correct nucleotide. Optionally, a nucleotide analog is modified during an incorporation step. The modified nucleotide analog can be similar to or the same as a native nucleotide.

Any nucleotide modification that traps the polymerase in a ternary complex may be used in the methods disclosed herein. The nucleotide may be trapped permanently or transiently. Optionally, the nucleotide analog is not the means by which a closed-complex is stabilized. Any ternary complex stabilization method may be combined in a reaction utilizing a nucleotide analog.

Optionally, a nucleotide analog that allows for the stabilization of a closed-complex is combined with reaction conditions that usually release the ternary complex. The conditions include, but are not limited to, the presence of a release reagent (e.g., catalytic metal ion, such as magnesium or manganese). Optionally, the ternary complex is stabilized even in the presence of a catalytic metal ion. Optionally, the ternary complex is released even in the presence of a nucleotide analog. Optionally, the stabilization of the closed-complex is dependent, in part, on the concentrations and/or identity of the stabilization reagent and/or release reagents, and any combination thereof. Optionally, the stabilization of a ternary complex using nucleotide analogs is combined with additional reaction conditions that function to stabilize a ternary complex, including, but not limited to, sequestering, removing, reducing, omitting, and/or chelating a catalytic metal ion; the presence of a polymerase inhibitor, cross-linking agent; and any combination thereof.

Optionally, one or more nucleotides can be labeled with distinguishing and/or detectable tags or labels. However, in particular embodiments such tags or labels preferably are not detected during examination, identification of the base or incorporation of the base, and such tags or labels are not detected during the sequencing methods disclosed herein. The tags may be distinguishable by means of their differences in fluorescence, Raman spectrum, charge, mass, refractive index, luminescence, length, or any other measurable property. The tag may be attached to one or more different positions on the nucleotide, so long as the fidelity of binding to the polymerase-nucleic acid complex is sufficiently maintained to enable identification of the complementary base on the template nucleic acid correctly. Optionally, the tag is attached to the nucleobase of the nucleotide. Under suitable reaction conditions, the tagged nucleotides may be enclosed in a ternary complex with the polymerase and the primed template nucleic acid. Alternatively, a tag is attached to the gamma phosphate position of the nucleotide.

Useful Polymerase Compositions

In certain embodiments, the disclosed approach identifies a cognate nucleotide using the combination of a unique polymerase composition (e.g., a reagent including a polymerase that can be distinguished from others, such as a detectably labeled polymerase) and a single nucleotide (e.g., a native nucleotide) without incorporation of the nucleotide. Optionally, a single type of labeled polymerase is used in combination with different nucleotides, one at a time, to create the unique combinations. Alternatively, more than one distinguishably labeled polymerase can be used to create the unique polymerase-nucleotide combinations. While individually labeled polymerases may be used for each different nucleotide used in an examination step, mixtures of two different labeled polymerases alternatively can be used as a single unique polymerase composition. Generally speaking, the primer strand of a primed template nucleic acid molecule undergoing examination is chemically unchanged by the polymerase or any other enzyme during examination procedure that identifies the cognate nucleotide. This is to say that the primer is neither extended by formation of a new phosphodiester bond, nor shortened by nucleolytic degradation during the examination step to identify the next correct nucleotide.

It is to be understood that four distinguishable polymerase compositions in accordance with the disclosure do not necessarily require four different labeled polymerases. For example, two distinguishably labeled polymerases can be used in combination with two different nucleotides to yield two different polymerase-nucleotide combinations. Alternatively or additionally, a polymerase having both of the distinguishable labels or a mixture of the same two distinguishably labeled polymerases (i.e., representing a third distinct polymerase composition) can be used in combination with a third nucleotide to yield a third polymerase-nucleotide combination. Further alternatively or additionally, an unlabeled polymerase can be used in combination with a fourth nucleotide to yield a fourth polymerase-nucleotide combination (i.e., a "dark" combination). In some embodiments, use of a fourth polymerase-nucleotide combination can be avoided altogether, deducing by the absence of a signal indicating the cognate nucleotide is any of the first three nucleotides that the cognate must be, by default, the fourth nucleotide. By this approach, all four different cognate nucleotides can be identified using fewer than four different labels. Thus, at most one, two, or three polymerases used in the four polymerase compositions can harbor distinguishable labels. Optionally, four different polymerases are labeled with four different detectable moieties (e.g., fluorescent moieties or Raman labels). This approach has successfully allowed for simultaneous detection of the next correct nucleotide in a multiplexed field of features by the technique described herein.

Optionally, the polymerase employed during the examination step includes an exogenous detectable label (e.g., a fluorescent label or Raman scattering tag) chemically linked to the structure of the polymerase by a covalent bond after the polymerase has been at least partially purified using protein isolation techniques. For example, the exogenous detectable label can be chemically linked to the polymerase using a free sulfhydryl or a free amine moiety of the polymerase. This can involve chemical linkage to the polymerase through the side chain of a cysteine residue, or through the free amino group of the N-terminus. In certain preferred embodiments, a fluorescent label attached to the polymerase is useful for locating the polymerase, as may be important for determining whether or not the polymerase has localized to a feature or spot on an array corresponding to immobilized primed template nucleic acid. The fluorescent signal need not, and preferably does not change absorption or emission characteristics as the result of binding any nucleotide. Stated differently, the signal emitted by the labeled polymerase is maintained substantially uniformly in the presence and absence of any nucleotide being investigated as a possible next correct nucleotide.

Optionally, a polymerase in accordance with the present disclosure is tagged with a chemiluminescent tag, wherein closed-complex formation is monitored as a stable luminescence signal in the presence of the appropriate luminescence triggers. The unstable interaction of the polymerase with the template nucleic acid in the presence of an incorrect nucleotide results in a measurably weaker signal compared to the ternary complex formed in the presence of the next correct nucleotide. Additionally, an optional wash step prior to triggering luminescence can remove substantially all polymerase molecules not bound in a stable ternary complex.

Optionally, a polymerase is tagged with an optical scattering tag, wherein ternary complex formation is monitored as a stable optical scattering signal. The unstable interaction of the polymerase with the nucleic acid in the presence of an incorrect nucleotide results in a measurably weaker signal compared to the ternary complex formed in the presence of the next correct nucleotide.

Optionally, the polymerase is tagged with a plasmonic nanoparticle tag, wherein the ternary complex formation is monitored as a shift in plasmonic resonance that is different from the plasmonic resonance in the absence of the ternary complex or the presence of a ternary complex comprising an incorrect nucleotide. The change in plasmon resonance may be due to the change in local dielectric environment in the ternary complex, or it may be due to the synchronous aggregation of the plasmonic nanoparticles on a cluster of clonally amplified nucleic acid molecules or another means that affects the plasmons differently in the closed-complex configuration.

Optionally, the polymerase is tagged with a Raman scattering tag, wherein, the ternary complex formation is monitored as a stable Raman scattering signal. The unstable interaction of polymerase with the nucleic acid in the presence of an incorrect nucleotide results in a measurably weaker signal compared to the ternary complex formed in the presence of the next correct nucleotide.

A common method of introducing a detectable tag on a polymerase involves chemical conjugation to amines or cysteines present in the non-active regions of the polymerase. Such conjugation methods are well known in the art. As non-limiting examples, n-hydroxysuccinimide esters (NHS esters) are commonly employed to label amine groups that may be found on an enzyme. Cysteines readily react with thiols or maleimide groups, while carboxyl groups may be reacted with amines by activating them with EDC (1-Ethyl-3-[3-dimethylaminopropyl]carbodiimide hydrochloride). Optionally, N-Hydroxysuccinimide (NHS) chemistry is employed at pH ranges where only the N-terminal amines are reactive (for instance, pH 7), such that only a single tag is added per polymerase.

Optionally, the tag attached to the polymerase is a charge tag, such that the formation of stable ternary complex can be detected by electrical means by measuring changes in local charge density around the template nucleic acids. Methods for detecting electrical charges are well known in the art, comprising methods such as field-effect transistors, dielectric spectroscopy, impedance measurements, and pH measurements, among others. Field-effect transistors include, but are not limited to, ion-sensitive field-effect transistors (ISFET), charge-modulated field-effect transistors, insulated-gate field-effect transistors, metal oxide semiconductor field-effect transistors and field-effect transistors fabricated using semiconducting single wall carbon nanotubes.

Optionally, a charge tag is a peptide tag having an isoelectric point below about 4 or above about 10. Optionally, a polymerase comprising a peptide tag has a total isoelectric point below about 5 or above about 9. A charge tag may be any moiety which is positively or negatively charged. The charge tag may comprise additional moieties including mass and/or labels such as dyes. Optionally, the charge tag possesses a positive or negative charge only under certain reaction conditions such as changes in pH.

A polymerase optionally may be labeled with a fluorophore and/or quencher. Optionally, a nucleic acid is labeled with a fluorophore and/or quencher. Optionally, one or more nucleotides are labeled with a fluorophore and/or quencher. Exemplary fluorophores include, but are not limited to, fluorescent nanocrystals; quantum dots; green fluorescent protein and color shifted mutants thereof, phycobiliproteins such as phycocyanin and phycoerythrin, d-Rhodamine acceptor dyes including dichloro[R110], dichloro[R6G], dichloro[TAMRA], dichloro[ROX] or the like; fluorescein donor dye including fluorescein, 6-FAM, or the like; Cyanine dyes such as Cy3B; Alexa dyes, SETA dyes, Atto dyes such as alto 647N which forms a FRET pair with Cy3B and the like. Fluorophores include, but are not limited to, MDCC (7-diethylamino-3-[([(2-maleimidyl)ethyl]amino)carbonyl]coumarin), TET, HEX, Cy3, TMR, ROX, Texas Red, Cy5, LC red 705 and LC red 640. Fluorophores and methods for their use including attachment to polymerases and other molecules are described in The Molecular Probes® Handbook (Life Technologies, Carlsbad Calif.) and Fluorophores Guide (Promega, Madison, Wis.), which are incorporated herein by reference in their entireties. Exemplary quenchers include, but are not limited to, ZEN, IBFQ, BHQ-1, BHQ-2, DDQ-I, DDQ-11, Dabcyl, Qxl quencher, Iowa Black RQ, and IRDye QC-1.

Optionally, binding between a polymerase and a template nucleic acid in the presence of a correct nucleotide may induce a decrease in fluorescence, whereas binding with an incorrect nucleotide causes an increase in fluorescence. Binding between a polymerase and a template nucleic acid in the presence of a correct nucleotide may induce an increase in fluorescence, whereas binding with an incorrect nucleotide causes a decrease in fluorescence. The fluorescent signals may be used to monitor the kinetics of a nucleotide-induced conformational change and identify the next base in the template nucleic acid sequence.

Optionally, the polymerase/nucleic-acid interaction may be monitored by a scattering signal originating from the polymerase or tags attached to the polymerase, for instance, nanoparticle tags.

Use of Polymerase Inhibitors to Stabilize Ternary Complexes

A ternary complex may be formed and/or stabilized by including a polymerase inhibitor in the examination reaction mixture. Inhibitor molecules phosphonoacetate, (phosphonoacetic acid) and phosphonoformate (phosphonoformic acid, common name Foscarnet), Suramin, Aminoglycosides, INDOPY-1 and Tagetitoxin are non-limiting examples of uncompetitive or noncompetitive inhibitors of polymerase activity. The binding of the inhibitor molecule, near the active site of the enzyme, traps the polymerase in either a pre-translocation or post-translocation step of the nucleotide incorporation cycle, stabilizing the polymerase in its ternary complex conformation before or after the incorporation of a nucleotide, and forcing the polymerase to be bound to the template nucleic acid until the inhibitor molecules are not available in the reaction mixture by removal, dilution or chelation.

Thus, polymerase inhibitor prevents the incorporation of the nucleotide molecule into the primer of the primer template nucleic acid. Optionally, the inhibitor is a non-competitive inhibitor, an allosteric inhibitor, or an uncompetitive allosteric inhibitor. Optionally, the polymerase inhibitor competes with a catalytic ion binding site in the polymerase.

Optionally, the polymerase of the ternary complex is prevented from opening its finger domains and translocating to the next template nucleic acid position by using pyrophosphate analogs or other related molecules. Pyrophosphate analogs configure the polymerase in ternary complex by occupying sites close to the triphosphate binding site in the active pocket of the polymerase. Release of the pyrophosphate (PPi) is critical for the polymerase to assume the open conformation, translocate to the next template nucleic acid position, and accept the next nucleotide. The non-competitive inhibitor, such as Foscarnet (phosphonoformate), phosphonoacetate or other pyrophosphate analogs, traps the polymerase in its fingers-closed conformation. Optionally, binding of the PPi analog is reversible, with the polymerase activity fully restored by washing away, diluting, or sequestering the inhibitor in the reaction mixture. Broadly, any non-competitive inhibitor of polymerase activity may be used during the sequencing reaction.

Optionally, a polymerase inhibitor which stabilizes a ternary complex is combined with reaction conditions which usually release the ternary complex, including, but not limited to, the presence of a catalytic metal ion, such as magnesium or manganese. Optionally, the ternary complex is stabilized even in the presence of a catalytic metal ion. Optionally, the ternary complex is released even in the presence of a polymerase inhibitor. Optionally, the stabilization of the ternary complex is dependent, in part, on the concentrations, the identity of the stabilization reagent, the identity of release reagents, and any combination thereof. Optionally, the stabilization of a ternary complex using polymerase inhibitors is combined with additional reaction conditions which also function to stabilize a ternary complex, including, but not limited to, sequestering, removing, reducing, omitting, and/or chelating a catalytic metal ion; the presence of a modified polymerase in the ternary complex; a non-incorporable nucleotide in the ternary complex; and any combination thereof.

Discriminating Conditions: Distinguishing Binary and Ternary Complex Formation

Optionally, since particular embodiments utilize polymerase binding without incorporation to identify a cognate nucleotide (i.e., the next correct nucleotide), it can be beneficial to enhance discrimination between specific- and non-specific polymerase binding to the primed template nucleic acid. This can be achieved, in part, by reducing non-specific "background" binding due to binary complex formation.

Binary complex formation conveniently can be reduced, inhibited or destabilized by use of one or more salts that provide monovalent cations. Preferred concentration ranges are from 50 mM to 1,500 mM of a salt that provides monovalent cations (e.g., potassium ions). Preferably, the salt concentration is sufficient to preferentially destabilize binary complexes, and to favor ternary complex formation over binary complex formation by at least two-fold, by at least five-fold, or even more. Still further, the salt that provides monovalent cations may further provide a source of dicarboxylate anions, such as glutamate anions. The concentration of the salt that provides these ions can be from 10 mM to 1.6 M, optionally from 50 mM to 500 mM, or alternatively from 100 mM to 300 mM. Examples of monovalent metal cations include $Na^+$ and $K^+$; while examples of dicarboxylate anions include glutamate anions (e.g., arising from potassium glutamate).

Stabilizing Ternary Complexes and Controlling Polymerase Exchange

The ability to form and maintain ternary complexes (e.g., produced using four different polymerase-nucleotide combinations in serial fashion) on different features of an array can be facilitated by stabilization of ternary complexes. This can be accomplished in a variety of ways.

Optionally, a polymerase is stabilized in its ternary complex by one or a combination of approaches, including: reversible crosslinking of the polymerase to the nucleic acid; use of allosteric inhibition by small molecules, uncompetitive inhibitors, competitive inhibitors, and/or non-competitive inhibitors; use of non-catalytic cations; use of aptamers; use of anti-polymerase antibodies; use of a reversibly blocked primed template nucleic acid molecule (i.e., a non-extendible primer); and denaturation. Optionally, the polymerase inhibitor competes with a catalytic ion binding site in the polymerase. For example, aminoglycosides non-competitively inhibit polymerase activity by displacing magnesium binding sites in a Klenow polymerase. The non-competitive nature of the interaction with respect to nucleotide binding allows the polymerase to interact with the template nucleic acid and nucleotide, affecting only the catalytic step of nucleotide incorporation. In all instances, formation of the stabilized ternary complex provides information about the identity of the next base on the nucleic acid template. Particularly preferred approaches for trapping or stabilizing the polymerase in a ternary complex include the use of non-catalytic cations that inhibit phosphodiester bond formation, such as non-catalytic lanthanide cations, and/or allosteric inhibitors.

Stabilizing ternary complexes that included primed template nucleic acid, polymerase, and cognate nucleotide is illustrated below by the use of particular non-catalytic metal ions. To determine which non-catalytic metal cations afforded the longest retention of ternary complexes during subsequent binding and wash steps, various candidate cations were evaluated. Among the metal ions tested in this procedure were: $Cu^{2+}$, $Mn^{2+}$, $V^{5+}$, $Eu^{3+}$, $Ni^{2+}$, $Sr^{2+}$, $Tb^{3+}$, $Ca^{2+}$ and $Co^{2+}$. Certain preferred reaction conditions substantially maintain ternary complex signals in the absence of non-bound polymerase (i.e., polymerase free in solution, not bound to any immobilized template) over an extended period (e.g., of greater than about 30 seconds, such as about 30-60 seconds). For example, ternary complex binding signal measured at the desired time point following a wash step can be expressed as a percentage of the maximum signal (using the signal measured at the time of initial nucleotide contact as a baseline). Preferred metal ions include trivalent lanthanide ions, including europium ions and terbium ions. Results confirmed that superior retention of ternary complexes on primed template nucleic acid molecules by these cations were attributable to the physiochemical properties of trivalent lanthanides.

A blocked primer terminating at its 3'-end with a reversible terminator nucleotide that precludes phosphodiester bond formation also can be used for stabilizing ternary complex formation. Indeed, the product of a reaction that incorporates either a reversible or irreversible terminator nucleotide includes blocked primers that stabilize ternary complexes. In any reaction step described above, formation of a stabilized ternary complex containing a nucleotide that is not incorporated may be monitored to identify the next correct base in the nucleic acid sequence. Reaction conditions can be changed to disengage the polymerase and cognate nucleotide from a blocked primed template nucleic acid molecule, and changed again to remove from the local environment any reversible terminator moiety attached to the nucleotide at the 3'-end of the primer strand of the primed template nucleic acid molecule. In some embodiments, both the polymerase and cognate nucleotide of the ternary complex, and the reversible terminator moiety are removed in a single step using a reagent that dissociates ternary complexes and cleaves the reversible terminator moiety from its position at the 3'-end of the blocked primed template nucleic acid molecule.

Systems

The disclosed technique for determining cognate nucleotides using engineered polymerases, whether for a single nucleic acid feature or for a population of different nucleic acid features spaced apart in a flow cell or well of a multiwell plate, can be performed using a dedicated system of interrelated modules or components. Some useful systems will be familiar to those having an ordinary level of skill in the art, and can be adapted or configured for processing by the disclosed technique that relies on identification or tracking of distinguishably labeled polymerases. An exemplary system for use in identifying a next correct nucleotide of a primed template nucleic acid molecule typically will include: a reaction vessel; a reagent dispense module; an imaging module; a processing module; and an electronic storage device. Systems useful for single-scan imaging of a population of nucleic acid features will have the capability of detecting four different fluorescent emission wavelengths. Essential features of particularly preferred systems are described below.

The reaction vessel employed in the system may take different forms. The reaction vessel will be in fluid communication with a supply of one or more labeled polymerases. Examples of reaction vessels include flow cells having inlet and outlet ports, and one or more wells of a multiwell plate. Contained within the reaction vessel will be a collection or population of nucleic acid features to be processed by the disclosed technique. The nucleic acid features may be "clusters" of spaced-apart amplified nucleic acids (e.g., in situ amplified nucleic acids). Alternatively, individual beads harboring homogenous populations of nucleic acids may be contained within the reaction vessels.

The reagent dispense module also may take different forms. The reagent dispense module directs into the reaction vessel, one at a time, a liquid reagent that includes one of the labeled polymerases in combination with one or more different nucleotides for each of a plurality of reagent exchanges. Optionally, the labeled polymerases are distinguishably labeled polymerases that harbor different fluorescent detectable labels. Optionally, none of the fluorescent detectable labels is an intercalating dye, and none of the fluorescent detectable labels is excited by energy transfer from a different molecular species. Optionally, the reaction vessel is a flow cell, and each reagent exchange involves flowing through the flow cell a second liquid reagent to replace a first liquid reagent. Optionally, the reagent dispense module includes a syringe pump that controllably transfers one of the four distinguishably labeled polymerases in combination with one or more of four different nucleotides. Optionally, the liquid reagent directed into the reaction vessel by the reagent dispense module includes a ternary complex-stabilizing agent. Exemplary ternary complex-stabilizing agents are disclosed elsewhere, herein.

The imaging module also may take different forms. The imaging module will be capable of detecting which of the four distinguishably labeled polymerases is present in a complex that includes: (i) the primed template nucleic acid molecule; (ii) one of the four distinguishably labeled polymerases; and (iii) the next correct nucleotide. Optionally, the imaging module includes an illumination component and a detection component. Illumination components may take the form of light emitting diodes (LEDs) that generate a range of wavelengths. A plurality of different LEDs may be employed in the imaging module. Useful detectors include fluorometers that measure parameters of fluorescence. There also can be one or more optical filters for narrowing the range or band of wavelengths that are transmitted either to a sample or to a detector. The detection component of the imaging module optionally can be configured to detect intensities of a plurality of different wavelengths, each corresponding to a fluorescence emission by one of the four distinguishably labeled polymerases. Thus, each of the fluorescent detectable labels associated with one of the polymerases can be excited by a wavelength of energy produced by the illumination component (e.g., produced by one of the LEDs), and an emission signal produced by the detectable label can be detected by the detection component. In one embodiment, the imaging module includes an illumination component and a detection component, where each of four distinguishably labeled polymerases is labeled with a fluorescent detectable label, where each of the fluorescent detectable labels is excited by a wavelength of energy produced by the illumination component, and where the detection component is configured to detect intensities of a plurality of different wavelengths, each corresponding to a fluorescence emission by one of the four distinguishably labeled polymerases.

The processing module also can take different forms. For example, the processing module can include a computer (e.g., either a standalone computer or processor, a computer or processor integrated into the system within a common housing or chassis) configured with software to compare intensities of the plurality of different wavelengths, and to determine therefrom the identity of the next correct nucleotide. The processing module will be configured to receive a result from the imaging module, and further configured to identify the next correct nucleotide using the result processed result. Configuring of the processing module may involve embedded, or otherwise accessible software instructions (e.g., being accessed from a remote software repository).

The electronic storage device also can take different forms. The storage device will be in communication with the processing module, and can store a non-transient record of the next correct nucleotide identified by the processing module. For example, the electronic storage device can be a computer hard drive, flash drive, floppy disk, compact disk (CD) or other optical disk storage medium, cloud storage arrangement, and the like.

Optionally, the system can also include an output device that produces a non-transient record of the next correct nucleotide identified by the processing module. The non-transient record produced by the output device optionally can be either a record stored on computer-readable media, or a record printed on paper.

EXAMPLES

Following are illustrations showing how polymerases in accordance with the disclosure can be used in procedures for identifying one or more cognate nucleotides in the sequence of a primed template nucleic acid. Notably, engineered polymerases for each of the named mutant categories in Table 1 were prepared and tested for interaction with primed template nucleic acid in the presence of cognate or non-cognate nucleotides, and for the ability to catalyze phosphodiester bond formation (i.e., incorporate nucleotide into the primed template nucleic acid). In all cases, testing was conducted using polymerases that included the extraneous N-terminal stretch of amino acids represented by SEQ ID NO:6. Since this portion of the engineered polymerase does not participate in nucleotide binding or interaction with the primed template nucleic acid, inclusion of the sequence of SEQ ID NO:6, or portions thereof, by attachment to variants of the sequence of SEQ ID NO:3 is optional.

Example 1 describes the use of a TQE polymerase in Sequencing By Binding™ protocols involving cycles of examination to identify cognate nucleotides. Results demonstrated that the engineered enzyme exhibited substantially reduced non-specific DNA binding in the absence of cognate nucleotide while retaining the ability to incorporate cognate nucleotide in the presence of the catalytic $Mg^{2+}$ metal ion. As described above, the TQE mutant used in the demonstration included a single amino acid change relative to the polypeptide sequence of the related CBT parent enzyme having the polypeptide sequence of SEQ ID NO:1. Similarly, the CBT parent polymerase having the polypeptide sequence of SEQ ID NO:1 also was prepared and purified.

Example 1

Demonstration of Cognate Nucleotide Identification with Low Non-Specific DNA Binding Polymerase The above-described TQE mutant polymerase was prepared and purified using standard techniques that will be familiar to those having an ordinary level of skill in the art. The purified TQE mutant polymerase had the sequence of SEQ ID NO:1, except that that the amino acid at position 307 was Glu (E) instead of Gln (Q). None of the protein sequence modifications upstream of the first methionine of the Bst-f DNA polymerase (i.e., position 27 of SEQ ID NO:1; or SEQ ID NO:3) was deemed essential for the desired combination of reduced non-specific DNA binding in the absence of cognate nucleotide and for $Mg^{2+}$-catalyzed incorporation in the presence of cognate nucleotide. Thus, inclusion of these modifications is optional in the working product.

A FORTEBIO® (Menlo Park, Calif.) Octet instrument employing biolayer interferometry to measure binding reactions at the surface of a fiber optic tip was used in a multiwell plate format to illustrate properties of the polymerase in the context of a nucleic acid sequencing technique. Primed template nucleic acid molecules biotinylated at the 5'-ends of the template strand were immobilized onto fiber optic tips functionalized with streptavidin (SA) using standard procedures. The primed template nucleic acid molecule in this procedure had TA as the next two correct nucleotides downstream of the primer.

The cycling procedure involved steps for: (1) washing/regenerating sensor tips; (2) contacting the template with one of four native dNTPs to investigate complex formation; (3) washing with an EDTA solution to strip complexes from the primed template nucleic acid molecule. An incorporation step followed a complete round of binding and examination using the four dNTPs, one at a time. Sensor tips were washed/regenerated in a Tris-buffered solution (pH 8.0) that included KCl, potassium glutamate, and 0.01% Tween-20 before commencing the cycling protocol. The first incoming nucleotide was interrogated with 500 nM of either TQE or 500 nM of CBT in the presence of examination buffer (30 mM Tris-HCl (pH 8.0); either 50, 100 or 150 mM KCl; 320 mM potassium glutamate; 2 mM $SrCl_2$; 0.01% Tween-20; 0.1 mg/mL acetylated BSA; and 1 mM β-mercaptoethanol). Native nucleotides were employed in the procedure, and were contacted to the sensor tip in the following order: dATP, dTTP, dGTP, and dCTP. Each of the dNTPs was present at a concentration of 100 μM, except for dTTP, which was used at a concentration of 200 μM. Nucleotide binding steps were for a period of about 30 seconds at 30° C. At the end of each nucleotide binding and examination step, any formed complexes were washed from the sensor tip for 45 seconds using an EDTA solution containing KCl to chelate divalent cations. Thereafter, the biosensor was regenerated for 30 seconds before moving to the next dNTP exam.

Following examination of all four dNTPs to determine whether a ternary complex had formed, incorporation reactions were performed to compare polymerase activity of the TQE mutant with the CBT parent enzyme. First, ternary complexes were prepared by contacting the sensor tips with the cognate nucleotide (i.e., dTTP) at a concentration of 200 μM for 30 seconds. Next, biosensor tips were transferred to an incorporation buffer (30 mM Tris-HCl (pH 8.0), 50 mM KCl, 50 mM $Mg^{2+}$) for 30 seconds. Finally, complexes were washed from the sensor tips for 45 seconds using the EDTA solution containing KCl to chelate divalent cations. Again, the biosensor was regenerated for 30 seconds before moving to the next series of examination reactions using all four dNTPs, one at a time. Results from this latter set of examination reactions was informative regarding binding and incorporation activities of the mutant enzyme.

Figure 1B:
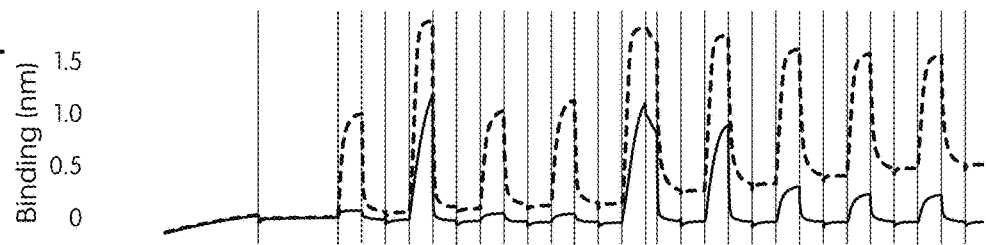
Figure 1C:
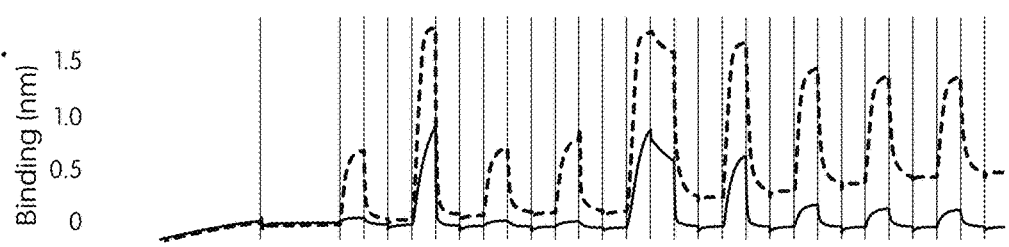

Results from the procedure, shown in FIGS. 1A-1C, confirmed that the specificity-enhanced TQE polymerase correctly identified the cognate nucleotide, bound the DNA template with substantially reduced affinity in the absence of cognate nucleotide, and correctly incorporated cognate nucleotide in the presence of the catalytic $Mg^{2+}$ metal ion. The figures show examination traces for all four nucleotides conducted using the TQE and CBT polymerases under three different buffer conditions. Ternary complexes generated in the presence of dTTP indicated that both polymerases correctly identified the cognate nucleotide. In all cases, non-cognate nucleotides were associated with substantially reduced binding signals for the TQE enzyme compared with the CBT parent. Following the step to permit incorporation, both the CBT and TQE enzymes were shown to possess catalytic activity. In both cases, the subsequent nucleotide (dATP) was properly identified. This indicated that cognate nucleotide had been incorporated efficiently by the mutant enzyme under incorporating conditions. Of course, a repetitive cycling procedure to conduct extensive sequence determination can use a different enzyme for the incorporation step. A reversible terminator nucleotide (e.g., an unlabeled reversible terminator nucleotide) may be used in the incorporation procedure. Optionally, different polymerase enzymes can be used to incorporate reversible terminator nucleotides and perform the examination steps.

Example 2 describes use of the UQE specificity-enhanced polymerase in Sequencing By Binding protocols involving cycles of examination to identify cognate nucleotides. Results demonstrated that the engineered UQE enzyme exhibited substantially reduced non-specific DNA binding in the absence of cognate nucleotide while retaining the ability to incorporate cognate nucleotide in the presence of the catalytic $Mg^{2+}$ metal ion. As described above, the UQE mutant includes a single amino acid change at position 314 of the modified CBU enzyme identified by SEQ ID NO:13. Again, this CBU parent enzyme included an exogenous cysteine residue and N-terminal His-tag.

Example 2

Demonstration of Cognate Nucleotide Identification with Low Non-Specific DNA Binding Polymerase The UQE mutant polymerase having the polypeptide sequence of SEQ ID NO:13, except for replacement of Gln (Q) by Glu (E) at position 314, was prepared and purified using standard molecular cloning, gene expression, and protein purification techniques that will be familiar to those having an ordinary level of skill in the art. Similarly, the CBU parent polymerase having the polypeptide sequence of SEQ ID NO:13 also was prepared and purified.

The procedures of Example 1 were followed, substituting the UQE polymerase in place of the TQE polymerase, and substituting the CBU polymerase in place of the CBT polymerase.

Figure 2A:
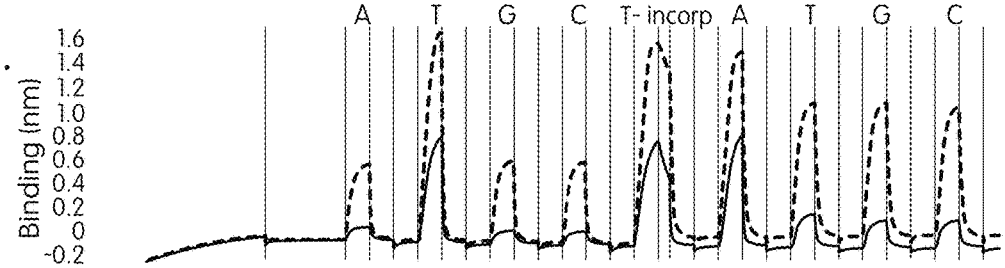
FIGS. 2A-2C are interferometry traces for single-nucleotide examinations, and incorporation steps; comparing results obtained using the CBU and UQE polymerases under different salt conditions.
Figure 2B:
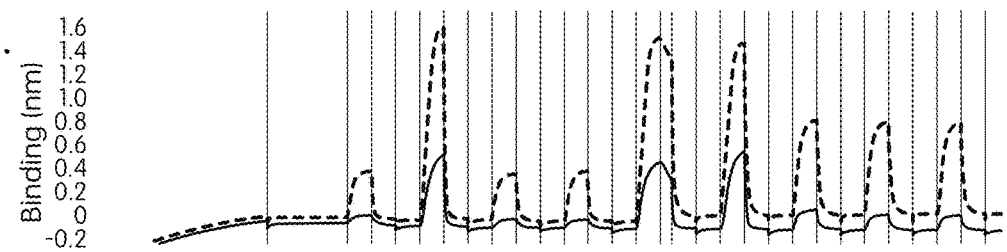
Figure 2C:
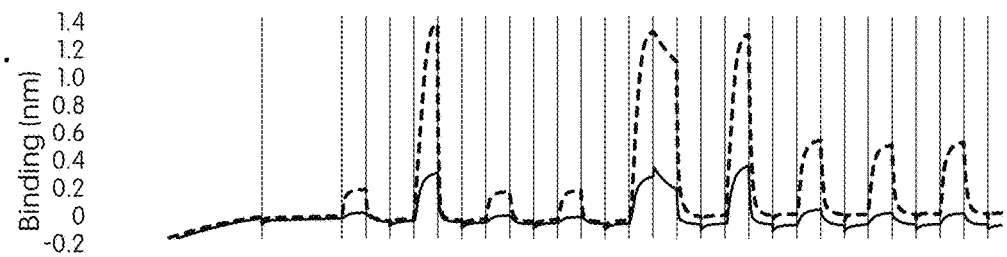

Results from the procedure, shown in FIG. 2, confirmed that the specificity-enhanced polymerase correctly identified the cognate nucleotide, bound the DNA template with substantially reduced binding in the absence of cognate nucleotide, and correctly incorporated cognate nucleotide in the presence of the catalytic $Mg^{2+}$ metal ion. The figure shows examination traces for all four nucleotides conducted using the UQE and CBU polymerases under three different buffer conditions. Ternary complexes generated in the presence of dTTP indicated that both polymerases correctly identified the cognate nucleotide. In all cases, non-cognate nucleotides were associated with substantially reduced binding signals for the UQE enzyme compared with the CBU parent. Following the step to permit incorporation, both the CBU and UQE enzymes were shown to possess catalytic activity. In both cases, the subsequent nucleotide (dATP) was properly identified. This indicated that cognate nucleotide had been incorporated efficiently by the mutant enzyme under incorporating conditions. Of course, a repetitive cycling procedure to conduct extensive sequence determination can use a different enzyme for the incorporation step. A reversible terminator nucleotide (e.g., an unlabeled reversible terminator nucleotide) may be used in the incorporation procedure. Optionally, different polymerase enzymes can be used to incorporate reversible terminator nucleotides and perform the examination steps.

The foregoing discussion of DNA polymerase mutants addressed instances wherein as few as a single amino acid change could distinguished a specificity-enhanced polymerase (e.g., a low background DNA binding polymerase) from its parent enzyme. Surprisingly, amino acid changes introduced into these mutants were in a region of the enzyme not previously known to exhibit sequence conservation suggestive of functional importance.

Following is a description of another mutant DNA polymerase, where this polymerase contained two amino acid changes relative to the parent polymerase. More particularly, the DSA mutant polymerase possesses increased nucleotide discrimination between correct and incorrect nucleotides. The DSA mutant was made by site-directed mutagenesis of the polynucleotide encoding the CBT polymerase of SEQ ID NO:1 so that amino acid positions 276 and 451 were both occupied by Cys residues. These regions of the polymerase altered by these changes are believed to be at the tip of the thumb and finger domains of the Bst-f polymerase. The consequence of the two altered positions was decreased binary background binding.

Example 3 describes use of the DSA specificity-enhanced polymerase in Sequencing By Binding protocols involving cycles of examination to identify cognate nucleotides. Results demonstrated that the engineered DSA enzyme exhibited substantially reduced non-specific DNA binding in the absence of cognate nucleotide while retaining the ability to incorporate cognate nucleotide in the presence of the catalytic $Mg^{2+}$ metal ion. As demonstrated below, the DSA polymerase advantageously gave a disproportionately large decrease in its binary and incorrect ternary binding compared to its correct ternary binding. Therefore, the DSA enzyme was capable of increased discrimination of ternary complexes having cognate nucleotides by lowering background binding that was due to binary complex formation. The DSA mutant includes two amino acid changes at positions 276 and 451 of the modified CBU enzyme identified by SEQ ID NO:1. Again, this CBU parent enzyme included an exogenous cysteine residue and N-terminal His-tag.

Example 3

Demonstration of Cognate Nucleotide Identification with Low Non-Specific DNA Binding Polymerase The DSA mutant polymerase having the polypeptide sequence of SEQ ID NO:1, except for replacement of Lys (K) and Gln (Q) by Cys (C) at each of positions 276 and 451, was prepared and purified using standard molecular cloning, gene expression, and protein purification techniques that will be familiar to those having an ordinary level of skill in the art. Similarly, the CBT parent polymerase having the polypeptide sequence of SEQ ID NO:1 also was prepared and purified.

A modification of the procedure in Example 1 was followed to assess polymerase activity, substituting the DSA polymerase in place of the TQE polymerase and adding a single step. The cycling procedure involved steps for: (1) washing/regenerating sensor tips; (2) contacting the template with a solution containing polymerase but no nucleotide; (3) contacting the template with one of four native dNTPs to investigate complex formation; and (4) washing with an EDTA solution to strip complexes from the primed template nucleic acid molecule. An incorporation step followed a complete round of binding and examination using the four dNTPs, one at a time. Sensor tips were washed/regenerated in a Tris-buffered solution (pH 8.0) that included KCl, potassium glutamate, 1 mM $SrCl_2$, 0.01% Tween-20 before commencing the cycling protocol. Binary complex formation was permitted by contacting sensor tips with wash/regeneration solution containing either 500 nM of DSA polymerase or 500 nM of CBT polymerase, but not containing any nucleotide. The first incoming nucleotide was interrogated with 500 nM of either DSA or 500 nM of CBT in the presence of examination buffer (30 mM Tris-HCl (pH 8.0); either 100, 200 or 400 mM KCl; 320 mM potassium glutamate; 2 mM $SrCl_2$; 0.01% Tween-20; 0.1 mg/mL acetylated BSA; and 1 mM β-mercaptoethanol). Native nucleotides were employed in the procedure, and were contacted to the sensor tip in the following order: dATP, dTTP, dGTP, and dCTP. Each of the dNTPs was present at a concentration of 100 µM, except for dTTP, which was used at a concentration of 200 µM. Nucleotide binding steps were for a period of about 15 seconds at 30° C. At the end of each nucleotide binding and examination step, any formed complexes were washed from the sensor tip for 45 seconds using a solution containing EDTA to chelate divalent cations. Thereafter, the biosensor was regenerated for 30 seconds before moving to the next dNTP exam.

Following examination of all four dNTPs to determine whether a ternary complex had formed, incorporation reactions were performed to compare polymerase activity of the DSA mutant with the CBT parent enzyme. First, ternary complexes were prepared by contacting the sensor tips with the cognate nucleotide (i.e., dATP) at a concentration of 100 µM for 30 seconds. Next, biosensor tips were transferred to an incorporation buffer (30 mM Tris-HCl (pH 8.0), 50 mM KCl, 50 mM $MgCl_2$) for 15 seconds. Finally, complexes were washed from the sensor tips for 45 seconds using the EDTA solution to chelate divalent cations. Again, the biosensor was regenerated before moving to the next series of examination reactions using all four dNTPs, one at a time. Results from this latter set of examination reactions was informative regarding binding and incorporation activities of the mutant enzyme.

Figure 3A:
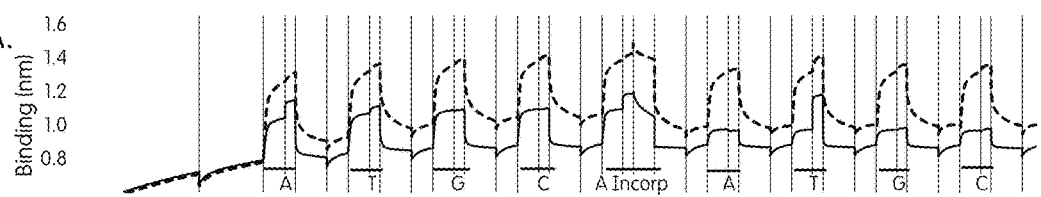
FIGS. 3A-3C are interferometry traces for single-nucleotide examinations, and incorporation steps; comparing results obtained using the CBT and DSA polymerases under different salt conditions.
Figure 3B:
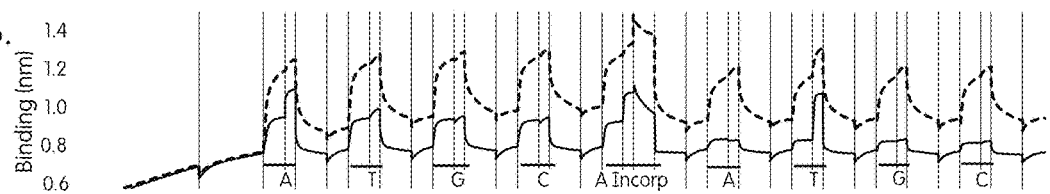
Figure 3C:
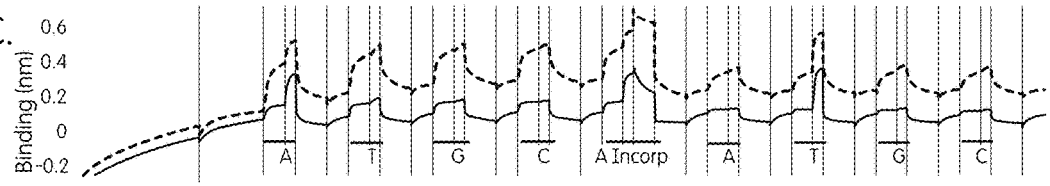

Results from the procedure, shown in FIG. 3, confirmed that the specificity-enhanced polymerase correctly identified the cognate nucleotide, bound the DNA template with substantially reduced binding in the absence of cognate nucleotide, and correctly incorporated cognate nucleotide in the presence of the catalytic $Mg^{2+}$ metal ion. The figure shows examination traces for all four nucleotides conducted using the DSA and CBT polymerases under three different buffer conditions. Ternary complexes generated in the presence of dATP indicated that both polymerases correctly identified the cognate nucleotide. Notably, the magnitude of the signal for DSA binding to DNA in the absence or presence of cognate nucleotide was generally lower than the signal for CBT binding to DNA (i.e., for both binary and ternary complex formation). DSA binding showed a disproportionally larger decrease in its binary signal compared to signal resulting from ternary complex formation. Therefore, despite the overall lower signal, the enzyme was capable of increased discrimination by lowering background binding. Surprisingly, the DSA polymerase also gave better discrimination between binary and ternary complex formation at lower concentrations of salt than CBT. Still further, results from the incorporation step confirmed that both the DSA and CBT enzymes possessed catalytic activity. In both cases, the subsequent nucleotide (dTTP) was properly identified. This indicated that cognate nucleotide had been incorporated efficiently by the mutant enzyme under incorporating conditions. Of course, a repetitive cycling procedure to conduct extensive sequence determination can use a different enzyme for the incorporation step. A reversible terminator nucleotide (e.g., an unlabeled reversible terminator nucleotide) may be used in the incorporation procedure. Optionally, different polymerase enzymes can be used to incorporate reversible terminator nucleotides and perform the examination steps.

Example 4 describes procedures illustrating the use of detectably labeled polymerases for determining cognate nucleotide identity. The Sequencing By Binding™ protocol in this Example employed label-free native nucleotides, and label-free primed template nucleic acids. The sequencing protocol was carried out by flowing different reagents through a flow cell containing immobilized primed template nucleic acids. Although individual types of nucleotides (i.e., either dATP, dGTP, dCTP, or dTTP) were tested one at a time for ternary complex formation with the primed template nucleic acid and labeled polymerase, an alternative protocol employs simultaneous testing of two or more distinguishably labeled polymerases (e.g., CBT, TQE, or DSA polymerases). Engineered polymerases in this Example were constructed using the scaffold of SEQ ID NO:1, including the amino acid substitutions indicated in Table 1, to permit convenient protein purification and fluorescent labeling. The same labeling could have been carried out using the thrombin cleavage product scaffold of SEQ ID NO:2, and is compatible with this procedure.

Example 4

Nucleic Acid Sequence Determination Using Engineered Polymerases Having Fluorescent Labels Nucleic acid features used as templates in a nucleic acid sequencing application were synthesized in situ within a flow cell using a rolling circle amplification (RCA) protocol. Immobilized primers hybridized to single-stranded circular templates were used to generate strands of sequencing templates. Immobilized strands were hybridized to complementary sequencing primers and then used in a Sequencing By Binding™ procedure. Sequencing primers were blocked from extension at their 3'-ends by incorporating reversible terminator nucleotides having 3' aminooxy (—ONH$_2$) blocking groups. A single type of template yielding TAGCATCAGA (SEQ ID NO:7) as the sequence to be determined was used in procedures with the CBT polymerase. Two different templates yielding CCCTGTCATG (SEQ ID NO:8) and CCCATTTATG (SEQ ID NO:9) as the sequences to be determined were used in procedures with the TQE polymerase. Similarly, two different templates yielding CCGATTCGTC (SEQ ID NO:10) and CCATGTTTCA (SEQ ID NO:11) as the sequences to be determined were used in procedures with the DSA polymerase.

A reagent cycling procedure with continuous fluorescence monitoring was used for assessing cognate nucleotide identification. Solutions containing a single type of nucleotide (dATP, dGTP, dCTP, or dTTP) in combination with either fluorescently labeled CBT polymerase, fluorescently labeled TQE polymerase, or fluorescently labeled DSA polymerase were flowed into the flow cell one at a time to permit formation and detection of ternary complexes. Polymerases were labeled using standard maleimide chemistry for covalent attachment of a Cy-5 moiety to the thiol functional group of an engineered Cys residue near the N-terminus. Flows of nucleotides were ordered as: dATP, dGTP, dCTP, and dTTP. All solutions used for these examination steps included Tris buffer (pH 8.0), KCl, trehalose, 1,2-propanediol, hydroxylamine, DMSO, Sr$^{2+}$ ion, F-127 detergent, 100 µM label-free dNTP (i.e., native dNTP), and 20 nM polymerase (i.e., either CBT, TQE, or DSA). Examination solutions containing the CBT polymerase were adjusted to include 240 mM KCl and 80 mM potassium glutamate; solutions containing the TQE polymerase were adjusted to include 180 mM KCl, and no potassium glutamate; while solutions containing the DSA polymerase were adjusted to include 50 mM KCl, and no potassium glutamate. Following each examination step to detect fluorescence associated with nucleic acid features during one of the nucleotide and polymerase flows, the flow cell was washed with a regeneration buffer that included Tris buffer (pH 8.0), 50 mM KCl, trehalose, 1,2-propanediol, hydroxylamine, DMSO, Sr$^{2+}$ ion, and F-127 detergent. This was followed by a wash with a quenching solution that included Tris buffer (pH 8.0), NaCl, Tween-20, SDS, 2 mM each of EDTA and NTA metal ion chelators, and hydroxylamine. This process was cycled four times to permit interrogation of each different nucleotide. Following each set of four examination reactions, 3'-ONH$_2$ blocking groups were removed from the primers using an acetate-buffered (pH 5.5) cleavage reagent that included NaNO$_2$ and TCEP. The next reversible terminator nucleotide was incorporated using a pH-buffered reaction mixture that included all four label-free reversible terminator nucleotides (i.e., dNTP-ONH$_2$) in a solution that included Therminator DNA polymerase (New England Biolabs; Ipswich, Mass.) and MgCl$_2$. All procedures were carried out at 47° C. Signals arising from fluorescent polymerase associating with immobilized nucleic acid features in the presence of different nucleotides were monitored and recorded throughout the procedure using a fluorescent microscope configured with a digital camera that detected emission from the Cy-5 fluorescent moiety joined to the polymerase. Pixels measured from captured images as a function of time were plotted to determine cognate nucleotide identity. In one approach, the nucleotide giving the highest magnitude fluorescent signal was identified as the cognate nucleotide.

Figure 4A:
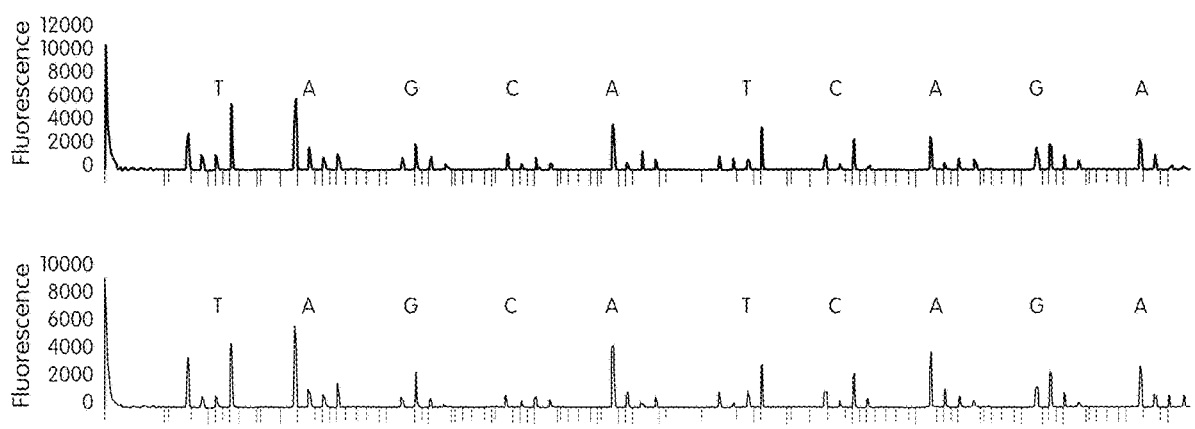
FIGS. 4A-4C, respectively presenting results obtained using detectably labeled CBT, TQE, and DSA polymerases, show fluorescent traces for polymerase ternary complex formation as a function of cycling progress. Correct bases are indicated in the panels of the figures above the different sets of four fluorescent traces, where each set of four peaks represented one complete cycle of testing four nucleotides. Between each set of four peaks there were steps to: (a) remove reversible terminator moieties that blocked nucleotide addition; and (b) incorporate a new reversible terminator nucleotide, thereby advancing the primer by one position.
Figure 4B:
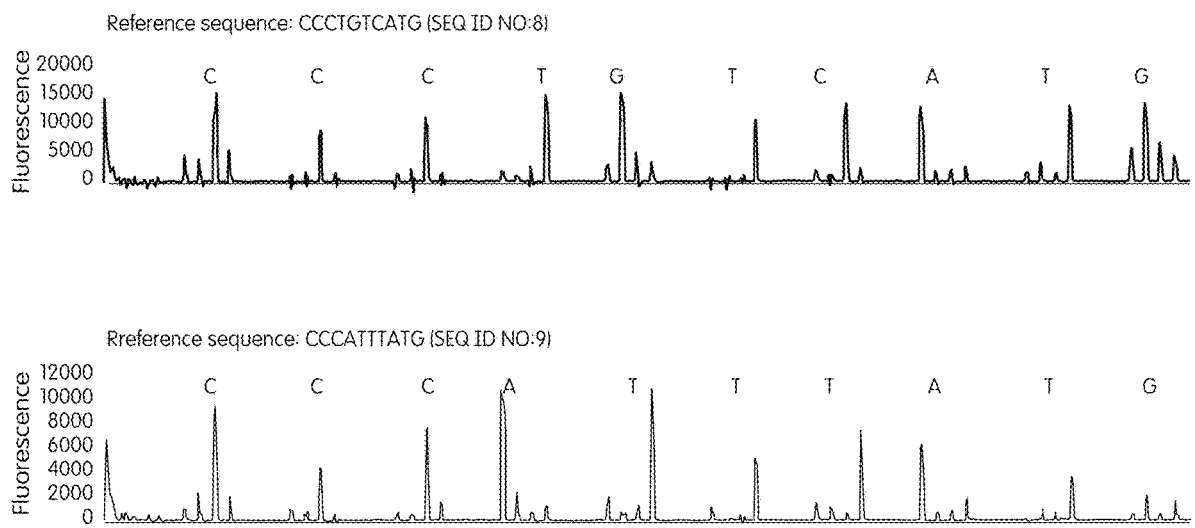
Figure 4C:
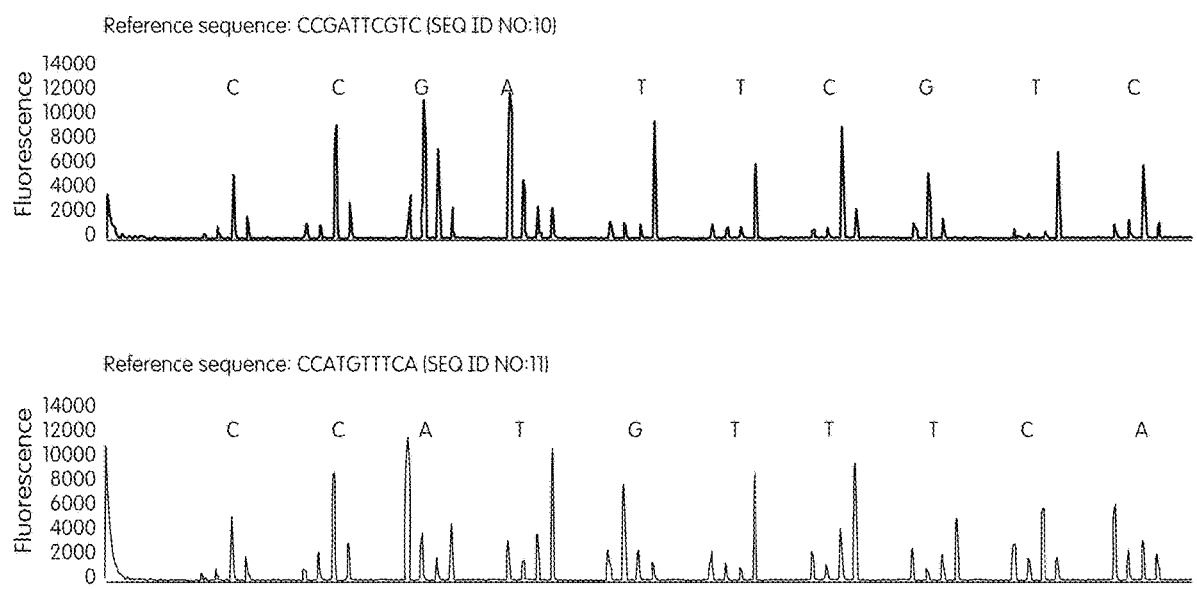

Results from this procedure showed that the TQE and DSA polymerases advantageously discriminated between cognate and non-cognate nucleotides under lower salt conditions compared to the CBT polymerase. This resulted in higher signal intensities. Procedures carried out using the parent CBT polymerase (see FIG. 4A) gave evidence for "read-ahead," where signals were detected for both the next correct base (i.e., "n+1") as well as for the subsequent base (i.e., "n+2"). For example, the highest signal among the first set of four nucleotides tested was associated with dTTP (the n+1 position), and the second highest signal was associated with dATP (the n+2 position). This feature of the CBT polymerase was substantially less apparent in results obtained using the TQE and DSA polymerases (see FIGS. 4B-4C). Signal-to-background measurements were generally higher when using the DSA polymerase, and so advantageously favored correct nucleotide identification using base calling algorithms where maximal peak height identified cognate nucleotide. Use of the DSA polymerase was also associated with signals of more uniform magnitude over more extended read lengths when compared with the CBT polymerase. Significantly, compared with results obtained using the CBT polymerase, and even the TQE polymerase, the DSA polymerase discriminated between cognate and non-cognate nucleotides under substantially lower salt conditions.

It was discovered during development of the presently disclosed techniques that there are advantages to achieving discrimination between formation of binary and ternary complexes under low salt conditions (e.g., where the concentration of salt providing monovalent cations is in the range of from 10 mM to 500 mM, or even from 10 mM to 250 mM. For example, the higher salt conditions frequently are used to achieve good discrimination between binary and ternary complex formation can lead to compaction of the sequencing template, thereby restricting polymerase access undesirably. Accordingly, certain preferred polymerases exhibited enhanced discrimination between cognate and non-cognate nucleotide binding under conditions where the concentration of KCl is below 250 mM when the concentration of potassium glutamate is below 350 mM.

Results presented herein demonstrated the benefits of performing Sequencing By Binding™ procedures using engineered polymerases characterized by low background DNA binding. Example polymerases having these features included the TQE and DSA polymerases, which advantageously retained the ability to incorporate cognate nucleotide. As indicated above, the DSA polymerase was further characterized by an ability to operate under low salt conditions that facilitated longer read lengths, possibly due to effects on the sequencing template. Significantly, the nature of the mutations characterizing these two mutant polymerases suggested that the mechanisms underlying changed functional activities relative to the parent polymerases were different. Different mutations resulting in novel characteristics were next combined into a single polymerase with the intention of achieving a synergistic effect that might not be possible when different mutations affected the same polymerase functionality.

Example 5 describes procedures showing how independent background-reducing mutations were combined in a single engineered polymerase that was used in Sequencing By Binding™ protocols. This engineered polymerase is referred to herein as "TEE."

Example 5

Polymerase Engineered for Enhanced Discrimination in Sequencing by Binding™ Protocols Conventional laboratory techniques that will be familiar to those having an ordinary level of skill in the art of molecular biology and protein purification were used to produce the TEE polymerase, which included mutated positions 250 (K to C), 281 (Q to E), and 425 (Q to C) in the scaffold of SEQ ID NO:3. Since the sequence of SEQ ID NO:3 is fully contained within the sequences of each of SEQ ID Nos:1-2, the amino acid replacements corresponded to positions 259, 290 and 434 of SEQ ID NO:2; and to positions 276, 307 and 451 of SEQ ID NO:1. Again, the scaffold of SEQ ID NO:1 included an N-terminal polypeptide sequence that aided in protein purification, and SEQ ID NO:2 represented the thrombin cleavage product of SEQ ID NO:1. To illustrate flexibility in the nature of polymerases that can be used, the polypeptide that included the extraneous polyhistidine motif was used to demonstrate functional similarities and differences with respect to the parent DSA polymerase.

Activity of the engineered TEE polymerase was investigated using the biolayer interferometry technique, essentially as described herein under Example 1. The first two cognate nucleotides for the sensor-immobilized template undergoing testing were dATP followed by dTTP. After initial loading of the primed template nucleic acid molecule, and washing to remove material that did not immobilize, the optical sensor tip was cycled through exposure to various reagents to permit assessment of binary and ternary complex formation. The cycles included exposure to the TEE polymerase in the absence of nucleotide (to permit formation of a binary complex); exposure to the combination of the TEE polymerase and an unlabeled test dNTP (to permit formation of a ternary complex when the test dNTP is the next correct nucleotide); stripping of all complexes from the sensor tip using an EDTA solution; and regenerating the tip with a washing/regenerating solution to remove traces of EDTA. In this instance one nucleotide at a time was used, with the order of exposure being: dATP, dTTP, dGTP, and dCTP. Alternative procedures can employ nucleotide combinations (e.g., pairwise combinations of different nucleotides). Examination conditions used in this procedure included 30 mM Tris-HCl (pH 8.0); 100 mM KCl; 320 mM potassium glutamate; 2 mM $SrCl_2$; 0.01% Tween-20; 0.1 mg/mL acetylated BSA; 1 mM β-mercaptoethanol; and 900 nM TEE polymerase.

Comparative results were obtained using the DSA polymerase in place of the TEE polymerase, where the procedures were conducted in parallel. The DSA polymerase used in the procedure included the extraneous polyhistidine-tag motif that also was present in the TEE polymerase used in the procedure. This meant that the two polymerases differed at only a single amino acid position. The DSA trial was carried out using 300 nM DSA in place of TEE. Signal magnitudes (peak heights) for cognate nucleotides were compared to the highest signal magnitude measured for incorrect nucleotides.

Following the first round of examination for all four nucleotides, an incorporation reaction was performed using each of the polymerases and only the next correct nucleotide, dATP. A single nucleotide incorporated into the primed template nucleic acid because the following cognate nucleotide for the synthetic template used in the procedure was dTTP. Procedures used for the incorporation reaction were essentially as described under Example 1. After the incorporation was complete, cycles of washing to regenerate the sensor tip; exposure to either the TEE or DSA polymerase in the absence of nucleotide to permit binary complex formation; and exposure to a test dNTP to investigate ternary complex formation were resumed.

Figure 5:
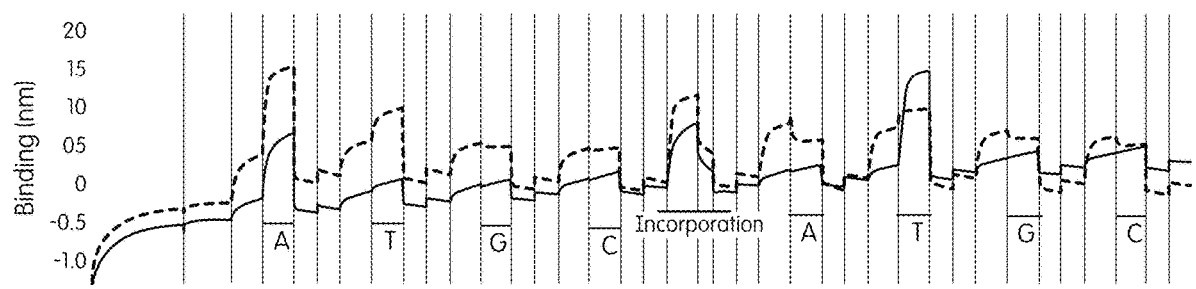
FIG. 5 is a set of interferometry traces for a series of single-nucleotide examination steps using the TEE polymerase and the DSA polymerase, where two rounds of examination for each polymerase are separated by an incorporation step. Identity of the nucleotide undergoing examination is indicated below the trace (i.e., "A" represents dATP, "T" represents dTTP, "G" represents dCTP, and "C" represents dCTP). Immediately preceding each nucleotide examination step is a step for polymerase binding in the absence of nucleotide (i.e., to permit binary complex formation). Immediately following each nucleotide examination are steps for stripping complexes from the primed template nucleic acid, and then regenerating the sensor tip by washing to remove traces of EDTA. Height and trajectory of the binding signals indicate the magnitude of complex formation.

Results from the procedure, shown in FIG. 5, demonstrated that the engineered TEE polymerase advantageously exhibited very low signal indicating binary complex formation, and high signal indicating ternary complex formation. The TEE polymerase also retained the ability to incorporate cognate nucleotide efficiently. As indicated in FIG. 5, the post-incorporation nucleotide-binding cycles clearly indicated that the next correct nucleotide was dTTP. This could only have resulted following incorporation of the preceding nucleotide (i.e., dATP). The ratio of correct-to-highest incorrect signal during the first round of examination conducted using four nucleotides was 2.75 for TEE (i.e., 1.10 vs. 0.4), and 1.95 for DSA (i.e., 1.75 vs. 0.9). The ratio of correct-to-highest incorrect signal during the second round of examination conducted using four nucleotides was 4.83 for TEE (i.e., 1.45 vs. 0.3), and 1.60 for DSA (i.e., 1.00 vs. 0.6). These latter results indicated that the engineered TEE polymerase exhibited improved discrimination between cognate and non-cognate nucleotides relative to the DSA parent polymerase. Improved discrimination can be an advantage, for example when using the polymerase in Sequencing By Binding™ protocol that identifies cognate nucleotide without incorporation.

This invention has been described with reference to a number of specific examples and embodiments thereof. Of course, a number of different embodiments of the present invention will suggest themselves to those having ordinary skill in the art upon review of the foregoing detailed description. Thus, the true scope of the present invention is to be determined upon reference to the appended claims.

What is claimed is:

1. An engineered DNA polymerase, comprising a variant of the sequence of SEQ ID NO:3, said variant being at least 80% identical to SEQ ID NO:3 and comprising an amino acid substitution mutation at one or more of positions K250, Q281, D355, Q425, and D532.

2. The engineered DNA polymerase of claim 1, wherein the variant is at least 90% identical to SEQ ID NO:3.

3. The engineered DNA polymerase of claim 2, wherein the variant is at least 95% identical to SEQ ID NO:3.

4. The engineered DNA polymerase of claim 3, wherein the variant is at least 98% identical to SEQ ID NO:3.

5. The engineered DNA polymerase of claim 2, further comprising the sequence of SEQ ID NO:5 joined to the amino terminus thereof.

6. The engineered DNA polymerase of claim 2, further comprising the sequence of SEQ ID NO:6 joined to the amino terminus thereof.

7. The engineered DNA polymerase of claim 1,
wherein the substitution mutation at position K250 comprises a mutation to a polar amino acid,
wherein the substitution mutation at position Q281 comprises a mutation to an acidic amino acid,
wherein the substitution mutation at position D355 comprises a mutation to a different acidic amino acid,
wherein the substitution mutation at position Q425 comprises a mutation to a different polar amino acid, and
wherein the substitution mutation at position D532 comprises a mutation to a different acidic amino acid.

8. The engineered DNA polymerase of claim 7,
wherein the substitution mutation at position K250 comprises a mutation to Cys,
wherein the substitution mutation at position Q281 comprises a mutation to Glu,
wherein the substitution mutation at position D355 comprises a mutation to Glu,
wherein the substitution mutation at position Q425 comprises a mutation to Cys, and
wherein the substitution mutation at position D532 comprises a mutation to Glu.

9. The engineered DNA polymerase of claim 1, wherein said variant comprises replacement of up to 10 amino acids of SEQ ID NO:3.

10. The engineered DNA polymerase of claim 9, wherein said variant comprises replacement of up to 5 amino acids of SEQ ID NO:3.

11. The engineered DNA polymerase of claim 1, wherein said variant is present in a ternary complex that further includes a primed template nucleic acid and a cognate nucleotide or analog thereof.

12. The engineered DNA polymerase of claim 11, wherein the cognate nucleotide or analog thereof comprises an exogenous fluorescent label.

13. The engineered DNA polymerase of claim 1, wherein the at least one amino acid substitution mutation is a substitution mutation at position Q281 that replaces Gln (Q) with Glu (E).

14. The engineered DNA polymerase of claim 1, wherein the at least one amino acid substitution mutation is a substitution mutation at position K250 that replaces Lys (K) with Cys (C), and a substitution mutation at position Q425 that replaces Gln (Q) with Cys (C).

15. The engineered DNA polymerase of claim 1, wherein the at least one amino acid substitution mutation is a substitution mutation at position Q281 that replaces Gln (Q) with Glu (E), a substitution mutation at position K250 that replaces Lys (K) with Cys (C), and a substitution mutation at position Q425 that replaces Gln (Q) with Cys (C).

16. The engineered DNA polymerase of claim 1, wherein the at least one amino acid substitution mutation is a substitution mutation at position D355 that replaces Asp (D) with Glu (E), and a substitution mutation at position Q281 that replaces Gln (Q) with Glu (E).

17. The engineered DNA polymerase of claim 1, wherein the at least one amino acid substitution mutation is a substitution mutation at position D355 that replaces Asp (D) with Glu (E), a substitution mutation at position K250 that replaces Lys (K) with Cys (C), and a substitution mutation at position Q425 that replaces Gln (Q) with Cys (C).

18. The engineered DNA polymerase of claim 1, wherein the at least one amino acid substitution mutation is a substitution mutation at position D355 that replaces Asp (D) with Glu (E), a substitution mutation at position Q281 that replaces Gln (Q) with Glu (E), a substitution mutation at position K250 that replaces Lys (K) with Cys (C), and a substitution mutation at position Q425 that replaces Gln (Q) with Cys (C).

19. The engineered DNA polymerase of claim 1, further comprising an exogenous label covalently joined thereto.

20. The engineered DNA polymerase of claim 19, wherein the exogenous label comprises a fluorescent label.

21. The engineered DNA polymerase of claim 1, wherein the engineered DNA polymerase comprises $Mg^{2+}$-dependent phosphodiester bond forming activity.

22. The engineered DNA polymerase of claim 1,
wherein the differential affinity of the engineered DNA polymerase for a primed template nucleic acid in the presence and absence of a cognate nucleotide is greater than the differential affinity of the DNA polymerase of SEQ ID NO:4 for the primed template nucleic acid in the presence and absence of cognate nucleotide.

23. An isolated mutant DNA polymerase comprising a variant of the sequence of SEQ ID NO:2, said variant being at least 80% identical to SEQ ID NO:2 and wherein the variant comprises Glu (E) at position 290.

24. An isolated mutant DNA polymerase comprising a variant of the sequence of SEQ ID NO:2, said variant being at least 80% identical to SEQ ID NO:2 and wherein the variant comprises Cys (C) at position 259, and Cys (C) at position 434.

25. An isolated mutant DNA polymerase comprising a variant of the sequence of SEQ ID NO:2, said variant being at least 80% identical to SEQ ID NO:2 and wherein the variant comprises Glu (E) at position 290, Cys (C) at position 259, and Cys (C) at position 434.

26. An isolated mutant DNA polymerase comprising a variant of the sequence of SEQ ID NO:2, said variant being at least 80% identical to SEQ ID NO:2 and wherein the variant comprises Glu (E) at position 364, and further comprises Glu (E) at position 290.

27. An isolated mutant DNA polymerase comprising a variant of the sequence of SEQ ID NO:2, said variant being at least 80% identical to SEQ ID NO:2 and wherein the variant comprises Glu (E) at position 364, and further comprises Cys (C) at position 259 and Cys (C) at position 434.

28. An isolated mutant DNA polymerase comprising a variant of the sequence of SEQ ID NO:2, said variant being at least 80% identical to SEQ ID NO:2 and wherein the variant comprises Glu (E) at position 364, and further comprises Glu (E) at position 290, Cys (C) at position 259, and Cys (C) at position 434.

29. A reaction mixture, comprising:
a DNA polymerase selected from the group consisting of,
(i) an engineered DNA polymerase that comprises a variant of the sequence of SEQ ID NO:3, said variant being at least 80% identical to SEQ ID NO:3 and comprising an amino acid substitution mutation at one or more of positions K250, Q281, D355, Q425, and D532,
(ii) an engineered DNA polymerase that comprises a variant of the sequence of SEQ ID NO:2, said variant being at least 80% identical to SEQ ID NO:2 and wherein the variant comprises Glu (E) at position 290,
(iii) an engineered DNA polymerase that comprises a variant of the sequence of SEQ ID NO:2, said variant being at least 80% identical to SEQ ID NO:2 and wherein the variant comprises Cys (C) at position 259, and Cys (C) at position 434, and
(iv) an engineered DNA polymerase that comprises a variant of the sequence of SEQ ID NO:2, said variant being at least 80% identical to SEQ ID NO:2 and wherein the variant comprises Glu (E) at position 290, Cys (C) at position 259, and Cys (C) at position 434;
a primed template nucleic acid molecule, optionally comprising a reversible terminator nucleotide at a 3'-end thereof; and
at least one nucleotide.

30. A kit for identifying the cognate nucleotide for a primed template nucleic acid molecule, comprising:
a DNA polymerase selected from the group consisting of,
(i) an engineered DNA polymerase that comprises a variant of the sequence of SEQ ID NO:3, said variant being at least 80% identical to SEQ ID NO:3 and comprising an amino acid substitution mutation at one or more of positions K250, Q281, D355, Q425, and D532,
(ii) an engineered DNA polymerase that comprises a variant of the sequence of SEQ ID NO:2, said variant being at least 80% identical to SEQ ID NO:2 and wherein the variant comprises Glu (E) at position 290,
(iii) an engineered DNA polymerase that comprises a variant of the sequence of SEQ ID NO:2, said variant being at least 80% identical to SEQ ID NO:2 and wherein the variant comprises Cys (C) at position 259, and Cys (C) at position 434, and
(iv) an engineered DNA polymerase that comprises a variant of the sequence of SEQ ID NO:2, said variant being at least 80% identical to SEQ ID NO:2 and wherein the variant comprises Glu (E) at position 290, Cys (C) at position 259, and Cys (C) at position 434;
a plurality of nucleotides or analogs thereof; and
a plurality of reversible terminator nucleotides.

31. The isolated mutant DNA polymerase of claim 23, bound to a primed template nucleic acid molecule in combination with a nucleotide that is a next correct nucleotide for the primed template nucleic acid molecule.

32. The isolated mutant DNA polymerase of claim 23, which binds to a blocked primed template nucleic acid molecule in combination with a nucleotide that is a next correct nucleotide for the blocked primed template nucleic acid molecule.

33. The isolated mutant DNA polymerase of claim 24, bound to a primed template nucleic acid molecule in combination with a nucleotide that is a next correct nucleotide for the primed template nucleic acid molecule.

34. The isolated mutant DNA polymerase of claim 24, which binds to a blocked primed template nucleic acid molecule in combination with a nucleotide that is a next correct nucleotide for the blocked primed template nucleic acid molecule.

35. The isolated mutant DNA polymerase of claim 25, bound to a primed template nucleic acid molecule in combination with a nucleotide that is a next correct nucleotide for the primed template nucleic acid molecule.

36. The isolated mutant DNA polymerase of claim 25, which binds to a blocked primed template nucleic acid molecule in combination with a nucleotide that is a next correct nucleotide for the blocked primed template nucleic acid molecule.

37. The isolated mutant DNA polymerase of claim 26, bound to a primed template nucleic acid molecule in combination with a nucleotide that is a next correct nucleotide for the primed template nucleic acid molecule.

38. The isolated mutant DNA polymerase of claim 26, which binds to a blocked primed template nucleic acid molecule in combination with a nucleotide that is a next correct nucleotide for the blocked primed template nucleic acid molecule.

39. The isolated mutant DNA polymerase of claim 27, bound to a primed template nucleic acid molecule in combination with a nucleotide that is a next correct nucleotide for the primed template nucleic acid molecule.

40. The isolated mutant DNA polymerase of claim 27, which binds to a blocked primed template nucleic acid molecule in combination with a nucleotide that is a next correct nucleotide for the blocked primed template nucleic acid molecule.

41. The isolated mutant DNA polymerase of claim 28, bound to a primed template nucleic acid molecule in combination with a nucleotide that is a next correct nucleotide for the primed template nucleic acid molecule.

42. The isolated mutant DNA polymerase of claim 28, which binds to a blocked primed template nucleic acid molecule in combination with a nucleotide that is a next correct nucleotide for the blocked primed template nucleic acid molecule.

* * * * *